United States Patent
Mosko

(10) Patent No.: US 12,188,083 B2
(45) Date of Patent: Jan. 7, 2025

(54) PRODUCTS AND PROCESSES FOR NUCLEIC ACID DETECTION AND QUANTIFICATION

(71) Applicant: Agena Bioscience, Inc., San Diego, CA (US)

(72) Inventor: Michael Mosko, Poway, CA (US)

(73) Assignee: AGENA BIOSCIENCE, INC., San Diego, CA (US)

( * ) Notice: Subject to any disclaimer, the term of this patent is extended or adjusted under 35 U.S.C. 154(b) by 88 days.

(21) Appl. No.: 16/428,735

(22) Filed: May 31, 2019

(65) Prior Publication Data

US 2019/0367970 A1 Dec. 5, 2019

Related U.S. Application Data

(60) Provisional application No. 62/679,450, filed on Jun. 1, 2018.

(51) Int. Cl.
*C12Q 1/6827* (2018.01)
*C12Q 1/6813* (2018.01)

(52) U.S. Cl.
CPC ......... *C12Q 1/6827* (2013.01); *C12Q 1/6813* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,547,835 A | 8/1996 | Koester | |
| 6,043,031 A | 3/2000 | Koester et al. | |
| 8,003,317 B2 | 8/2011 | Beaulieu et al. | |
| 8,349,566 B2 | 1/2013 | Beaulieu et al. | |
| 9,068,223 B2 | 6/2015 | Beaulieu et al. | |
| 9,896,724 B2 | 2/2018 | Beaulieu et al. | |
| 10,233,489 B2 | 3/2019 | Nygren | |
| 10,513,728 B2 | 12/2019 | Nygren | |
| 10,604,791 B2 | 3/2020 | Honisch et al. | |
| 10,640,817 B2 * | 5/2020 | Nygren | C12Q 1/6827 |
| 10,865,439 B2 | 12/2020 | Nygren | |
| 2002/0177141 A1 * | 11/2002 | Chee | C12Q 1/6813 506/5 |
| 2003/0186234 A1 * | 10/2003 | Kurn | C12Q 1/6853 435/6.14 |
| 2005/0181394 A1 * | 8/2005 | Steemers | C12Q 1/6827 435/91.2 |
| 2005/0287533 A1 | 12/2005 | Ehrich et al. | |
| 2005/0287592 A1 | 12/2005 | Kless | |
| 2007/0122811 A1 | 5/2007 | Buzby | |
| 2008/0242555 A1 | 10/2008 | Shen et al. | |
| 2012/0028826 A1 | 2/2012 | Fu et al. | |
| 2012/0046178 A1 | 2/2012 | Van Den Boom et al. | |
| 2014/0011195 A1 | 1/2014 | Honisch et al. | |
| 2014/0242577 A1 * | 8/2014 | Peter | C12N 15/10 435/6.11 |
| 2017/0058335 A1 * | 3/2017 | Tao | C12Q 1/6853 |
| 2017/0247756 A1 | 8/2017 | Schreiber et al. | |
| 2018/0245146 A1 | 8/2018 | Beaulieu et al. | |
| 2020/0318169 A1 | 10/2020 | Honisch et al. | |
| 2021/0062254 A1 | 3/2021 | Nygren | |

FOREIGN PATENT DOCUMENTS

| | | |
|---|---|---|
| CN | 1461349 A | 12/2003 |
| CN | 1620515 A | 5/2005 |
| CN | 102203287 A | 9/2011 |
| CN | 103717751 A | 4/2014 |
| CN | 103917660 A | 7/2014 |
| CN | 105980579 A | 9/2016 |
| EP | 3 382 034 A1 | 10/2018 |
| WO | 97/37041 A2 | 10/1997 |
| WO | 02083949 A1 | 10/2002 |
| WO | 03052115 A2 | 6/2003 |
| WO | 2005/012578 A1 | 2/2005 |
| WO | 2010/056513 A2 | 5/2010 |
| WO | 2012/159060 A2 | 11/2012 |
| WO | 2012/159089 A1 | 11/2012 |
| WO | 2016/172571 A1 | 10/2016 |
| WO | 2016/172579 A1 | 10/2016 |
| WO | 2019/232460 A1 | 12/2019 |

OTHER PUBLICATIONS

Shimada et al. (Nucleic acids Research 2010 vol 38 p. 5692) (Year: 2010).*
Conserved Hypothetical Protein (Plasmid) [Thermus Thermophilus HB8], GenBank Accession No. BAD71974.1, Oct. 7, 2016, 2 pages.
International Search Report and Written Opinion mailed on Aug. 21, 2019 in International Patent Application No. PCT/US2019/035031, filed on May 31, 2019, 12 pages.
Auer et al., "Synthesis and Biological Applications of 2',3'-Dideoxynucleoside-5'-O-($\alpha$-thio) Triphosphates", Nucleosides & Nucleotides, 1989, 8(5&6):849-853.
Mosko et al., "Ultrasensitive Detection of Multiplexed Somatic Mutations Using MALDI-TOF Mass Spectrometry", The Journal of Molecular Diagnostics, 2016, 18(1):23-31.
Pierce et al., "Comparison of the GenMark Diagnostics eSensor Respiratory Viral Panel to Real-Time PCR for Detection of Respiratory Viruses in Children", Journal of Clinical Microbiology, Nov. 2012, 50(11):3458-3465.

(Continued)

*Primary Examiner* — Katherine D Salmon
(74) *Attorney, Agent, or Firm* — LOZA & LOZA LLP

(57) ABSTRACT

Provided herein are products and processes for primer extension reactions using chain terminating reagents and enzymes having 3' to 5' exonuclease activity, whereby unextended oligonucleotides are digested and extended oligonucleotides are not digested. Also provided herein are products and processes for the detection of the presence, absence or amount of one or more variants of a target nucleic acid species or a plurality of target nucleic acid species comprising primer extension reactions using chain terminating reagents and enzymes having 3' to 5' exonuclease activity, whereby unextended oligonucleotides are digested and extended oligonucleotides are not digested.

20 Claims, 7 Drawing Sheets
Specification includes a Sequence Listing.

(56) References Cited

OTHER PUBLICATIONS

Sakata et al., "Synthesis and Properties of Novel Acyclic Nucleotides", Article in Nucleic Acids Symposium Series, Feb. 2000, 44:47-48.
Shimada et al., "A Novel Single-Stranded DNA-Specific 3'-5' Exonuclease, Thermus Thermophilus Exonuclease I, Is Involved in Several DNA Repair Pathways", Nucleic Acids Research, May 2010, 38(17):5692-5705.
International Preliminary Report on Patentability Received dated Dec. 10, 2020 in International Patent Application No. PCT/US2019/035031, filed on May 31, 2019 and Published as WO 2019/232460 on Dec. 5, 2019, 8 pages.
Zhang, et al., "New Progress in Fluorescent Probe Research", Progress in Bioengineering, vol. 20, Issue 2, Apr. 25, 2000, pp. 14-15. (With English Abstract Only).
Zhong, et al., "Construction of Electrochemical Sensor for Breast Cancer Cells Based on Nucleic Acid Degradation Catalyzed by Exonuclease I", Analytical Chemistry, vol. 42, Issue 007, Dec. 31, 2014, pp. 1049-1052. (With English Abstract Only).

\* cited by examiner

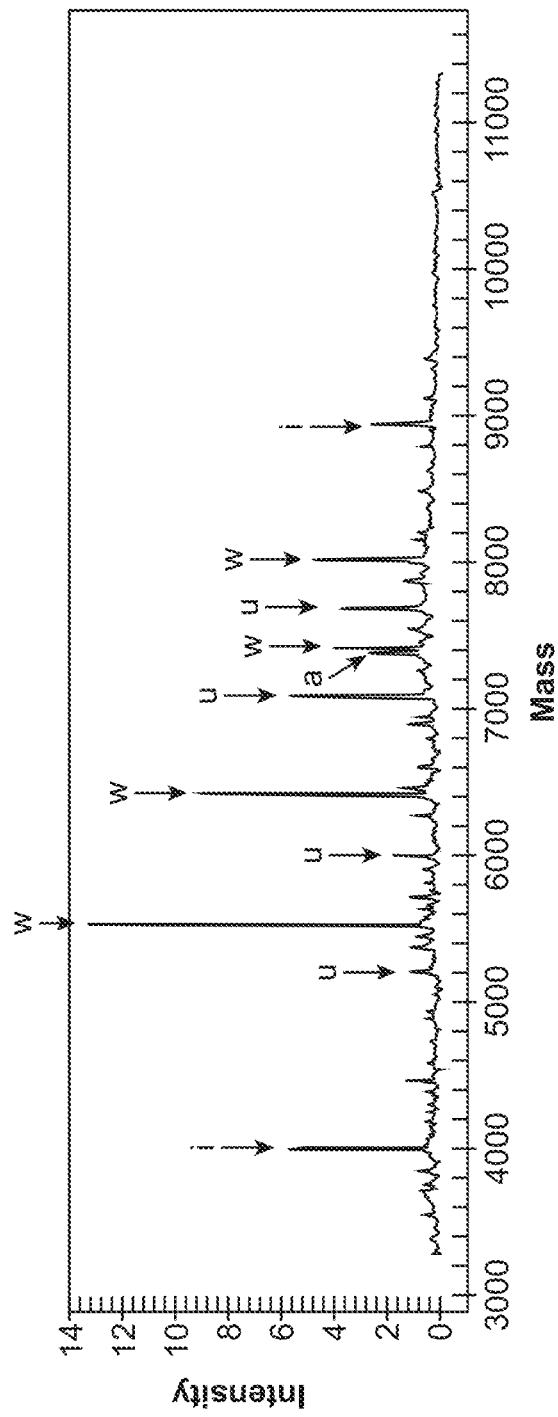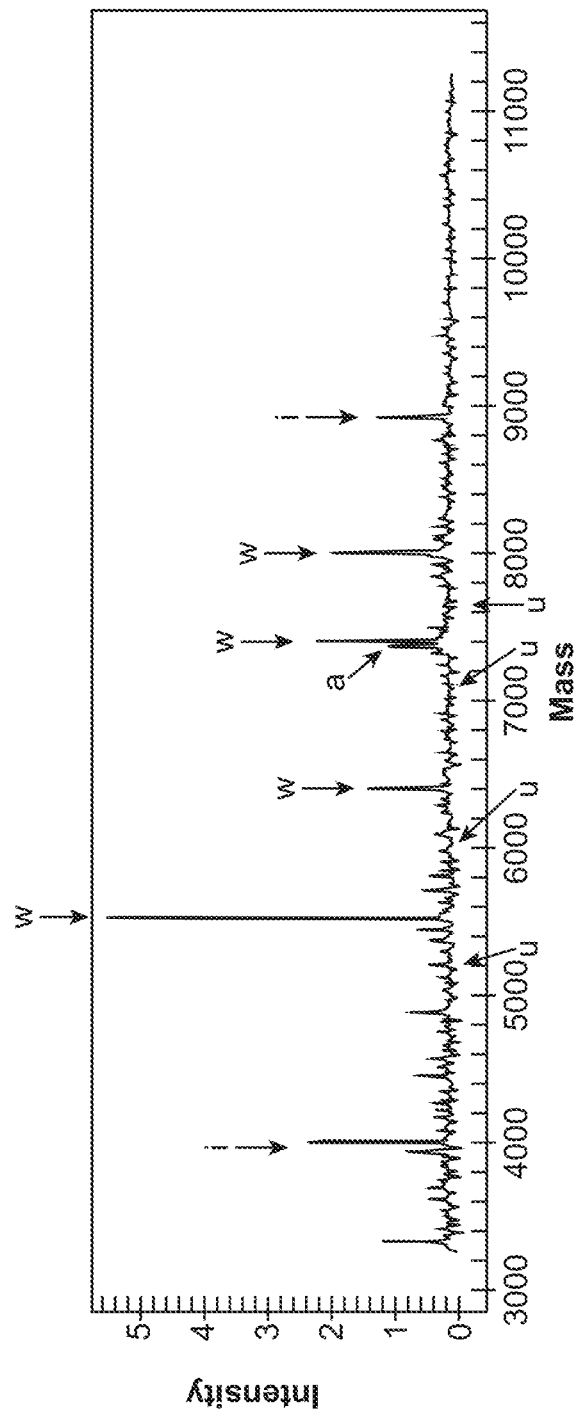

PRODUCTS AND PROCESSES FOR NUCLEIC ACID DETECTION AND QUANTIFICATION

RELATED PATENT APPLICATION(S)

This patent application claims the benefit of U.S. Provisional Patent Application No. 62/679,450, filed Jun. 1, 2018, entitled PRODUCTS AND PROCESSES FOR NUCLEIC ACID DETECTION AND QUANTIFICATION, naming Michael Mosko as inventor and designated.

This patent application is related to U.S. patent application Ser. No. 15/568,701, filed Oct. 23, 2017, entitled MULTIPLEX METHODS FOR DETECTION AND QUANTIFICATION OF MINOR VARIANTS, naming Anders Nygren as inventor, and designated. This application is also related to International PCT Application No. PCT/US2016/028980, filed Apr. 22, 2016, entitled MULTIPLEX METHODS FOR DETECTION AND QUANTIFICATION OF MINOR VARIANTS, naming Anders Nygren as inventor, and designated. This application is also related to U.S. Provisional Application No. 62/152,698 filed on Apr. 24, 2015, entitled MULTIPLEX METHODS FOR DETECTION AND QUANTIFICATION OF MINOR VARIANTS, naming Anders Nygren as inventor, and designated. This patent application is related to U.S. patent application Ser. No. 13/551,486 filed on Jul. 17, 2012, entitled PRODUCTS AND PROCESSES FOR MULTIPLEX NUCLEIC ACID IDENTIFICATION, naming Christiane Honisch, Dirk J. Van Den Boom, Michael Mosko, and Anders Nygren as inventors, and designated. AGB-6020-CT2t, which is a continuation application of international patent application no. PCT/US2012/038710 filed on May 18, 2012, entitled PRODUCTS AND PROCESSES FOR MULTIPLEX® NUCLEIC ACID IDENTIFICATION, naming Christiane Honisch, Dirk Johannes Van Den Boom, Michael Mosko, and Anders Nygren as inventors. This application is also related to U.S. patent application Ser. No. 15/136,024, filed Apr. 22, 2016, entitled MULTIPLEXED METHOD FOR THE IDENTIFICATION AND QUANTITATION OF MINOR ALLELES AND POLYMORPHISMS, naming Anders Nygren as inventor. This application is also related to U.S. Provisional Patent Application No. 62/280,951, filed Jan. 20, 2016, entitled MULTIPLEXED METHOD FOR THE IDENTIFICATION AND QUANTITATION OF MINOR ALLELES AND POLYMORPHISMS, naming Anders Nygren as inventor. This patent application is also related to U.S. Provisional Application No. 62/152,697, filed Apr. 24 2015, entitled MULTIPLEXED METHOD FOR THE IDENTIFICATION AND QUANTITATION OF MINOR ALLELES AND POLYMORPHISMS, naming Anders Nygren as inventor. This patent application is related to U.S. patent application Ser. No. 13/718,758, filed Dec. 18, 2012, naming Martin Beaulieu and Dirk Johannes van den Boom as inventors, entitled METHODS FOR HIGH LEVEL MULTIPLEXED POLYMERASE CHAN REACTIONS AND HOMOGENOUS MASS EXTENSION REACTIONS, which is a continuation of U.S. patent application Ser. No. 13/193,390, filed Jul. 28, 2011, now U.S. Pat. No. 8,349,566, naming Martin Beaulieu and Dirk Johannes van den Boom as inventors, entitled METHODS FOR HIGH LEVEL MULTIPLEXED POLYMERASE CHAN REACTIONS AND HOMOGENOUS MASS EXTENSION REACTIONS, which is a continuation of U.S. patent application Ser. No. 10/903,268, filed Jul. 30, 2004, now U.S. Pat. No. 8,003,317, naming Martin Beaulieu and Dirk Johannes van den Boom as inventors, entitled METHODS FOR HIGH LEVEL MULTIPLEXED POLYMERASE CHAN REACTIONS AND HOMOGENOUS MASS EXTENSION REACTIONS, which benefit of priority under 35 U.S.C. § 119(e) is claimed to U.S. provisional application Ser. No. 60/492,102, filed Jul. 31, 2003, to Martin Beaulieu and Dirk van den Boom, entitled METHODS FOR HIGH LEVEL MULTIPLEXED POLYMERASE CHAIN REACTIONS AND HOMOGENEOUS MASS EXTENSION REACTIONS. This application also is related to International PCT Application No. PCT/US2004/024953, filed Dec. 18, 2012, entitled METHODS FOR HIGH LEVEL MULTIPLEXED POLYMERASE CHAIN REACTIONS AND HOMOGENEOUS MASS EXTENSION REACTIONS, naming Martin Beaulieu and Dirk van den Boom as inventors.

The entire content of each the foregoing patent applications hereby is incorporated in its entirety by reference, including all text, tables and drawings.

SEQUENCE LISTING

The instant application contains a Sequence Listing which has been submitted electronically in ASCII format and is hereby incorporated by reference in its entirety. Said ASCII copy, created on May 23, 2019, is named AGB-7004-UT_SL.txt and is 17,219 bytes in size.

FIELD

The technology relates in part to identifying and/or quantitating nucleic acid variants. The technology also relates in part to methods of nucleic acid identification utilizing primer extension reactions and in which multiple target nucleic acids can be detected in one reaction.

BACKGROUND

The detection of specific nucleic acids is an important tool for diagnostic medicine and molecular biology research. Nucleic acid assays currently play roles in identifying infectious organisms such as bacteria and viruses, in probing the expression of normal genes and identifying mutant genes such as oncogenes, in typing tissue for compatibility preceding tissue transplantation, in matching tissue or blood samples for forensic medicine, and for exploring homology among genes from different species, for example.

SUMMARY

Provided in certain aspects is a method for primer extension comprising: (a) hybridizing a target nucleic acid to an oligonucleotide that comprises a region that corresponds to a portion of the target nucleic acid, thereby generating a hybridized oligonucleotide; (b) contacting the hybridized oligonucleotide with an extension composition comprising one or more chain terminating reagents under extension conditions; thereby generating extended oligonucleotides; and (c) contacting the products of (b) with an enzyme having 3' to 5' exonuclease activity, whereby unextended oligonucleotides are digested and extended oligonucleotides comprising a chain terminating reagent are not digested.

Also provided in certain aspects is a method for detecting the presence, absence or amount of one or more target nucleic acids, comprising: (a) hybridizing each of the one or more target nucleic acids to an oligonucleotide that comprises a region that corresponds to a portion of a target nucleic acid, thereby generating hybridized oligonucleotides; (b) contacting the hybridized oligonucleotides with an extension composition comprising one or more chain terminating reagents under extension conditions; thereby generating extended oligonucleotides; (c) contacting the products of (b) with an enzyme having 3' to 5' exonuclease activity, whereby unextended oligonucleotides are digested and extended oligonucleotides comprising a chain terminating reagent are not digested; and (c) analyzing the extended oligonucleotides, thereby detecting the presence, absence or amount of the one or more target nucleic acids.

Also provided in certain aspects is a method for detecting the presence, absence or amount of variants of a plurality of target nucleic acid species, comprising: (a) preparing a plurality of amplicons derived from a plurality of target nucleic acid species, or portions thereof, wherein each target nucleic acid species comprises a low-abundance variant and a high-abundance variant; (b) hybridizing the amplicons to a plurality of oligonucleotide species, each oligonucleotide species specifically corresponds to amplicons of a target nucleic acid species, wherein (i) an oligonucleotide species hybridizes to amplicons derived from the low-abundance variant and the high-abundance variant of a target nucleic acid species at a position 5' to a single base position that differs between the low-abundance variant and the high-abundance variant of the target nucleic acid species, thereby generating hybridized oligonucleotides; (c) contacting the hybridized oligonucleotides with an extension composition comprising a chain terminating reagent specific for the low-abundance variants under extension conditions; wherein the hybridized oligonucleotides that hybridize to the low-abundance variants are extended by the chain terminating reagent, thereby generating extended oligonucleotides and the hybridized oligonucleotides that hybridize to the high-abundance variants are not extended; (d) contacting the products of (c) with an enzyme having 3' to 5' exonuclease activity, whereby unextended oligonucleotides are digested and extended oligonucleotides are not digested; and (e) analyzing the extended oligonucleotides of (d), thereby detecting the presence, absence or amount of variants of a plurality of target nucleic acid species.

Also provided in certain aspects is a method for detecting the presence, absence or amount of variants of a plurality of target nucleic acid species, comprising: (a) preparing a plurality of amplicons derived from a plurality of target nucleic acid species, or portions thereof, wherein each target nucleic acid species comprises a low-abundance variant and a high-abundance variant; (b) hybridizing the amplicons to a plurality of oligonucleotide species, each oligonucleotide species specifically corresponds to amplicons of a target nucleic acid species, wherein (i) an oligonucleotide species hybridizes to amplicons derived from the low-abundance variant and the high-abundance variant of a target nucleic acid species at a position 5' to a single base position that differs between the low-abundance variant and the high-abundance variant of the target nucleic acid species, (ii) the nucleotide at the single base position is the same or different for each of the high-abundance variants of the plurality of target nucleic acid species, (iii) the nucleotide at the single base position is the same for each of the low-abundance variants of the plurality of target nucleic acid species and (iv) none of the nucleotides at the single base positions for the high-abundance variants of the plurality of target nucleic acid species is the same as the nucleotide at the single base position for the low-abundance variants of the plurality of target nucleic acid species; thereby generating hybridized oligonucleotides; (c) contacting the hybridized oligonucleotides with an extension composition comprising a chain terminating reagent specific for the low-abundance variants and one, two or three chain terminating reagents specific for one or more of the high-abundance variants under extension conditions; wherein: (i) the concentration of the one, two or three chain terminating reagents specific for one or more high-abundance variants are each at a concentration less than the concentration of the chain terminating reagent specific for the low-abundance variants and (ii) the extension conditions comprise multiple thermal cycles, thereby generating extended oligonucleotides comprising a chain terminating reagent specific for the low-abundance variants of the plurality of target nucleic acid species and extended oligonucleotides comprising a chain terminating reagent specific for the high-abundance variants of the plurality of target nucleic acid species; (d) contacting the products of (c) with an enzyme having 3' to 5' exonuclease activity, whereby unextended oligonucleotides are digested and extended oligonucleotides comprising a chain terminating reagent are not digested; and (e) detecting the extended oligonucleotides; thereby detecting the presence, absence or amounts of the variants of a plurality of nucleic acid species.

Also provided in certain aspects is a method for detecting the presence, absence or amount of variants of a plurality of target nucleic acid species, comprising: (a) preparing a plurality of amplicons derived from a plurality of target nucleic acid species, or portions thereof, wherein each target nucleic acid species comprises a low-abundance variant and a high-abundance variant; (b) hybridizing the amplicons to a plurality of oligonucleotide species, each oligonucleotide species specifically corresponds to amplicons of a target nucleic acid species, wherein (i) an oligonucleotide species hybridizes to amplicons derived from the low-abundance variant and the high-abundance variant of a target nucleic acid species at a position 5' to a single base position that differs between the low-abundance variant and the high-abundance variant of the target nucleic acid species, thereby generating hybridized oligonucleotides; (c) contacting the hybridized oligonucleotides with an extension composition comprising chain terminating reagents, under extension conditions, wherein: (i) the high-abundance variants share a common chain terminating reagent that is specific for the high-abundance variants and is not specific for the low-abundance variants, and (ii) each of the low-abundance variants has a chain terminating reagent that is specific for the low-abundance variant and is not specific for the high-abundance variant, wherein the chain terminating reagent that is specific for the low-abundance variant either: (A) is unique for a particular low-abundance variant in the amplified mixture and is not shared by the other low-abundance variants in the amplified mixture, or (B) at least one of the low-abundance variants share a common chain terminating reagent with at least one other low-abundance variant in the amplified mixture, whereby the oligonucleotides are extended up to, or through, the nucleotide positions that are different in the low-abundance variant relative to the high-abundance variant, thereby generating chain terminated extension products corresponding to the low-abundance variants and the high-abundance variants, respectively, wherein the concentration of the chain terminating reagent specific for the high-abundance variant is less than the concentration of each of the chain terminating reagent(s) specific for the low-abundance variants; (d) contacting the products of (c) with an enzyme with 3' to 5' exonuclease activity, whereby unextended oligonucleotides are digested and extended oligonucleotides comprising a chain terminating reagent are not digested; and (e) analyzing the extended oligonucleotides, thereby detecting the presence, absence or amount of the low-abundance variants.

Also provided in certain aspects is a method for detecting the presence, absence or amount of variants of a plurality of target nucleic acid species, comprising: (a) preparing a plurality of amplicons derived from a plurality of target nucleic acid species, or portions thereof, wherein each target nucleic acid species comprises at least two variants; (b) hybridizing the amplicons to a plurality of oligonucleotide species, each oligonucleotide species specifically corresponds to amplicons of a target nucleic acid species, wherein (i) an oligonucleotide species hybridizes to amplicons derived from the variants of a target nucleic acid species at a position 5' to a single base position that differs between the variants of the target nucleic acid species, thereby generating hybridized oligonucleotides; (c) contacting the hybridized oligonucleotides with an extension composition comprising two, three or four chain terminating reagents in equimolar concentrations, whereby the oligonucleotides are extended up to, or through, the nucleotide positions that are different between the variants of a target nucleic acid species, thereby generating chain terminated extension products corresponding to the variants; (d) contacting the products of (c) with an enzyme with 3' to 5' exonuclease activity, whereby unextended oligonucleotides are digested and extended oligonucleotides are not digested; and (e) analyzing the extended oligonucleotides; thereby detecting the presence, absence or amount of the variants.

Also provided in certain aspects are kits comprising an enzyme having 3' to 5' exonuclease activity and one or more chain terminating reagents that inhibit the activity of the enzyme on an oligonucleotide when the chain terminating reagent is at the 3' terminus of the oligonucleotide.

Certain embodiments are described further in the following description, examples, claims and drawings.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

FIG. 7A and FIG. 7B show spectra of a high-sensitivity assay (iPLEX® HS) without Chop Block conditioning (7A) and with Chop Block Conditioning (7B).

FIG. 8 shows spectra of an ultra-high sensitivity assay (UltraSEEK™) processed with Chop Block reagent.

DETAILED DESCRIPTION

Figure 1:
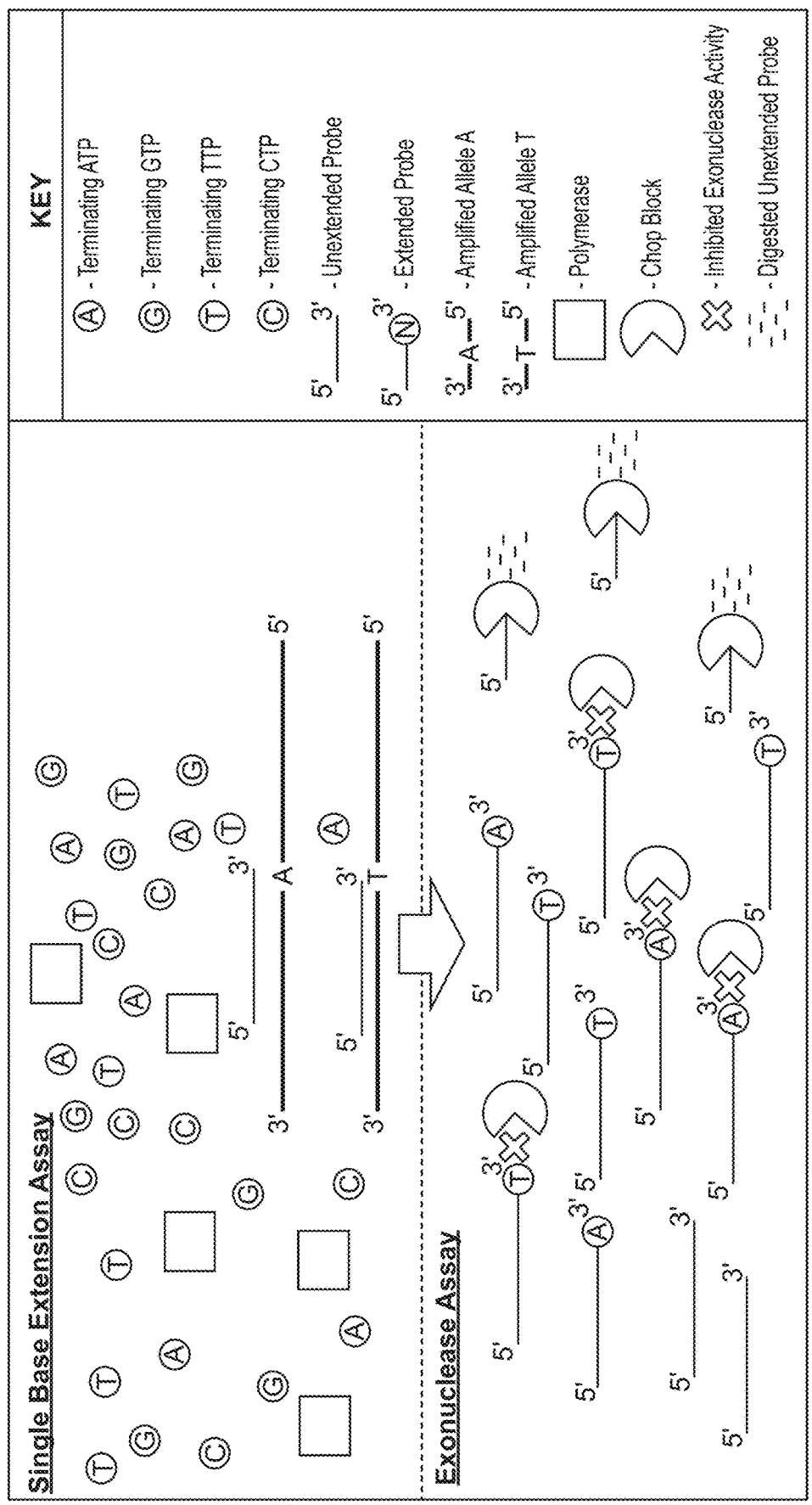
FIG. 1 is a schematic showing a single base extension genotyping assay with an exonuclease reagent (Chop Block reagent).

Methods for determining the presence, absence or amount of variants of a target nucleic acid species or a target nucleic acid or variants of a plurality of target nucleic acid species or target nucleic acids described herein find multiple uses by the person of ordinary skill in the art (hereafter referred to herein as the "person of ordinary skill"). Such methods can be utilized, for example, to: (a) rapidly determine whether a particular target sequence (e.g. a target sequence comprising a genetic variation) is present in a sample; (b) perform mixture analysis, e.g., identify a mixture and/or its composition or determine the frequency of a target sequence in a mixture (e.g., mixed communities, quasispecies); (c) detect sequence variations (e.g., mutations, single nucleotide polymorphisms) in a sample; (d) perform haplotyping determinations; (e) perform microorganism (e.g., pathogen) typing; (f) detect the presence or absence of a microorganism target sequence in a sample; (g) identify disease markers; (h) detect microsatellites; (i) identify short tandem repeats; (j) identify an organism or organisms; (k) detect allelic variations; (l) determine allelic frequency; (m) determine methylation patterns; (n) perform epigenetic determinations; (o) re-sequence a region of a biomolecule; (p) perform analyses in human clinical research and medicine (e.g. cancer marker detection, sequence variation detection; detection of sequence signatures favorable or unfavorable for a particular drug administration), (q) perform HLA typing; (r) perform forensics analyses; (s) perform vaccine quality control analyses; (t) monitor treatments; (u) perform vector identity analyses; (v) perform vaccine or production strain quality control and (w) test strain identity (x) plants. Such methods also may be utilized, for example, in a variety of fields, including, without limitation, in commercial, education, medical, agriculture, environmental, disease monitoring, military defense, and forensics fields.

Provided herein are methods for carrying out a primer extension reaction that include contacting an oligonucleotide hybridized to a target nucleic acid with an extension composition comprising one or more chain terminating reagents under extension conditions for generating extended oligonucleotides and contacting the products of the primer extension reaction (extended and unextended oligonucleotides) with an enzyme having 3' to 5' exonuclease activity, whereby unextended oligonucleotides are digested and extended oligonucleotides are not digested. The methods described herein thus provide for the removal of unextended oligonucleotides (primers) from an extension reaction. Removal of unextended oligonucleotides (primers) from an extension reaction is useful in methods described herein for the detection of the presence, absence or amount of one or more target nucleic acids and in methods for the detection of the presence, absence or amount of one or more variants of a target nucleic acid species or a plurality of target nucleic acid species.

Nucleic Acids

As used herein, the term "nucleic acid" refers to an oligonucleotide or polynucleotide, including, without limitation, natural nucleic acids (e.g., deoxyribonucleic acid (DNA), ribonucleic acid (RNA)), synthetic nucleic acids, non-natural nucleic acids (e.g., peptide nucleic acid (PNA)), unmodified nucleic acids, modified nucleic acids (e.g., methylated DNA or RNA, labeled DNA or RNA, DNA or RNA having one or more modified nucleotides). Reference to a nucleic acid as a "polynucleotide" refers to two or more nucleotides or nucleotide analogs linked by a covalent bond. Nucleic acids may be any type of nucleic acid suitable for use with processes described herein. A nucleic acid in certain embodiments can be DNA (e.g., complementary DNA (cDNA), genomic DNA (gDNA), plasmids and vector DNA and the like), RNA (e.g., viral RNA, message RNA (mRNA), short inhibitory RNA (siRNA), ribosomal RNA (rRNA), tRNA and the like), and/or DNA or RNA analogs (e.g., containing base analogs, sugar analogs and/or a non-native backbone and the like). A nucleic acid can be in any form useful for conducting processes herein (e.g., linear, circular, supercoiled, single-stranded, double-stranded and the like). A nucleic acid may be, or may be from, a plasmid, phage, autonomously replicating sequence (ARS), centromere, artificial chromosome, chromosome, a cell, a cell nucleus or cytoplasm of a cell in certain embodiments. A nucleic acid in some embodiments is from a single chromosome (e.g., a nucleic acid sample may be from one chromosome of a sample obtained from a diploid organism). In the case of fetal nucleic acid, the nucleic acid may be from the paternal allele, the maternal allele or the maternal and paternal allele.

The term "target nucleic acid" as used herein can refer to a nucleic acid having a nucleotide sequences that differs by one or more nucleotides from the sequence of another target nucleic acid when the nucleotide sequences are aligned. In some embodiments a target nucleic acid may or may not have a variant.

The term "target nucleic acid species," as used herein can refer to any nucleic acid species of interest in a sample. A target nucleic acid species comprises nucleic acids having nucleotide sequences that differs by one or more nucleotides when the nucleotide sequences are aligned. The nucleic acids of a target nucleic acid species can differ by one or more nucleotides (e.g., about 1, 2, 3, 4, 5, 10, 15, 20, 25, 30, 35, 40, 45, 50, 55, 60, 65, 70, 75, 80, 85, 90, 95, 100 or more than 100 nucleotide differences). A "target nucleic acid species" can include, without limitation two or more alleles. As used herein, the term "nucleic acid species" refers to nucleic acid that differ by one or more features and can be referred to as "variants." Features include, without limitation, one or more methyl groups or a methylation state, one or more phosphates, one or more acetyl groups, and one or more deletions, additions or substitutions of one or more nucleotides. Examples of one or more deletions, additions or substitutions of one or more nucleotides include, without limitation, the presence or absence of a particular mutation, presence or absence of a nucleotide substitution (e.g., single nucleotide polymorphism (SNP)), presence or absence of a repeat sequence (e.g., di-, tri-, tetra-, penta-nucleotide repeat), presence or absence of a marker (e.g., microsatellite) and presence of absence of a distinguishing sequence (e.g., a sequence that distinguishes one organism from another (e.g., a sequence that distinguishes one viral strain from another viral strain)). Different nucleic acids of a target nucleic acid species and different target nucleic acids species may be distinguished by any known method, for example, by mass, binding, distinguishable tags and the like, as described herein.

In some embodiments variants of target nucleic acid species can be present in a sample at a frequency or copy number that is approximately equal (e.g., a SNP). In some embodiments, variants of target nucleic acid species can be present in a sample at a different frequency or copy number. In some embodiments, one variant can be present in greater abundance than other variants. In some embodiments, a variant of greater abundance is referred to as wild type and a variant of lesser abundance is referred to as mutant. In some embodiments a target nucleic acid species comprises a first and second variant where the first or the second variant is represented in greater abundance (more template is present) than the other variant i.e., a high-abundance variant and a low-abundance variant or major variant and minor variant. A variant that is represented in a greater abundance generally is present at a higher concentration or is represented by a greater number of molecules (e.g. copies) when compared to another variant. A higher concentration can be 2-fold or more. In some embodiments, a higher concentration is 10-fold or more. In some embodiments, a higher concentration is a 100-fold, a 1000-fold or 10000-fold or more. In some embodiments, one variant represents a wild type sequence and is present at a 100-fold or higher concentration than another variant. In some embodiments, a variant (low-abundance variant) is represented at a significantly lower concentration than another variant (e.g. a wild type, high-abundance variant) and represents less of the target nucleic acid species in a sample (total amount of a target nucleic acid species is the amount of the high-abundance variant and the one or more low-abundance variants) In some embodiments, the methods provided herein can be used to detect the presence or absence of a low-abundance variant that represents less than 30%, 20%, 15%, 10%, 8%, 5%, 4%, 3%, 2%, 1%, 0.8%, 0.75%, 0.5%, 0.1%, 0.05%, 0.01% or less of the target nucleic acid species. In some embodiments, the methods provided herein can be used to detect the presence or absence of a low-abundance variant that represents between about 1% to about 10% of the target nucleic acid species. In some embodiments, the methods provided herein can be used to detect the presence or absence of a low-abundance variant that represents about 5% or less of the target nucleic acid species. In some embodiments, the methods provided herein can be used to detect the presence or absence of a low-abundance variant that represents between about 5% to about 0.75% of the target nucleic acid species. In some embodiments, the methods provided herein can be used to detect the presence or absence of a low-abundance variant that represents between about 5% to about 0.1% of the target nucleic acid species. In some embodiments, the methods provided herein can be used to detect the presence or absence of a low-abundance variant that represents about 1% or less of the target nucleic acid species. In some embodiments, the methods provided herein can be used to detect the presence or absence of a low-abundance variant that represents between about 0.1% to about 0.01% of the target nucleic acid species.

In some embodiments, for a target nucleic acid species the total copy number of the low-abundance variant and the high-abundance variant is at least about 1000 copies (molecules) and the low-abundance variant represents 0.1% of the total copy number. In some embodiments, for a target nucleic acid species the total copy number of the low-abundance variant and the high-abundance variant is at least about 100 copies (molecules) and the low-abundance variant represents about 0.1% of the total copy number. In some embodiments, for a target nucleic acid species the copy number of the low-abundance variant is about 0.01% to about 0.1% of the total copy number of a target nucleic acid species.

In some embodiments of the methods provided herein, a sample can contain a mixture of one or more target nucleic acid species (each target nucleic acid species can have a low-abundance and high-abundance variant), or a mixture can be generated by combining more than one sample containing one or more target nucleic acid species (each target nucleic acid species can have a low-abundance and high-abundance variant). The low-abundance variant can be a variant of a high-abundance variant and can include, but is not limited to, a mutant (low-abundance variant) of a wild type (high-abundance variant) allele, a variant of a gene that is found in more than one host (e.g., a viral oncogene (low-abundance variant) that is a variant of a normal, healthy gene (high-abundance variant)), a polymorphism, including a single nucleotide polymorphism (SNP), an insertion, deletion or other mutated form of the high-abundance variant.

As used herein, the term "plurality of target nucleic acid species" refers to more than one target nucleic acid species. A plurality of target nucleic acid species can be about 2 to about 10000 target nucleic acid species, about 2 to about 1000 target nucleic acid species, about 2 to about 500 target nucleic acid species, or sometimes about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900, 1000, 2000, 3000, 4000, 5000, 6000, 7000, 8000, 9000 or 10000 target nucleic acid species, in certain embodiments. In certain embodiments a plurality of target nucleic acid species are in one or more reaction vessels and each vessel contains more than one target nucleic acid species. In certain embodiments a plurality of target nucleic acid species are in one reaction vessel. In certain embodiments a plurality of target nucleic acid species is about 2 to about 100 target nucleic acid species. In certain embodiments the about 2 to about 100 target nucleic acid species are in a single reaction vessel.

Detection or identification of nucleic acids as provided in the methods described herein can result in detection of a low-abundance variant and can indicate the presence, absence or amount of a particular mutation, sequence variation (mutation or polymorphism) or genetic variation (e.g. sequence variation, sequence difference or polymorphism). Detection or identification of nucleic acids as provided in the methods described herein can also result in detection or identification of a high-abundance variant, which can serve as a positive control. Within the plurality of target nucleic acid species, there can be detection and/or quantification of the same or different species; detection and/or quantification of low-abundance variants that are all variants of the same high-abundance variant or a plurality of low-abundance variants that are variants of a plurality of high-abundance variants.

In some embodiments an oligonucleotide species is hybridized to a nucleic acid template (e.g. an amplicon) of a variant of a target nucleic acid species, thereby forming a double stranded nucleic acid and the oligonucleotide species that is hybridized to the template is referred to herein as a hybridized oligonucleotide species. In some embodiments a hybridized oligonucleotide species can comprise one or more nucleotides that are not hybridized to the template. For example, a hybridized oligonucleotide species can comprise one or more mismatched nucleotides (e.g. non-complementary nucleotides) and sometimes a 5' and/or 3' region of nucleotides that do not hybridize. In some embodiments a hybridized oligonucleotide species comprises a tag (e.g. a mass distinguishable tag, a sequence tag, a light emitting tag or a radioactive tag). In some embodiments a hybridized oligonucleotide species comprises a capture agent (e.g. biotin, or any member of binding pair). In some embodiments a hybridized oligonucleotide species comprises a terminating nucleotide. The terms "correspond," "corresponds," "corresponding," as used herein in reference to oligonucleotide species that "correspond" to templates such as target nucleic acids, target nucleic acid species, or amplicon of a target nucleic acid/target nucleic acid species/variant of a target nucleic acid species refers to oligonucleotide species that hybridize entirely (complete sequence) or in part (a portion of the sequence) to a template sequence. In some embodiments, the oligonucleotide species hybridizes "specifically" to a template, i.e., the sequence of the oligonucleotide species hybridizes to a particular template or high abundance/low abundance variant of a template relative to other templates in a mixture of templates.

As used herein, the term "nucleotides" refers to natural and non-natural nucleotides. Nucleotides include, but are not limited to, naturally occurring nucleoside mono-, di-, and triphosphates: deoxyadenosine mono-, di- and triphosphate; deoxyguanosine mono-, di- and triphosphate; deoxythymidine mono-, di- and triphosphate; deoxycytidine mono-, di- and triphosphate; deoxyuridine mono-, di- and triphosphate; and deoxyinosine mono-, di- and triphosphate (referred to herein as dA, dG, dT, dC, dU and dI, or A, G, T, C, U and I respectively). Nucleotides also include, but are not limited to, modified nucleotides and nucleotide analogs. Modified nucleotides and nucleotide analogs include, without limitation, dideoxynucleotides, acyclic nucleotides, deazapurine nucleotides, e.g., 7-deaza-deoxyguanosine (7-deaza-dG) and 7-deaza-deoxyadenosine (7-deaza-dA) mono-, di- and triphosphates, deutero-deoxythymidine (deutero-dT) mon-, di- and triphosphates, methylated nucleotides e.g., 5-methyldeoxycytidine triphosphate, $^{13}O/^{15}N$ labeled nucleotides and deoxyinosine mono-, di- and triphosphate. Modified nucleotides, isotopically enriched nucleotides, depleted nucleotides, tagged and labeled nucleotides and nucleotide analogs can be obtained using a variety of combinations of functionality and attachment positions.

The term "composition" as used herein with reference to nucleic acids refers to a tangible item that includes one or more target nucleic acids or target nucleic acid species. A composition sometimes is a sample extracted from a source, but also a composition of all samples at the source, and at times is the source of one or more nucleic acids. A composition can comprise nucleic acids. In some embodiments, a composition can comprise genomic DNA. In some embodiments, a composition can comprise synthetic DNA. In some embodiments, a composition can comprise maternal DNA, fetal DNA or a mixture of maternal and fetal DNA. In some embodiments, a composition can comprise fragments of genomic DNA. In some embodiments a composition can comprise nucleic acids derived from a virus, bacteria, yeast, fungus, mammal or mixture thereof.

A nucleic acid sample can be derived from one or more sources and can contain a mixture of target nucleic acid species, each of which can have a high-abundance variant and a low-abundance variant or variants present at a different copy number. A nucleic acid sample can be derived from one or more sources and can contain a mixture of target nucleic acid species, each of which can have variants present at an equivalent copy number. Samples also can be combined to generate a mixture that includes different target nucleic acid species with low-abundance and high-abundance variants or variants present at a different copy number. Samples also can be combined to generate a mixture that includes different target nucleic acid species, each of which can have variants present at an equivalent copy number. A sample may be collected from an organism, mineral or geological site (e.g., soil, rock, mineral deposit, fossil), or forensic site (e.g., crime scene, contraband or suspected contraband), for example. Thus, a source may be environmental, such as geological, agricultural, combat theater or soil sources, for example. A source also may be from any type of organism such as any plant, fungus, protistan, moneran, virus or animal, including but not limited, human, non-human, mammal, reptile, cattle, cat, dog, goat, swine, pig, monkey, ape, gorilla, bull, cow, bear, horse, sheep, poultry, mouse, rat, fish, dolphin, whale, and shark, or any animal or organism that may have a detectable nucleic acids. Sources also can refer to different parts of an organism such as internal parts, external parts, living or non-living cells, tissue, fluid and the like. A sample therefore may be a "biological sample," which refers to any material obtained from a living source or formerly-living source, for example, an animal such as a human or other mammal, a plant, a bacterium, a fungus, a protist or a virus. A source can be in any form, including, without limitation, a solid material such as a tissue, cells, a cell pellet, a cell extract, or a biopsy, or a biological fluid such as urine, blood, saliva, amniotic fluid, exudate from a region of infection or inflammation, or a mouth wash containing buccal cells, hair, cerebral spinal fluid and synovial fluid and organs. A sample also may be isolated at a different time point as compared to another sample, where each of the samples are from the same or a different source. A nucleic acid may be from a nucleic acid library, such as a cDNA or RNA library, for example. A nucleic acid may be a result of nucleic acid purification or isolation and/or amplification of nucleic acid molecules from the sample. Nucleic acids provided for sequence analysis processes described herein may contain nucleic acid from one sample or from two or more samples (e.g., from 1, 2, 3, 4, 5, 6, 7, 8, 9, 10, 11, 12, 13, 14, 15, 16, 17, 18, 19, 20, 25, 50, 75, 100, 200, 300, 400, 500, 600, 700, 800, 900 or 1000 or more samples).

Nucleic acids may be treated in a variety of manners during, prior to or subsequent to the methods provided herein. For example, a nucleic acid may be reduced in size (e.g., sheared, digested by nuclease or restriction enzyme, de-phosphorylated, de-methylated), increased in size (e.g., phosphorylated, reacted with a methylation-specific reagent, attached to a detectable label), treated with inhibitors of nucleic acid cleavage and the like.

Nucleic acids may be provided for analysis according to the methods provided herein without processing, in certain embodiments. In some embodiments, nucleic acid is provided for conducting methods described herein after processing. For example, a nucleic acid may be extracted, isolated, purified or amplified from a sample. The term "isolated" as used herein refers to nucleic acid removed from its original environment (e.g., the natural environment if it is naturally occurring, or a host cell if expressed exogenously), and thus is altered "by the hand of man" from its original environment. An isolated nucleic acid generally is provided with fewer non-nucleic acid components (e.g., protein, lipid) than the amount of components present in a source sample. A composition comprising isolated nucleic acid can be substantially isolated (e.g., about 90%, 91%, 92%, 93%, 94%, 95%, 96%, 97%, 98%, 99% or greater than 99% free of non-nucleic acid components). The term "purified" as used herein refers to nucleic acid provided that contains fewer nucleic acid species than in the sample source from which the nucleic acid is derived. A composition comprising nucleic acid may be substantially purified (e.g., about 90%, 91%, 92%, 93%, 94%, 95%, 96%, 97%, 98%, 99% or greater than 99% free of other nucleic acid species).

Nucleic acids may be processed by a method that generates nucleic acid fragments, in certain embodiments, before providing nucleic acid for a process described herein. In some embodiments, nucleic acid subjected to fragmentation or cleavage may have a nominal, average or mean length of about 5 to about 10,000 base pairs, about 100 to about 1,00 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 base pairs. Fragments can be generated by any suitable method known in the art, and the average, mean or nominal length of nucleic acid fragments can be controlled by selecting an appropriate fragment-generating procedure. In certain embodiments, nucleic acid of a relatively shorter length can be utilized to analyze sequences that contain little sequence variation and/or contain relatively large amounts of known nucleotide sequence information. In some embodiments, nucleic acid of a relatively longer length can be utilized to analyze sequences that contain greater sequence variation and/or contain relatively small amounts of unknown nucleotide sequence information.

Amplification and Extension

The term "oligonucleotide" as used herein refers to two or more nucleotides or nucleotide analogs linked by a covalent bond. An oligonucleotide is of any convenient length, and in some embodiments is about 5 to about 200 nucleotides in length, about 5 to about 150 nucleotides in length, about 5 to about 100 nucleotides in length, about 5 to about 75 nucleotides in length or about 5 to about 50 nucleotides in length, and sometimes is about 5, 6, 7, 8, 9, 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, or 200 nucleotides in length. Oligonucleotides may include deoxyribonucleic acid (DNA), ribonucleic acid (RNA), naturally occurring and/or non-naturally occurring nucleotides or combinations thereof and any chemical or enzymatic modification thereof (e.g. methylated DNA, DNA of modified nucleotides). The length of an oligonucleotide sometimes is shorter than the length of an amplicon or target nucleic acid, but not necessarily shorter than a primer or polynucleotide used for amplification. An oligonucleotide often comprises a nucleotide subsequence or a hybridization sequence that is complementary, or substantially complementary, to an amplicon or portion thereof, target nucleic acid or portion thereof or complement thereof (e.g., about 95%, 96%, 97%, 98%, 99% or greater than 99% identical to the amplicon or target nucleic acid complement when aligned). An oligonucleotide may contain a nucleotide subsequence not complementary to, or not substantially complementary to, an amplicon, target nucleic acid or complement thereof (e.g., at the 3' or 5' end of the nucleotide subsequence in the primer complementary to or substantially complementary to the amplicon). An oligonucleotide in certain embodiments, may contain a detectable molecule (e.g., a tag, fluorophore, radioisotope, colormetric agent, particle, enzyme and the like) and/or a member of a binding pair, in certain embodiments (e.g., biotin/avidin, biotin/streptavidin).

The term "in solution" as used herein refers to a liquid, such as a liquid containing one or more nucleic acids, for example. Nucleic acids and other components in solution may be dispersed throughout, and a solution often comprises water (e.g., aqueous solution). A solution may contain any convenient number of oligonucleotide species, and there often are at least the same number of oligonucleotide species as there are amplicon species or target nucleic acid species to be detected.

The term "hybridization sequence" as used herein refers to a nucleotide sequence in an oligonucleotide capable of specifically hybridizing to an amplicon or portion thereof, target nucleic acid or portion thereof, target nucleic acid species or portion thereof, target nucleic acid species variant or portion thereof or complement thereof. The hybridization sequence is readily designed and selected and can be of a length suitable for hybridizing to an amplicon, target sequence or complement thereof in solution as described herein. In some embodiments, the hybridization sequence in each oligonucleotide is about 5 to about 200 nucleotides in length (e.g., about 5 to 10, about 10 to 15, about 15 to 20, about 20 to 25, about 25 to 30, about 30 to 35, about 35 to 40, about 40 to 45, or about 45 to 50, about 50 to 70, about 80 to 90, about 90 to 110, about 100 to 120, about 110 to 130, about 120 to 140, about 130 to 150, about 140 to 160, about 150 to 170, about 160 to 180, about 170 to 190, about 180 to 200 nucleotides in length).

The term "hybridization conditions" as used herein refers to conditions under which two nucleic acids having complementary nucleotide sequences can interact with one another. Hybridization conditions can be high stringency, medium stringency or low stringency, and conditions for these varying degrees of stringency are known. Hybridization conditions often are selected that allow for amplification and/or extension depending on the application of interest.

The term "specifically hybridizing to one amplicon or target nucleic acid" as used herein refers to hybridizing substantially to one amplicon species or target nucleic acid species and not substantially hybridizing to other amplicon species or target nucleic acid species in the solution.

Specific hybridization rules out mismatches so that, for example, an oligonucleotide may be designed to hybridize specifically to a certain allele and only to that allele. An oligonucleotide that is homogenously matched or complementary to an allele will specifically hybridize to that allele, whereas if there is one or more base mismatches then no hybridization may occur.

The term "hybridization location" as used herein refers to a specific location on an amplicon or target nucleic acid to which another nucleic acid hybridizes. In certain embodiments, the terminus of an oligonucleotide is adjacent to or substantially adjacent to a site on an amplicon species or target nucleic acid species that has a different sequence than another amplicon species or target nucleic acid species. The terminus of an oligonucleotide is "adjacent" to a site when there are no nucleotides between the site and the oligonucleotide terminus. The terminus of an oligonucleotide is "substantially adjacent" to a site when there are 1, 2, 3, 4, 5, 6, 7, 8, 9 or 10 nucleotides between the site and the oligonucleotide terminus, in certain embodiments.

In some embodiments of the methods provided herein, a nucleic acid (e.g., a target nucleic acid or target nucleic acid species) can be amplified. As used herein, the term "amplifying," and grammatical variants thereof, refers to a process of generating copies of a template nucleic acid. For example, nucleic acid template may be subjected to a process that linearly or exponentially generates two or more nucleic acid amplicons (copies) having the same or substantially the same nucleotide sequence as the nucleotide sequence of the template, or a portion of the template. Nucleic acid amplification often is specific (e.g., amplicons have the same or substantially the same sequence), and can be non-specific (e.g., amplicons have different sequences) in certain embodiments. Nucleic acid amplification sometimes is beneficial when the amount of target sequence present in a sample is low. By amplifying the target sequences and detecting the amplicon synthesized, sensitivity of an assay can be improved, since fewer target sequences are needed at the beginning of the assay for detection of a target nucleic acid. A target nucleic acid or target nucleic acid species sometimes is not amplified prior to hybridizing an extension oligonucleotide, in certain embodiments.

Amplification conditions are known and can be selected for a particular nucleic acid that will be amplified. Amplification conditions include certain reagents some of which can include, without limitation, nucleotides (e.g., nucleotide triphosphates), modified nucleotides, oligonucleotides (e.g., primer oligonucleotides for polymerase-based amplification and oligonucleotide building blocks for ligase-based amplification), one or more salts (e.g., magnesium-containing salt), one or more buffers, one or more polymerizing agents (e.g., ligase enzyme, polymerase enzyme), one or more nicking enzymes (e.g., an enzyme that cleaves one strand of a double-stranded nucleic acid) and one or more nucleases (e.g., exonuclease, endonuclease, RNase). Any polymerase suitable for amplification may be utilized, such as a polymerase with or without exonuclease activity, DNA polymerase and RNA polymerase, mutant forms of these enzymes, for example. Any ligase suitable for joining the 5' of one oligonucleotide to the 3' end of another oligonucleotide can be utilized. Amplification conditions also can include certain reaction conditions, such as isothermal or temperature cycle conditions. Methods for cycling temperature in an amplification process are known, such as by using a thermocycle device. The term "cycling" refers to amplification (e.g. an amplification reaction or extension reaction) utilizing a single primer or multiple primers where temperature cycling is used. Amplification conditions also can, in some embodiments, include an emulsion agent (e.g., oil) that can be utilized to form multiple reaction compartments within which single nucleic acid molecule species can be amplified. Amplification is sometimes an exponential product generating process and sometimes is a linear product generating process.

In some embodiments an amplification reaction includes multiple temperature cycles repeated to amplify the amount of target nucleic acid species. In some embodiments the amplification reaction is cycled 2 or more times. In some embodiments the amplification reaction is cycled 10 or more times. In some embodiments the amplification reaction is cycled about 10, 15, 20, 50, 100, 200, 300 or more times. In some embodiments the amplification reaction is cycled 20 to 50 times. In some embodiments the amplification reaction is cycled 30 to 45 times.

A strand of a single-stranded nucleic acid target can be amplified and one or two strands of a double-stranded nucleic acid target can be amplified. An amplification product (amplicon), in some embodiments, is about 10 nucleotides to about 10,000 nucleotides in length, about 10 to about 1000 nucleotides in length, about 10 to about 500 nucleotides in length, 10 to about 100 nucleotides in length, and sometimes about 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900 or 1000 nucleotides in length.

Any suitable amplification technique and amplification conditions can be selected for a particular nucleic acid for amplification. Known amplification processes include, without limitation, polymerase chain reaction (PCR), extension and ligation, ligation amplification (or ligase chain reaction (LCR)) and amplification methods based on the use of Q-beta replicase or template-dependent polymerase (see US Patent Publication Number US20050287592). Also useful are strand displacement amplification (SDA), thermophilic SDA, nucleic acid sequence based amplification (3SR or NASBA) and transcription-associated amplification (TAA). Reagents, apparatus and hardware for conducting amplification processes are commercially available, and amplification conditions are known and can be selected for the target nucleic acid at hand.

Polymerase-based amplification can be effected, in certain embodiments, by employing universal primers. In such processes, hybridization regions that hybridize to one or more universal primers are incorporated into a template nucleic acid. Such hybridization regions can be incorporated into (i) a primer that hybridizes to a target nucleic acid and is extended, (ii) an oligonucleotide that is joined (e.g., ligated using a ligase enzyme) to a target nucleic acid or a product of (i), and/or (iii) a primer with a universal sequence manufactured on the 5' end of the gene specific sequence, for example. Amplification processes that involve universal primers can provide an advantage of amplifying a plurality of target nucleic acids using only one or two amplification primers, for example.

In certain embodiments, certain nucleic acids and combinations of nucleic acids representing one or more target nucleic acid species (e.g., only low-abundance variants, low-abundance variants and high-abundance variants together or variants that are neither high nor low-abundance) can be extended. The term "extension," and grammatical variants thereof, as used herein refers to elongating one strand of a nucleic acid. In some embodiments, an oligonucleotide that hybridizes to a target nucleic acid or variant of a target nucleic acid species or an amplicon generated from a target nucleic acid or variant of a target nucleic acid species can be extended in a primer extension reaction. A primer extension reaction refers to a molecular reaction in which a nucleic acid polymerase adds one or more nucleotides to the 3' terminus of a primer (e.g., oligonucleotide) in a template-specific manner. Conditions suitable for a primer extension reaction are known in the art. Generally, a primer is annealed, i.e., hybridized, to a target nucleic acid to form a primer-template complex. The primer-template complex is contacted with a DNA polymerase and one or more free nucleotides under suitable conditions to permit the addition of one or more nucleotides to the 3' end of the primer. In certain embodiments primers do not hybridize directly to a position that differs between the variants of a nucleic acid species, but hybridize to a position adjacent to such a position (e.g., 5' to a position). In some embodiments primers hybridize directly adjacent to a position that differs between variants of a target nucleic acid species. In some embodiments use of a chain terminating reagent in a primer extension reaction terminates primer extension once the chain terminating reagent is incorporated into the extension product.

An extension reaction is typically conducted under extension conditions, and a variety of such conditions are known and selected for a particular application. Extension conditions can include certain reagents, including without limitation, one or more oligonucleotides, extension nucleotides (e.g., nucleotide triphosphates (dNTPs)), terminating nucleotides (e.g., one or more dideoxynucleotide triphosphates (ddNTPs) or acyclic nucleotides), one or more salts (e.g., magnesium-containing salt), one or more buffers (e.g., with beta-NAD, Triton X-100), and one or more polymerizing agents (e.g., DNA polymerase, RNA polymerase).

Any suitable extension reaction can be selected and utilized. An extension reaction can be utilized, for example, to discriminate SNP alleles by the incorporation of deoxynucleotides and/or chain terminating nucleotides (e.g., dideoxynucleotides, acyclic nucleotides) to an extension oligonucleotide that hybridizes to a region adjacent to the SNP site in a target nucleic acid species. The primer often is extended with a polymerase. In some embodiments, the oligonucleotide is extended by only one deoxynucleotide or chain terminating nucleotide (e.g., dideoxynucleotide or acyclic nucleotide) complementary to the SNP site. In some embodiments, an oligonucleotide may be extended by dNTP incorporation and terminated by a ddNTP or an acyclic nucleotide, or terminated by a ddNTP or an acyclic nucleotide incorporation without dNTP extension in certain embodiments.

In some embodiments an oligonucleotide species can hybridize, under hybridization conditions, to a template (e.g. a target nucleic acid species) adjacent to a genetic variation or variant (e.g. the 3' end of the oligonucleotide species may be located 5' of the genetic variation site and may be 0 to 10 nucleotides away from the 5' end of the genetic variation site). Several variant may exist at a site of genetic variation in a target nucleic acid species. A genetic variant sometimes is a single nucleotide polymorphism (SNP) or single nucleotide variant. Several single nucleotide variants may exist at a single base position on a template target located 3' of a hybridized oligonucleotide. Several single nucleotide variants may differ by a single base located at a position on a template target that is 3' of a hybridized oligonucleotide species. In some embodiments an oligonucleotide species is extended by one nucleotide at the variant position. The oligonucleotide can be extended by any one of five terminating nucleotides (e.g. ddATP, ddUTP, ddTTP, ddGTP, ddCTP), depending on the number of variants present, in some embodiments. Target nucleic acid species variants, or their corresponding amplicons, can act as templates and can, in part, determine which terminating nucleotide is added to an oligonucleotide in the extension reaction. In certain embodiments, other chain terminating reagents or nucleotides (e.g., acyclic nucleotides or terminators) are utilized. In some embodiments a target nucleic acid species may have two, three or four variants.

Any suitable type of nucleotides can be incorporated into an amplification product or an extension product. In some embodiments nucleotides may be naturally occurring nucleotides, terminating nucleotides, or non-naturally occurring nucleotides (e.g., nucleotide analog or derivative). In some embodiments, certain nucleotides can comprise a detectable label and/or a member of a binding pair (e.g., the other member of the binding pair may be linked to a solid phase) or a fluorescent label pair for detection by FRET (e.g., one member of the pair can be on the terminating nucleotide that is incorporated into the UEP by extension and the other member of the pair can be elsewhere on the extension product oligonucleotide).

The term "chain terminating reagent," used interchangeably with "chain terminator reagent" or "chain terminator" herein refers to a molecule which, when added to an extension primer, stops the extension reaction. Chain terminators can include nucleotide analogs which, when present in a polynucleotide chain or oligonucleotide, prevent further extension of the chain or oligonucleotide. In certain embodiments a chain terminating reagent is a chain terminating nucleotide. In some embodiments a chain terminating nucleotide is a modified nucleotide that when incorporated at the 3' end of a nucleic acid molecule (e.g., oligonucleotide) in an extension reaction does not allow further incorporation of nucleotides into an oligonucleotide. In certain embodiments a chain terminating nucleotide is not removed from an oligonucleotide or polynucleotide chain when in the presence of an enzyme having 3' to 5' exonuclease activity. In certain embodiments, the '3 OH of the pentose sugar of a nucleotide can be substituted with moities that result in a nucleotide that is chain terminating and also resistant to removal by an enzyme with 3' to 5' exonuclease activity. In certain embodiments the chain terminating nucleotide is modified at a 3' position of the pentose sugar to replace an OH with another moiety, including but not limited to a phosphoryl group, an acetyl group, 3'-O-Methyl, 3'-O-(2-nitrobenzyl), 3'-O-Allyl, 3'-Azido, and 3'-Amino. In some embodiments, the 3' OH group is substituted with a hydrogen. In some embodiments, the modified nucleotide is a dideoxynucleotide. In some embodiments, the modified nucleotide is an acyclic nucleotide. Exemplary chain terminating reagents that are chain terminating nucleotides include dideoxynucleotides e.g., ddA (dideoxyadenine), ddT (dideoxythymine), ddC (dideoxycytosine), ddG (dideoxyguanine) and ddU (dideoxyuracil) and acyclic nucleotides e.g., acyATP, acyCTP, acyGTP, acyTTP, and acy-Bromo-UTP.

In some embodiments a chain terminating reagent that also blocks 3' to 5' exonuclease activity of an enzyme may specifically block the 3' to 5' exonuclease activity of a particular enzyme or may block 3' to 5' activity of a number of different enzymes.

In certain embodiments, for methods described herein, where both a low-abundance variant and a high abundance-variant of a target nucleic acid species are to be extended and detected, the concentration of a chain terminating reagent or reagents specific for a high-abundance variant or variants is less than the concentration of a chain terminating reagent or reagents specific for a low-abundance variant or variants. The concentration of a chain terminating reagent or reagents specific for a high-abundance variant or variants is less than about 30% of the concentration of a chain terminating reagent or reagents specific for low-abundance variant or variants, less than about 20%, about 0.01% to about 30%, about 0.3% to about 30%, about 1% to about 20%, about 0.5% to less than about 20%, about 0.5% to less than about 15%, about 1% to about 15%, about 1% to about 10%, about 2% to about 10% or about 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10%. In certain embodiments concentration of a chain terminating reagent or reagents specific for a high-abundance variant or variants is between about 0.1% to about 10% of the concentration of a chain terminating reagent or reagents specific for a low-abundance variant or variants, between about 0.01% to about 10% or about 0.01%, 0.05%, 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10%.

Extension can be conducted under isothermal conditions or under non-isothermal conditions (e.g., thermocycled conditions), in certain embodiments. One or more target nucleic acid species can be extended in an extension reaction and one or more variants of each target nucleic acid species can be extended. A nucleic acid can be extended by one or more nucleotides, and in some embodiments, the extension product is about 10 nucleotides to about 10,000 nucleotides in length, about 10 to about 1000 nucleotides in length, about 10 to about 500 nucleotides in length, 10 to about 100 nucleotides in length, and sometimes about 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900 or 1000 nucleotides in length. Incorporation of a terminating nucleotide (e.g., ddNTP), the hybridization location, or other factors, can determine the length to which the oligonucleotide is extended. In certain embodiments, amplification and extension processes are carried out in the same detection procedure.

In some embodiments an extension reaction includes multiple temperature cycles repeated to amplify the amount of extension product in the reaction. In some embodiments the extension reaction is cycled 2 or more times. In some embodiments the extension reaction is cycled 10 or more times. In some embodiments the extension reaction is cycled about 10, 15, 20, 50, 100, 200, 300, 400, 500 or 600 or more times. In some embodiments the extension reaction is cycled 20 to 50 times. In some embodiments the extension reaction is cycled 20 to 100 times. In some embodiments the extension reaction is cycled 20 to 300 times. In some embodiments the extension reaction is cycled 200 to 300 times. In some embodiments the extension reaction is cycled at least 50, 55, 60, 65, 70, 75, 80, 85, 90, 95 or 100 times.

In some embodiments an oligonucleotide hybridized to a variant of a target nucleic acid species is extended in the presence of an extension composition by one nucleotide. An extension composition can comprise one or more buffers, salts, enzymes (e.g. polymerases, Klenow, etc.), water, templates (e.g. DNA, RNA, amplicons, etc.), primers (e.g. oligonucleotides), nucleotide triphosphates, glycerol, macromolecular exclusion molecules and any other additives used in the art. An extension composition can comprise terminating nucleotides (e.g. dideoxynucleotides (e.g. ddNTPs) or acyclic nucleotides), non-terminating or extension nucleotides (e.g. dNTPs) or a mixture of terminating nucleotides and non-terminating nucleotides. An extension composition consisting essentially of a particular terminating nucleotide or terminating nucleotides, can contain any other component of an extension composition (e.g. buffers, salts, templates, primers, etc.), but does not contain any other terminating nucleotide or nucleotide triphosphate (e.g. dNTP) except those specified. For example an extension composition consisting essentially of ddTTP and ddCTP does not contain ddATP, ddGTP or any other dNTP. In some embodiments the nucleotides in an extension composition are only terminating nucleotides and oligonucleotides hybridized to a target nucleic acid, target nucleic acid species or amplicons thereof are extended by one nucleotide (i.e. sometimes there are no non-terminating or extension nucleotides in the extension composition). In some embodiments an extension composition consists essentially of terminating nucleotides (e.g. ddNTPs, acyclic nucleotides). In some embodiments the concentration of chain terminating reagents specific for high-abundance variants is less than the concentration of chain terminating reagents specific for low-abundance variants.

In some embodiments the amount of a target nucleic acid species low-abundance variant relative to the amount of a target nucleic acid species high-abundance variant (e.g., wild type) present in an assay is determined based on detection of the extended oligonucleotides representing the low-abundance variant and the high-abundance variant.

In some embodiments, a terminating nucleotide that is present (or, in some embodiments absent) in an extension composition determines which terminating nucleotide is added to an oligonucleotide. In some embodiments, an extension composition comprises one or more terminating nucleotides (e.g. ddNTPs or acyclic nucleotides). In certain embodiments having more than one terminating nucleotide, the two, three or four chain terminating nucleotides are different terminating nucleotide (i.e., not the same species, e.g., ddA, ddT, ddC, ddG, ddU, acyATP, acyCTP, acyGTP, acyTTP, and acy-Bromo-UTP.). In some embodiments, an extension composition comprises one or more terminating nucleotides and one or more non-terminating nucleotides (e.g. dNTPs). In some embodiments, an extension composition comprises terminating nucleotides that correspond to a specific variant (e.g. a first variant, minor variant or low-abundance variant) and therefore only allow extension of that specific variant. In some embodiments, a terminating nucleotide that would allow extension of a second variant (e.g. a wild type, major variant or high-abundance variant) is included in an extension composition thereby allowing for the extension of the second variant. In some embodiments, a method comprises contacting hybridized oligonucleotide species with an extension composition comprising one or more terminating nucleotides under extension conditions where the hybridized oligonucleotide species that hybridize to the first variant (e.g. a low-abundance variant, less abundant SNP variant, minor variant) are extended by a terminating nucleotide and the hybridized oligonucleotide species that hybridize to the second variant (e.g. wild type, high-abundance variant, major variant) are extended by a terminating nucleotide, thereby generating extended oligonucleotide species.

Amplicons produced by an amplification process, or extension products produced by an extension process, can be subjected to further processing. For example, amplicons can be contacted with an agent that removes phosphate moieties from free nucleotides that have not been incorporated into an amplicon or extension product. An example of such an agent is a phosphatase (e.g., alkaline phosphatase). In some embodiments, alkaline phosphatase is shrimp alkaline phosphatase or recombinant shrimp alkaline phosphatase. Amplicons and extension products also may be associated with a solid phase, may be washed, may be contacted with an agent that removes a terminal phosphate (e.g., exposure to a phosphatase), may be contacted with an agent that removes a terminal nucleotide (e.g., exonuclease), may be contacted with an agent that cleaves (e.g., endonuclease, ribonuclease), and the like.

In certain embodiments products produced by an extension process, can be subjected to further processing. In certain embodiments products of an extension reaction (extended and un-extended oligonucleotides) can be contacted with an agent with 3' to 5' exonuclease activity. An agent or enzyme having 3' to 5' exonuclease activity is capable of removing one or more nucleotides from the 3' end of an oligonucleotide in a sequential manner. In some embodiments an enzyme having 3' to 5' exonuclease activity can utilize both single-stranded and double-stranded DNA as a substrate. In some embodiments an enzyme having 3' to 5' exonuclease activity is specific for single-stranded DNA substrates. In certain embodiments an enzyme having 3' to 5' exonuclease activity is inhibited by certain modified reagents or modified nucleotides as described herein. In some embodiments a modified nucleotide able to inhibit the 3' to 5' exonuclease activity is a chain terminating nucleotide. In some embodiments, a chain terminiating nucleotide able to inhibit the 3' to 5' exonuclease activity is a dideoxynucleotide or an acyclic nucleotide. An enzyme having 3' to 5' exonuclease activity that is inhibited by certain chain terminating reagents or nucleotides (e.g., dideoxynucleotides or acyclic nucleotides) is referred to as a "Chop Block reagent" or "Chop Block enzyme."

In certain embodiments, an enzyme having 3' to 5' exonuclease activity that is inhibited by certain chain terminating reagents or nucleotides (Chop Block enzyme) is from *Thermus themophilus*. In some embodiments, the enzyme is *Thermus themophilus* exonuclease I or TTHB178 (see Shimada et al., *Nucl. Acids Res.*, 38 (17): 5692-5705 (2010), the contents of which are incorporated in their entirety by reference herein; see also protein and nucleic acid sequences set forth as SEQ ID NO:47 and SEQ ID NO:48, respectively, and submitted as GenBank Accession No. BAD71974.1). In embodiments, the TTHB178 enzyme has a histidine (His) tag (see, e.g., exemplary His-tagged TTHB178 whose purification is described in the Examples and whose sequence is set forth as SEQ ID NO:49).

In some embodiments, other single stranded 3' to 5' exonucleases that may be useful as Chop Block enzymes in the methods described herein, include, but are not limited to, *E. coli* exonuclease I, *E. coli* exonuclease X, *Homo sapiens* EXO1, *Homo sapiens* MRE11, *Homo sapiens* TREX1, *Homo sapiens* TREX2, *Homo sapiens* DNase III, *Homo sapiens* Apoptosis enhancing exonuclease, *B. subtilis* DnaQ-like (005231), *D. radiodurans* DnaQ-like (NP_051628 and NP_880692) and other single strand specific 3' to 5' exonucleases of the DnaQ superfamily.

In certain embodiments, a 3' to 5' exonuclease activity that is part of a polymerase holoenzyme may be separated from the other components of the holoezyme, particularly if the 3' to 5' activity domain resides on a distinct polypeptide of the holoenzyme. One of skill in the art would be able to identify chain terminating reagents (e.g., dideoxynucleotide, acyclic nucleotides or other modified nucleotides) that inhibit the 3' to 5' exonuclease activity of these enzymes. For example, the 3' to 5' exonuclease activity of Exo I is inhibited by a nucleotide having a substitution of a phophoryl or acetyl group for the 3'-OH of a pentose sugar. Accordingly, based on the above, one of skill in the art would be able to identify other Chop Block reagents useful in the methods described herein, in addition to TTHB178. Chop Block enzymes are typically stored in 50% glycerol at −20° C. In certain embodiments an enzyme having 3' to 5' exonuclease activity (Chop Block enzyme) is in a buffer with a glycerol concentration of about 50%. In certain embodiments an enzyme having 3' to 5' exonuclease activity or a Chop Block enzyme is in a buffer with a glycerol concentration of less than about 50%, or about 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1%. In some embodiments, an enzyme having 3' to 5' exonuclease activity (Chop Block enzyme) is in a buffer without glycerol. In some embodiments a buffer is Tris and the concentration of glycerol is about 10% or there is no glycerol.

The term "signal to noise ratio" as used herein refers to the quantitative measurement of the quality of a signal by quantifying the ratio of intensity of a signal relative to noise when using a detection process (e.g. mass spectrometry). In some embodiments, an intensive peak on one spectrum has a greater signal to noise ratio than a low intensity peak generated by the same analyte (e.g. an extended oligonucleotide species) on another spectrum. In some embodiments, noise is generated by extended oligonucleotide species derived from the high-abundance variants (e.g. wild type alleles, second variants, wild type variants). In some embodiments, the signal generated from an extended oligonucleotide species derived from a low-abundance variant (e.g. a first variant, minor variant, mutant variant, mutant allele, SNP) is obscured by the noise generated by a more abundant extended oligonucleotide species (e.g. a second variant, high-abundance variant, major variant, wild type variant, wild type allele), for example when using mass spectrometry. The term "signal" as used in the phrase "signal to noise ratio" herein refers to the intensity of a signal peak of an extended oligonucleotide species. In some embodiments, the term "signal" as used in the phrase "signal to noise ratio" herein generally refers to the intensity of a signal peak of an extended oligonucleotide species derived from a less abundant variant (e.g. a first variant, low-abundance variant, mutant variant, mutant allele, SNP). In some embodiments, a terminating nucleotide that would allow extension of a high-abundance variant (e.g., a second variant, a wild type or more abundant variant) is not included in an extension composition thereby eliminating the presence of the high-abundance extension product so that it cannot reduce the signal to noise ratio for a low-abundance variant (e.g. a first variant, mutant variant, mutant allele, SNP). In some embodiments, a terminating nucleotide that would allow extension of a high-abundance variant (e.g., a second variant, a wild type or more abundant variant) is included in an extension composition at a much lower concentration than the terminating nucleotide that allows extension for the low-abundance variant (i.e., an adjusted or skewed concentration) thereby not reducing the signal to noise ratio for a low-abundance variant (e.g. a first variant, mutant variant, mutant allele, SNP). In some embodiments, a method comprises contacting hybridized oligonucleotide species with an extension composition comprising one or more terminating nucleotides under extension conditions where the hybridized oligonucleotide species that hybridize to the low-abundance variant (e.g., minor variant, less abundant SNP variant) are extended by a terminating nucleotide and the hybridized oligonucleotide species that hybridize to the high-abundance variant (e.g. wild type or major variant) are extended by a terminating nucleotide that is provided at a lower concentration than the concentration of the terminating nucleotide for the low-abundance variant, thereby not significantly diminishing the signal to noise ratio compared to a condition where only the low-abundance variant in the absence of extending is the high abundance variant.

The term "sensitivity" as used herein refers to an amount of analyte that can be detected at a given signal-to-noise ratio when using a detection process (e.g. mass spectrometry). In some embodiments, sensitivity can be improved by decreasing the background or noise level. In some embodiments, noise is generated by extended oligonucleotide species derived from more abundant variants (e.g. wild type alleles, second variants, wild type variants). In some embodiments, sensitivity is increased when the signal generated from an extended oligonucleotide species derived from a more abundant extended oligonucleotide species (e.g. a second variant, wild type variant, wild type allele) is detected but reduced in intensity. In some embodiments, a terminating nucleotide that would allow extension of a more abundant variant (e.g. a wild type, high-abundance variant, major variant) is included in an extension composition at a reduced concentration that does not decrease the sensitivity for detection of a low-abundance variant (e.g. a minor variant, mutant variant, mutant allele, SNP). In certain embodiments, the terminating nucleotide specific for the high-abundance variants is at a concentration of about 10% or less relative to the concentration of the terminating nucleotide specific for the low-abundance variants. In certain embodiments, the terminating nucleotide specific for the high-abundance variants is between about 0.5% to less than about 20%, about 0.5% to less than about 15%, about 1% to about 15%, about 1% to about 10% or about 2% to about 10% of the concentration of the terminating nucleotide specific for the low-abundance variants. In certain embodiments, the terminating nucleotide specific for the high-abundance variants is at a concentration of about 0.01% to about 30% relative to the concentration of the terminating nucleotide specific for the low-abundance variants. In certain embodiments, the terminating nucleotide specific for the high-abundance variants is at a concentration of about 0.1% to about 30% relative to the concentration of the terminating nucleotide specific for the low-abundance variants. In certain embodiments, the terminating nucleotide specific for the high-abundance variants is at a concentration of about 0.5% to about 10% relative to the concentration of the terminating nucleotide specific for the low-abundance variants. In certain embodiments, the terminating nucleotide specific for the high-abundance variants is at a concentration of about 1% to about 2% relative to the concentration of the terminating nucleotide specific for the low-abundance variants.

In some embodiments removal of unextended oligonucleotides prior to analysis of extended oligonucleotides can produce an increase in the signal to noise ratio (SNR) and an accompanying increase in the sensitivity of detecting the signal produced by a low-abundance variant. Products of an extension reaction can include both extended oligonucleotides and unextended oligonucleotides. Unextended oligonucleotides can increase background noise which may interfere with the detection of low-abundance variants (which already produce a weak signal). In some embodiments of the methods described herein, unextended oligonucleotides are removed by the 3' to 5' exonuclease activity of an enzyme included in the reaction. In some embodiments of the methods described herein, unextended oligonucleotides often produce a significant signal in certain regions of a spectra, thus occupying these regions and precluding the design of extended oligonucleotides that may also produce a signal in the same region of a spectra. Removal of un-extended oligonucleotides would also increase the regions of the spectra available for detecting a signal and increase the number of potentially useful oligonucleotides.

Distinguishable Labels, Detection and Release

As used herein, the terms "distinguishable labels" and "distinguishable tags" refer to types of labels or tags that can be distinguished from one another and used to identify the nucleic acid to which the tag is attached. A variety of types of labels and tags may be selected and used for multiplex methods provided herein. For example, oligonucleotides, amino acids, small organic molecules, light-emitting molecules, light-absorbing molecules, light-scattering molecules, luminescent molecules, isotopes, enzymes and the like may be used as distinguishable labels or tags. In certain embodiments, oligonucleotides, amino acids, and/or small molecule organic molecules of varying lengths, varying mass-to-charge ratios, varying electrophoretic mobility (e.g., capillary electrophoresis mobility) and/or varying mass also can be used as distinguishable labels or tags. Accordingly, a fluorophore, radioisotope, colormetric agent, light emitting agent, chemiluminescent agent, light scattering agent, and the like, may be used as a label. The choice of label may depend on the sensitivity required, ease of conjugation with a nucleic acid, stability requirements, and available instrumentation. The term "distinguishable feature," as used herein with respect to distinguishable labels and tags, refers to any feature of one label or tag that can be distinguished from another label or tag (e.g., mass and others described herein). In some embodiments a label is attached to a chain terminating reagent or a chain terminating nucleotide. In some embodiments, label composition of the distinguishable labels and tags can be selected and/or designed to result in optimal flight behavior in a mass spectrometer and to allow labels and tags to be distinguished at high multiplexing levels. In some embodiments, labels such as fluorescent labels are utilized with a method that achieves separation in space, such as an array, beads or capillary electrophoresis. In some embodiments the label is a fluorescent label or dye that is detected by electrophoresis or real time PCR.

Detectable labels include, but are not limited to, nucleotides (labeled or unlabelled), compomers, sugars, peptides, proteins, antibodies, chemical compounds, conducting polymers, binding moieties such as biotin, mass tags, iron oxide particles or beads, colorimetric agents, light emitting agents, chemiluminescent agents, light scattering agents, fluorescent tags, radioactive tags, charge tags (electrical or magnetic charge), volatile tags and hydrophobic tags, biomolecules (e.g., members of a binding pair antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) and the like, some of which are further described below. In some embodiments a probe may contain a signal-generating moiety that hybridizes to a target and alters the passage of the target nucleic acid through a nanopore, and can generate a signal when released from the target nucleic acid when it passes through the nanopore (e.g., alters the speed or time through a pore of known size).

The term "detection" of a label as used herein refers to identification of a label species. Any suitable detection device can be used to distinguish label species in a sample. Detection devices suitable for detecting mass distinguishable labels, include, without limitation, certain mass spectrometers and gel electrophoresis devices. Examples of mass spectrometry formats include, without limitation, Matrix-Assisted Laser Desorption/Ionization Time-of-Flight (MALDI-TOF) Mass Spectrometry (MS), MALDI orthogonal TOF MS (OTOF MS; two dimensional), Laser Desorption Mass Spectrometry (LDMS), Electrospray (ES) MS, Ion Cyclotron Resonance (ICR) MS, and Fourier Transform MS. Methods described herein are readily applicable to mass spectrometry formats in which analyte is volatized and ionized ("ionization MS," e.g., MALDI-TOF MS, LDMS, ESMS, linear TOF, OTOF). Orthogonal ion extraction MALDI-TOF and axial MALDI-TOF can give rise to relatively high resolution, and thereby, relatively high levels of multiplexing. Detection devices suitable for detecting light-emitting, light absorbing and/or light-scattering labels, include, without limitation, certain light detectors and photodetectors (e.g., for fluorescence, chemiluminescence, absorption, and/or light scattering labels).

The labeled extension products corresponding to the low-abundance (minor) and/or high-abundance (major) variants can be analyzed by a variety of methods including, but not limited to, mass spectrometry, MALDI-TOF mass spectrometry, fluorescence detection, DNA sequencing gel, capillary electrophoresis on an automated DNA sequencing machine, microchannel electrophoresis, and other methods of sequencing, mass spectrometry, time of flight mass spectrometry, quadrupole mass spectrometry, magnetic sector mass spectrometry, electric sector mass spectrometry infrared spectrometry, ultraviolet spectrometry, palentiostatic amperometry, measurement of current/electrochemical signal or by DNA hybridization techniques including Southern Blots, Slot Blots, Dot Blots, and DNA microarrays, wherein DNA fragments would be useful as both "probes" and "targets," ELISA, fluorimetry, Fluorescence Resonance Energy Transfer (FRET), SNP-IT, GeneChips, HuSNP, BeadArray, TaqMan assay, Invader assay, MassExtend®, or MassCleave® method.

The extension products corresponding to the high-abundance variants (major variants) and the low-abundance variants (minor variants) that are obtained by the methods provided herein can be detected by a variety of methods. For example, the extension primers (UEPs) and/or the chain terminating reagents may be labeled with any type of chemical group or moiety that allows for detection of a signal and/or quantification of the signal including, but not limited to, mass labels, radioactive molecules, fluorescent molecules, antibodies, antibody fragments, haptens, carbohydrates, biotin, derivatives of biotin, phosphorescent moieties, luminescent moieties, electrochemiluminescent moieties, moieties that generate an electrochemical signal upon oxidation or reduction, e.g., complexes of iron, ruthenium or osmium (see, for example, eSensor technology used by Genmark Diagnostics, Inc. e.g., as described in Peirce et al., J. Clin. Micribiol., 50(11):3458-3465 (2012)), chromatic moieties, and moieties having a detectable electron spin resonance, electrical capacitance, dielectric constant or electrical conductivity, or any combination of labels thereof.

In some embodiments, for methods used herein, an oligonucleotide species often is paired with a distinguishable detectable label species, such that the detection of a particular label or tag species directly identifies the presence of a particular target nucleic acid species in a particular composition. Accordingly, one distinguishable feature of a label species can be used, for example, to identify one target nucleic acid species in a composition, as that particular distinguishable feature corresponds to the particular target nucleic acid. Labels and tags may be attached to a nucleic acid (e.g., oligonucleotide) by any known methods and in any location (e.g., at the 5' of an oligonucleotide). Thus, reference to each particular label species as "specifically corresponding" to each particular target nucleic acid species, as used herein, refers to one label species being paired with one target nucleic acid species. When the presence of a label species is detected, then the presence of the target nucleic acid species associated with that label species thereby is detected, in certain embodiments.

The term "species," as used herein with reference to a distinguishable tag or label (collectively, "label"), refers to one label that is detectably distinguishable from another label. In certain embodiments, the number of label species, includes, but is not limited to, about 2 to about 10000 label species, about 2 to about 500,000 label species, about 2 to about 100,000, about 2 to about 50000, about 2 to about 10000, and about 2 to about 500 label species, or sometimes about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000 or 500000 label species.

The term "mass distinguishable label" as used herein refers to a label that is distinguished by mass as a feature. The distinguishable tag in some embodiments consists of nucleotides, and sometimes the tag is about 5 nucleotides to about 50 nucleotides in length. The distinguishable tag in certain embodiments is a nucleotide compomer, which sometimes is about 5 nucleotides to about 35 nucleotides in length. In some embodiments, the distinguishable tag is a peptide, which sometimes is about 5 amino acids to about 100 amino acids in length. The distinguishable tag in certain embodiments is a concatemer of organic molecule units. In some embodiments, the tag is a trityl molecule concatemer. In some embodiments a mass distinguishable label is a chain terminating nucleotide.

A variety of mass distinguishable labels can be selected and used, such as for example a compomer, amino acid and/or a concatemer. Different lengths and/or compositions of nucleotide strings (e.g., nucleic acids; compomers), amino acid strings (e.g., peptides; polypeptides; compomers) and/or concatemers can be distinguished by mass and be used as labels. Any number of units can be utilized in a mass distinguishable label, and upper and lower limits of such units depends in part on the mass window and resolution of the system used to detect and distinguish such labels. Thus, the length and composition of mass distinguishable labels can be selected based in part on the mass window and resolution of the detector used to detect and distinguish the labels.

The term "compomer" as used herein refers to the composition of a set of monomeric units and not the particular sequence of the monomeric units. For a nucleic acid, the term "compomer" refers to the base composition of the nucleic acid with the monomeric units being bases. The number of each type of base can be denoted by Bn (i.e.: AaCcGgTt, with A0C0G0T0 representing an "empty" compomer or a compomer containing no bases). A natural compomer is a compomer for which all component monomeric units (e.g., bases for nucleic acids and amino acids for polypeptides) are greater than or equal to zero. In certain embodiments, at least one of a, c, g or t equals 1 or more (e.g., A0C0G1T0, A1C0G1T0, A2C1G1T2, A3C2G1T5). For purposes of comparing sequences to determine sequence variations, in the methods provided herein, "unnatural" compomers containing negative numbers of monomeric units can be generated by an algorithm utilized to process data. For polypeptides, a compomer refers to the amino acid composition of a polypeptide fragment, with the number of each type of amino acid similarly denoted. A compomer species can correspond to multiple sequences. For example, the compomer A2G3 corresponds to the sequences AGGAG, GGGAA, AAGGG, GGAGA and others. In general, there is a unique compomer corresponding to a sequence, but more than one sequence can correspond to the same compomer. In certain embodiments, one compomer species is paired with (e.g., corresponds to) one target nucleic acid species, amplicon species and/or oligonucleotide species. Different compomer species have different base compositions, and distinguishable masses, in embodiments herein (e.g., A0C0G5T0 and A0C5G0T0 are different and mass-distinguishable compomer species). In some embodiments, a set of compomer species differ by base composition and have the same length. In certain embodiments, a set of compomer species differ by base compositions and length.

A nucleotide compomer used as a mass distinguishable label can be of any length for which all compomer species can be detectably distinguished, for example about 1 to 15, 5 to 20, 1 to 30, 5 to 35, 10 to 30, 15 to 30, 20 to 35, 25 to 35, 30 to 40, 35 to 45, 40 to 50, or 25 to 50, or sometimes about 55, 60, 65, 70, 75, 80, 85, 90, 85 or 100, nucleotides in length. A peptide or polypeptide compomer used as a mass distinguishable label can be of any length for which all compomer species can be detectably distinguished, for example about 1 to 20, 10 to 30, 20 to 40, 30 to 50, 40 to 60, 50 to 70, 60 to 80, 70 to 90, or 80 to 100 amino acids in length. As noted above, the limit to the number of units in a compomer often is limited by the mass window and resolution of the detection method used to distinguish the compomer species.

The terms "concatemer" and "concatemer" are used herein synonymously (collectively "concatemer"), and refer to a molecule that contains two or more units linked to one another (e.g., often linked in series; sometimes branched in certain embodiments). A concatemer sometimes is a nucleic acid and/or an artificial polymer in some embodiments. A concatemer can include the same type of units (e.g., a homoconcatemer) in some embodiments, and sometimes a concatemer can contain different types of units (e.g., a heteroconcatemer). A concatemer can contain any type of unit(s), including nucleotide units, amino acid units, small organic molecule units (e.g., trityl), particular nucleotide sequence units, particular amino acid sequence units, and the like. A homoconcatemer of three particular sequence units ABC is ABCABCABC, in an embodiment. A concatemer can contain any number of units so long as each concatemer species can be detectably distinguished from other species. For example, a trityl concatemer species can contain about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900 or 1000 trityl units, in some embodiments.

A distinguishable label can be released from a nucleic acid product (e.g., an extended oligonucleotide) in certain embodiments. The linkage between the distinguishable label and a nucleic acid can be of any type that can be transcribed and cleaved, cleaved and allow for detection of the released label or labels (e.g., U.S. patent application publication no. US20050287533A1, entitled "Target-Specific Compomers and Methods of Use," naming Ehrich et al.). Such linkages and methods for cleaving the linkages ("cleaving conditions") are known. In certain embodiments, a label can be separated from other portions of a molecule to which it is attached. In some embodiments, a label (e.g., a compomer) is cleaved from a larger string of nucleotides (e.g., extended oligonucleotides). Non-limiting examples of linkages include linkages that can be cleaved by a nuclease (e.g., ribonuclease, endonuclease); linkages that can be cleaved by a chemical; linkages that can be cleaved by physical treatment; and photocleavable linkers that can be cleaved by light (e.g., o-nitrobenzyl, 6-nitroveratryloxycarbonyl, 2-nitrobenzyl group). Photocleavable linkers provide an advantage when using a detection system that emits light (e.g., matrix-assisted laser desorption ionization (MALDI) mass spectrometry involves the laser emission of light), as cleavage and detection are combined and occur in a single step.

In certain embodiments, a label can be part of a larger unit, and can be separated from that unit prior to detection. For example, in certain embodiments, a label is a set of contiguous nucleotides in a larger nucleotide sequence, and the label is cleaved from the larger nucleotide sequence. In such embodiments, the label often is located at one terminus of the nucleotide sequence or the nucleic acid in which it resides. In some embodiments, the label, or a precursor thereof, resides in a transcription cassette that includes a promoter sequence operatively linked with the precursor sequence that encodes the label. In the latter embodiments, the promoter sometimes is a RNA polymerase-recruiting promoter that generates an RNA that includes or consists of the label. An RNA that includes a label can be cleaved to release the label prior to detection (e.g., with an RNase).

Multiplexing

Methods provided herein allow for high-throughput detection and quantification of target nucleic acid species in a plurality of target nucleic acid species and their high-abundance and low-abundance variants. Multiplexing refers to the simultaneous detection of more than one target nucleic acid species. General methods for performing multiplexed reactions in conjunction with mass spectrometry, are known (see, e.g., U.S. Pat. Nos. 6,043,031, 5,547,835 and International PCT application No. WO 97/37041). Multiplexing provides an advantage that a plurality of target nucleic acid species and variants thereof (e.g., some having different sequence variations) can be identified in as few as a single mass spectrum, as compared to having to perform a separate mass spectrometry analysis for each individual target nucleic acid species. Methods provided herein lend themselves to high-throughput, highly-automated processes for analyzing sequence variations with high speed and accuracy, in some embodiments. In some embodiments, methods herein may be multiplexed at high levels in a single reaction. Multiplexing is applicable when the genotype at a polymorphic locus is not known, and in some embodiments, the genotype at a locus is known. In some embodiments, multiplexing utilizes described detection methods other than mass spectrometry.

In certain embodiments, the number of target nucleic acid species multiplexed include, without limitation, about 2 to about 1,000 species, about 2 to about 500 species, about 2 to about 100 species and sometimes about 1-3, 3-5, 5-7, 7-9, 9-11, 11-13, 13-15, 15-17, 17-19, 19-21, 21-23, 23-25, 25-27, 27-29, 29-31, 31-33, 33-35, 35-37, 37-39, 39-41, 41-43, 43-45, 45-47, 47-49, 49-51, 51-53, 53-55, 55-57, 57-59, 59-61, 61-63, 63-65, 65-67, 67-69, 69-71, 71-73, 73-75, 75-77, 77-79, 79-81, 81-83, 83-85, 85-87, 87-89, 89-91, 91-93, 93-95, 95-97, 97-101, 101-103, 103-105, 105-107, 107-109, 109-111, 111-113, 113-115, 115-117, 117-119, 121-123, 123-125, 125-127, 127-129, 129-131, 131-133, 133-135, 135-137, 137-139, 139-141, 141-143, 143-145, 145-147, 147-149, 149-151, 151-153, 153-155, 155-157, 157-159, 159-161, 161-163, 163-165, 165-167, 167-169, 169-171, 171-173, 173-175, 175-177, 177-179, 179-181, 181-183, 183-185, 185-187, 187-189, 189-191, 191-193, 193-195, 195-197, 197-199, 199-201, 201-203, 203-205, 205-207, 207-209, 209-211, 211-213, 213-215, 215-217, 217-219, 219-221, 221-223, 223-225, 225-227, 227-229, 229-231, 231-233, 233-235, 235-237, 237-239, 239-241, 241-243, 243-245, 245-247, 247-249, 249-251, 251-253, 253-255, 255-257, 257-259, 259-261, 261-263, 263-265, 265-267, 267-269, 269-271, 271-273, 273-275, 275-277, 277-279, 279-281, 281-283, 283-285, 285-287, 287-289, 289-291, 291-293, 293-295, 295-297, 297-299, 299-301, 301-303, 303-305, 305-307, 307-309, 309-311, 311-313, 313-315, 315-317, 317-319, 319-321, 321-323, 323-325, 325-327, 327-329, 329-331, 331-333, 333-335, 335-337, 337-339, 339-341, 341-343, 343-345, 345-347, 347-349, 349-351, 351-353, 353-355, 355-357, 357-359, 359-361, 361-363, 363-365, 365-367, 367-369, 369-371, 371-373, 373-375, 375-377, 377-379, 379-381, 381-383, 383-385, 385-387, 387-389, 389-391, 391-393, 393-395, 395-397, 397-401, 401-403, 403-405, 405-407, 407-409, 409-411, 411-413, 413-415, 415-417, 417-419, 419-421, 421-423, 423-425, 425-427, 427-429, 429-431, 431-433, 433-435, 435-437, 437-439, 439-441, 441-443, 443-445, 445-447, 447-449, 449-451, 451-453, 453-455, 455-457, 457-459, 459-461, 461-463, 463-465, 465-467, 467-469, 469-471, 471-473, 473-475, 475-477, 477-479, 479-481, 481-483, 483-485, 485-487, 487-489, 489-491, 491-493, 493-495, 495-497, 497-501 species or more.

Design methods for achieving resolved mass spectra with multiplexed assays can include primer and oligonucleotide design methods and reaction design methods. For primer and oligonucleotide design in multiplexed assays, the same general guidelines for primer design applies for uniplexed reactions, such as avoiding false priming and primer dimers, only more primers are involved for multiplex reactions. In addition, analyte peaks in the mass spectra for one assay are sufficiently resolved from a product of any assay with which that assay is multiplexed, including pausing peaks and any other by-product peaks. Also, analyte peaks optimally fall within a user-specified mass window, for example, within a range of 5,000-8,500 Da. Extension oligonucleotides can be designed with respect to target sequences of a given SNP strand, in some embodiments. In such embodiments, the length often is between limits that can be, for example, user-specified (e.g., 17 to 24 bases or 17 to 26 bases) and often do not contain bases that are uncertain in the target sequence. Hybridization strength sometimes is gauged by calculating the sequence-dependent melting (or hybridization/dissociation) temperature, Tm. A particular primer choice may be disallowed, or penalized relative to other choices of primers, because of its hairpin potential, false priming potential, primer-dimer potential, low complexity regions, and problematic subsequences such as GGGG. Methods and software for designing extension oligonucleotides (e.g., according to these criteria) are known, and include, for example, SpectroDESIGNER (Sequenom).

In some embodiments multiplex assays provided herein are designed to detect a low-abundance variant that represents about 0.1% to about 5% of a target nucleic acid species (ultra-high sensitivity assay). In some embodiments, multiplex assays provided herein are designed for single base extension and the plurality of target nucleic acid species included in the same plex have a common low-abundance variant. In some embodiments, only a chain terminating reagent specific for extending the common low-abundance variant of the plurality of target nucleic acid species is provided in the assay. No chain terminating reagents specific for extending the high-abundance variant of the plurality of target nucleic acid species is provided in the assay. Assays can be designed in part utilizing the following criteria:

a. An oligonucleotide species hybridizes to amplicons derived from the low-abundance variant and the high-abundance variant of a target nucleic acid species at a position 5' to a single base position that differs between the low-abundance variant and the high-abundance variant of the target nucleic acid species.

b. The nucleotide at the single base position is the same or different for each of the high-abundance variants of the plurality of target nucleic acid species in the plex.

c. The nucleotide at the single base position is the same for each of the low-abundance variants of the plurality of target nucleic acid species in the plex (i.e., all assays in a plex have the same low abundance or mutant base in common).

d. The nucleotide(s) at the single base position for the high-abundance variants of the plurality of target nucleic acid species are not the same as the nucleotide at the single base position for the low-abundance variants of the plurality of target nucleic acid species in the plex.

In some embodiments the multiplex assays are based on using a single chain terminating reagent or chain terminating nucleotide specific for extending the low-abundance variants of the target nucleic acid species included in a single plex and also include zero, one, two or three terminating nucleotides specific for extending the high-abundance variants of the target nucleic acid species in the assay. For example, four mutiplex assays (plexes) are designed with each plex targeting a different low-abundance variant. Target nucleic acid species that have the same low-abundance variant are combined in a single plex.

Multiplex C
Low-abundance variant—C
Possible high-abundance variants—none or G, A, T
Multiplex A
Low-abundance variant A
Possible high-abundance variants—none or G, C, T
Multiplex T
Low-abundance variant T
Possible high-abundance variants—none or G, A, C
Multiplex G
Low-abundance variant G
Possible high-abundance variants—none or C, A, T In some embodiments, the concentration of the one, two or three chain terminating reagents specific for the one or more high-abundance variants are each at a concentration of from about 0.01% to about 30% relative to the concentration of the chain terminating reagent specific for the low-abundance variants.

In some embodiments multiplex assays provided herein are designed to detect a low-abundance variant that represents about 1% to about 10% of a target nucleic acid species (high-sensitivity assays). In some embodiments, multiplex assays provided herein are designed for single base extension and the target nucleic acid species included in the same plex have a common high-abundance variant. Assays can be designed in part utilizing the following criteria:
  a. An oligonucleotide species hybridizes to amplicons derived from the low-abundance variant and the high-abundance variant of a target nucleic acid species at a position 5' to a single base position that differs between the low-abundance variant and the high-abundance variant of the target nucleic acid species.
  b. The nucleotide at the single base position is the same for each of the high-abundance variants of the plurality of target nucleic acid species in the plex (i.e., all assays in a plex have the same high-abundance base in common).
  c. The nucleotide at the single base position is the same or different for each of the low-abundance variants of the plurality of target nucleic acid species in the plex.
  d. The nucleotide(s) at the single base position for the low-abundance variants of the plurality of target nucleic acid species are not the same as the nucleotide at the single base position for the high-abundance variants of the plurality of target nucleic acid species in the plex.

In some embodiments, the multiplex assays are based on using a single chain terminating reagent or chain terminating nucleotide specific for extending the high-abundance variants of the target nucleic acid species included in a single plex. The multiplex assays can include one, two or three terminating nucleotides specific for extending the low-abundance variants of the target nucleic acid species in the assay. For example, four multiplex assays (plexes) are designed with each plex targeting a different high-abundance variant. Target nucleic acid species that have the same high-abundance variant are combined in a single plex.

Multiplex C
High-abundance variant—C
Possible low-abundance variants—G, A, T
Multiplex A
High-abundance variant A
Possible low-abundance variants—G, C, T
Multiplex T
High-abundance variant T
Possible low-abundance variants—G, A, C
Multiplex G
High-abundance variant G
Possible low-abundance variants—C, A, T In some embodiments, the concentration of the chain terminating reagent specific for the high-abundance variants is at a concentration of from about 0.01% to about 30% relative to the concentration of the one, two or three chain terminating reagents specific for the low-abundance variants.

In some embodiments multiplex assays provided herein are designed to detect a low-abundance variant that represents at least 10% of a target nucleic acid species (genotyping assay). In some embodiments, multiplex assays provided herein are designed for single base extension and the target nucleic acid species included in the same plex are not determined based on the relative abundance of the variants. Assays can be designed in part utilizing the following criteria:
  a. An oligonucleotide species hybridizes to amplicons derived from a target nucleic acid species at a position 5' to a single base position that differs between variants of the target nucleic acid species. The variants are present at approximately the same abundance (e.g., no high-abundance or low-abundance-variants).
  b. The nucleotide at the single base position is the same or different for each of the variants of the plurality of target nucleic acid species in the plex.

In some embodiments the multiplex assays are based on using chain terminating reagents or chain terminating nucleotides for extension that are not restricted based on the variant of the target nucleic acid species included in a single plex. The multiplex assays can include one, two, three or four terminating nucleotides in an assay.

In some embodiments, the concentration of the chain terminating reagents are approximately equimolar.

As used herein, the term "call rate" or "calling rate" refers to the number of calls (e.g., genotypes determined) obtained relative to the number of calls attempted to be obtained. In other words, for a 12-plex reaction, if 10 genotypes are ultimately determined from conducting methods provided herein, then 10 calls have been obtained with a call rate of 10/12. Different events can lead to failure of a particular attempted assay, and lead to a call rate lower than 100%. Occasionally, in the case of a mix of dNTPs and ddNTPs for termination, inappropriate extension products can occur by pausing of a polymerase after incorporation of one non-terminating nucleotide (i.e., dNTP), resulting in a prematurely terminated extension primer, for example. The mass difference between this falsely terminated and a correctly terminated primer mass extension reaction at the polymorphic site sometimes is too small to resolve consistently and can lead to miscalls if an inappropriate termination mix is used. The mass differences between a correct termination and a false termination (i.e., one caused by pausing) as well between a correct termination and salt adducts as well as a correct termination and an unspecific incorporation often is maximized to reduce the number of miscalls.

Multiplex assay accuracy may be determined by assessing the number of calls obtained (e.g., correctly or accurately assessed) and/or the number of false positive and/or false negative events in one or more assays. Accuracy also may be assessed by comparison with the accuracy of corresponding uniplex assays for each of the targets assessed in the multiplex assay. In certain embodiments, one or more methods may be used to determine a call rate. For example, a manual method may be utilized in conjunction with an automated or computer method for making calls, and in some embodiments, the rates for each method may be summed to calculate an overall call rate. In certain embodiments, accuracy or call rates, when multiplexing two or more target nucleic acid species (e.g., fifty or more target nucleic acids), can be about 99% or greater, 98%, 97%, 96%, 95%, 94%, 93%, 92%, 91%, 90%, 89%, 87-88%, 85-86%, 83-84%, 81-82%, 80%, 78-79% or 76-77%, for example. In some embodiments, a call rate for each target species in a multiplex assay that includes about 2 to 200 target species is greater than or equal to 80% or more (e.g., 81%, 82%, 83%, 84%, 85%, 86%, 87%, 88%, 89%, 90%, 91%, 92%, 93%, 94%, 95%, 96%, 97%, 98%, 99% or greater).

In certain embodiments the error rate may be determined based on the call rate or rate of accuracy. For example, the error rate may be the number of calls made in error. In some embodiments, for example, the error rate may be 100% less the call rate or rate of accuracy. The error rate may also be referred to as the "fail rate." Identification of false positives and/or false negatives can readjust both the call and error rates. In certain embodiments running more assays can also help in identifying false positives and/or false negatives, thereby adjusting the call and/or error rates. In certain embodiments, error rates, when multiplexing two or more target nucleic acid species (e.g., fifty or more target nucleic acids), can be about 1% or less, 2%, 3%, 4,%, 5%, 6%, 7%, 8%, 9%, 10%, 11%, 12%, 13%, 14%, 15%, 16%, 17%, 18%, 19%, 20%, 21%, 22%, 23%, 24% or 25%, for example.

Kits

In some embodiments, provided are kits for carrying out methods described herein. Kits often comprise one or more containers that contain one or more components described herein. A kit comprises one or more components in any number of separate containers, packets, tubes, vials, multi-well plates and the like, or components may be combined in various combinations in such containers. One or more of the following components, for example, may be included in a kit: (i) one or more nucleotides (e.g., terminating nucleotides and/or non-terminating nucleotides); one or more of which can include a detection label; (ii) one or more oligonucleotides, one or more of which can include a detection label (e.g., amplification primers, one or more extension primers (UEPs), oligonucleotides comprising a tag); (iii) one or more enzymes (e.g., a polymerase, endonuclease, restriction enzyme, exonuclease etc.); (v) controls components (e.g. control genomic DNA, primers, synthetic templates, target nucleic acids, etc.) (vi) one or more buffers and (vii) printed matter (e.g. directions, labels, etc). In some embodiments of the kits described herein, the relative amounts of terminating nucleotides are present in solution or are present in relative amounts such that upon dissolution according to the directions provided, the concentration of the chain terminating nucleotide specific for a high-abundance variant is less than the concentration of chain terminating nucleotide(s) specific for a low-abundance variant. In some embodiments, the concentration of the chain terminating reagents specific for high-abundance variant or variants are less than about 30% of the concentration of chain terminating reagent or reagents specific for the low-abundance variant or variants, less than about 20%, about 0.01% to about 30%, about 0.3% to about 30%, about 1% to about 20%, about 0.5% to less than about 20%, about 0.5% to less than about 15%, about 1% to about 15%, about 1% to about 10%, about 2% to about 10% or about 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10%. In certain embodiments, concentration of chain terminating reagents specific for high-abundance variants is between about 0.1% to about 10% of the concentration of chain terminating reagents specific for low-abundance variants, between about 0.01% to about 10% or about 0.01%, 0.05%, 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10%.

A kit sometimes is utilized in conjunction with a process, and can include instructions for performing one or more processes and/or a description of one or more compositions. A kit may be utilized to carry out a process described herein. Instructions and/or descriptions may be in tangible form (e.g., paper and the like) or electronic form (e.g., computer readable file on a tangle medium (e.g., compact disc) and the like) and may be included in a kit insert. A kit also may include a written description of an internet location that provides such instructions or descriptions.

In certain embodiments a kit comprises an enzyme having 3' to 5' exonuclease activity; and one or more chain terminating reagents that inhibit the activity of the enzyme on an oligonucleotide when the chain terminating reagent is at the 3' terminus of the oligonucleotide. In certain embodiments a kit comprises an enzyme specific for single-stranded DNA, having 3' to 5' exonuclease activity. In some embodiments the enzyme is from *Thermus thermophilus*. In some embodiments, the enzyme is TTHB178. In some embodiments the enzyme is provided in a buffer with a glycerol concentration of less than 50%. In some embodiments the enzyme is provided in a buffer without glycerol. In some embodiments the enzyme is in a 10% glycerol Tris buffer, or a Tris buffer without glycerol. In certain embodiments the one or more chain terminating reagents consist of one chain terminating reagent. In certain embodiments the one or more chain terminating reagents consist of two chain terminating reagents. In certain embodiments the one or more chain terminating reagents consist of three chain terminating reagents. In certain embodiments the one or more chain terminating reagents consist of four chain terminating reagents.

In certain embodiments the chain terminating reagent is is a chain terminating nucleotide. In certain embodiments the chain terminating nucleotide is modified at a 3' position of a pentose sugar moiety of the chain terminating nucleotide. In certain embodiments the chain terminating reagent is a dideoxynucleotide. In certain embodiments the dideoxynucleotide is selected from ddATP, ddGTP, ddCTP, ddTTP and ddUTP. In certain embodiments the chain terminating reagent is an acyclic nucleotide. In certain embodiments the acyclic nucleotide is selected from acyATP, acyCTP, acyGTP, acyTTP and acy-Bromo-UTP. In certain embodiments the chain terminating reagent comprises a mass-distinguishable tag.

In certain embodiments a kit includes one or more of: oligonucleotides, a polymerase, alkaline phosphatase, one or more buffers and one or more reaction controls.

In certain embodiments, a kit comprises one, two or three chain terminating reagents that are specific for detection of a plurality of high-abundance variants and a chain terminating reagent that is specific for detection of a plurality of low-abundance variants and the concentration of each of the one, two or three chain terminating reagents specific for detection of a high-abundance variant is about 0.3% to about 30% of the concentration of the chain terminating reagent that is specific for the low-abundance variants. In certain embodiments, the chain terminating reagent that is specific for detection of a plurality of low-abundance variants and the one, two or three chain terminating reagents that are specific for detection of a plurality of high-abundance variants are in a single container. In some embodiments, a kit comprises two or more containers each of which hold a different chain terminating reagent that is specific for detection of a plurality of low-abundance variants and one, two or three chain terminating reagents specific for detection of a plurality of high-abundance variants In certain embodiments a kit comprises one, two or three chain terminating reagents that are specific for detection of a plurality of low-abundance variants and a chain terminating reagent specific for detection of a plurality of high-abundance variants and the concentration of the chain terminating reagent specific for the high-abundance variants is about 0.3% to about 30% of the concentration of each of the one, two or three chain terminating reagents specific for the low-abundance variants. In certain embodiments, the chain terminating reagent that is specific for detection of a plurality of high-abundance variants and the one, two or three chain terminating reagents that are specific for detection of a plurality of low-abundance variants are in a single container. In some embodiments, a kit comprises two or more containers each of which hold a different chain terminating reagent that is specific for detection of a plurality of high-abundance variants and one, two or three chain terminating reagents specific for detection of a plurality of low-abundance variants.

In certain embodiments a kit comprises two, three or four chain terminating reagents at equivalent concentrations.

EXAMPLES

The examples set forth below illustrate certain embodiments and do not limit the technology.

Example 1: Exonuclease Reaction with Chop Block Reagent

The conditioning with an 3' to 5' exonuclease (Chop Block step) can be applied to a single base extension reaction and to various embodiments of a single base extension reaction, including, but not limited to, multiplex genotyping reactions, multiplex high sensitivity reactions for minor variants, and multiplex ultra-high sensitivity reactions for very minor variants. These three biochemistries utilize a standard multiplex PCR to interrogate genomic variations of interest. After PCR, for all three biochemistries, the amplified product is treated with shrimp alkaline phosphatase for dephosphorylating remaining deoxynucleotides. For all three biochemistries, SAP treated amplified products are then probed in a single base extension reaction. The differences between these biochemistries in the single base extension reaction are the number, amount and type of chain terminating nucleotide used. The single base extension reaction is 9 ul for each chemistry and the entire 9 ul is conditioned with the Chop Block reagent as shown in Table 1.

TABLE 1

| Chop Block reaction components | | | |
| --- | --- | --- | --- |
| Reagent | Reagent Concentration | Per Rxn Concentration | Per Rxn Volume |
| Water | N/A | N/A | 0.6 |
| Buffer* | 10× | 1× | 1.2 |
| Chop Block | (30 uM-200 uM) | 3 uM-20 uM | 1.2 |
| Extension Reaction Analyte | N/A | N/A | 9 |
| | | Total | 12 |

*The 10x buffer composition is: 20 mM Hepes, 100 mM KCl, and 5 mM MgCl2**, pH 7.5
**MnCl2 is a potential alternative co-factor The entire reaction is incubated at 60° C. for 30 minutes with a subsequent denaturing/deactivation step at 85° C. for 10 minutes. After the Chop Block reaction, 38 µl of a Tween-20 solution at 28 µM is added for a final 50 µl total volume. The Chop Block conditioned analyte is then further conditioned with ion exchange resin to remove salt and dispensed onto matrix arrayed on a silica chip. The reactions are dispensed onto a 96-well SpectroCHIP (F-chip) using the CPM (Chip Prep Module), by adding 20 ml of resin at 400 pressed out volume (setting on the CPM associated with dispensing of the analyte onto the SpectroCHIP that relates to the size of the pendant drop of analyte presented at the end of the CPM dispensing pipette tip). The chip is then analyzed via Maldi-TOF Mass Spectrometry using the MassARRAY 4.

The Chop Block reaction was tested in various iPLEX-USK (Ultraseek) PCR/SAP/Extend reactions for the ability to detect an EGFR Exon 19 deletion mutant at 1% occurrence (EGFR_Exon19del_2236 @ 1%), using Chop Block enzyme final concentrations in a 12 µl volume of between 0.034 µg/µl to 0.150 µg/µl (0.034, 0.072, 0.080, 0.089, 0.098, 0.109, 0.122, 0.135 and 0.150 µg/µl). It was found that all the tested concentrations were statistically equivalent in the sensitivity of mutant peak detection. In addition, a range of final volumes of sample (after the addition of Tween-20, post Chop Block reaction) were tested for the sensitivity of detection. Final volumes of between 25 µl to 50 µl (25, 30, 35, 40, 45 and 50 µl) were tested and found to be statistically equivalent in the sensitivity of detection of the mutant.

Example 2: Ultra-High Sensitivity Assay (UltraSEEK™) w Chop Block Reagent

Figure 3:
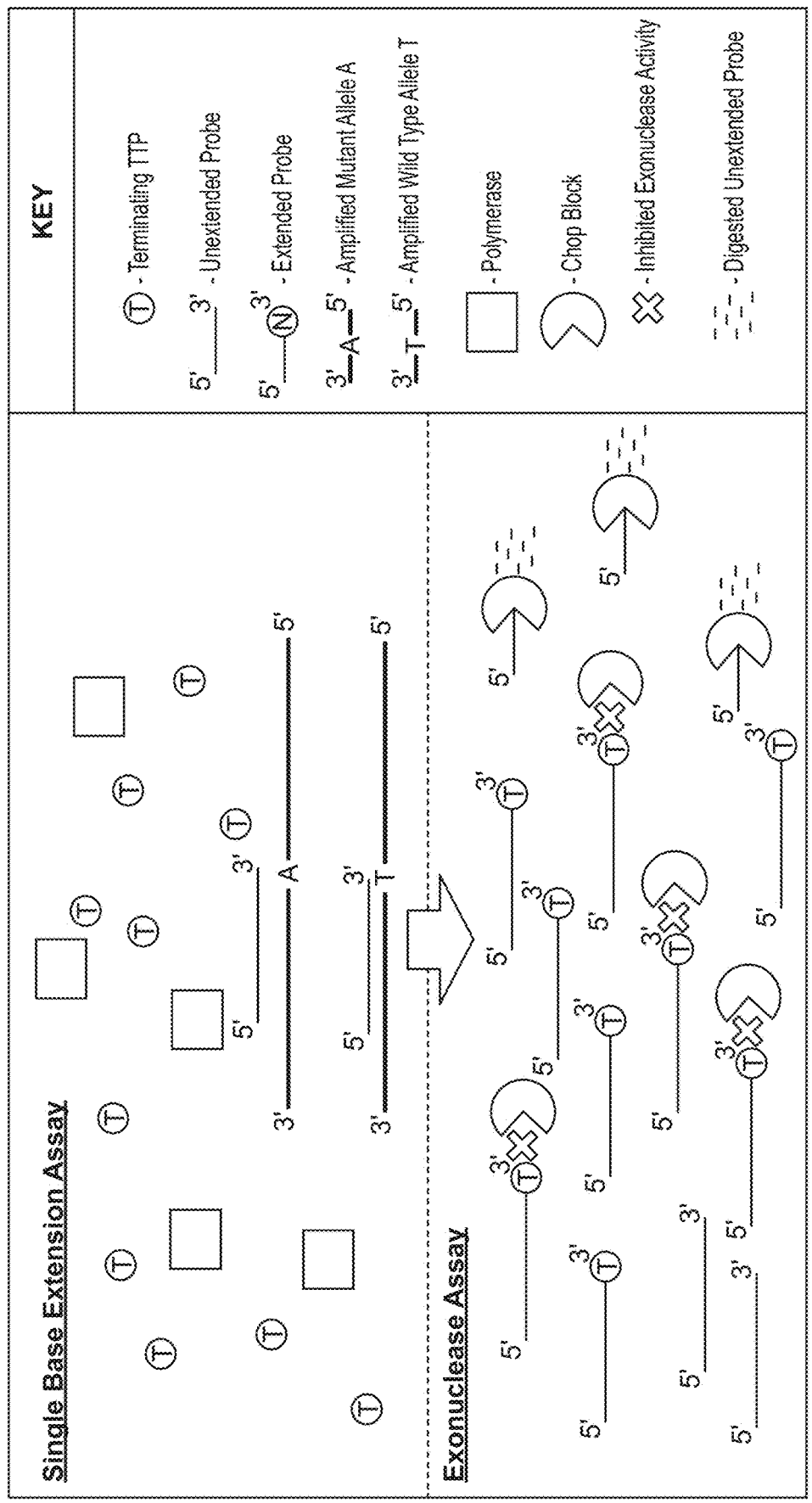
FIG. 3 is a schematic showing a single base extension ultra-high sensitivity assay with an exonuclease reagent (Chop Block reagent).

FIG. 3 is a schematic of an embodiment of an ultra-high sensitivity assay using only a single chain terminating reagent (e.g., terminating TTP) specific for extending a probe bound to a low-abundance variant (see upper panel, single base extension assay). For simplicity, the figure shows a single nucleic acid species with two variants. In a multiplex assay there would be a plurality of nucleic acid species each having two variants. Probes bound to the low-abundance variants of the plurality of species would be extended by the single chain terminating reagent (e.g., terminating TTP). In the lower panel (exonuclease assay) the extended probes (representing only the low-abundance variants) are protected from digestion by the Chop Block enzyme, while the unextended probes are not. For this particular example, the materials and protocols are based on Agena Bioscience's UtraSEEK™ assay.

One of ordinary skill in the art will recognize that an assay can be directed to different targets and/or utilize different reagents with minor adjustments to the protocol.

In an alternative embodiment, not shown, an ultra-high sensitivity assay can have a single chain terminating reagent specific for low-abundance variants and one two or three chain terminating reagents specific for high-abundance variants (each at a lower concentration than the concentration of the chain terminating reagent specific for low abundance variants).

Multiplex PCR

Multiplex PCR reactions targeting variants KRAS G12S, KRAS G12C, and PIK3CA E542K and Albumin were prepared in a final volume of 25 uL [Genomic DNA mix with each variant (Albumin excepted) in the mix at 1% allelic frequency in a background of 33 ng (Mutant DNA—Horizon Diagnostics, wild type background—Cordell Institute)]. In addition to the DNA, reaction conditions utilized 1×PCR buffer (Agena Bioscience), 100 nmol/L of each primer, 125 µmol/L of each of the 4 deoxynucleotide triphosphates (Agena Bioscience), 1.5U of Taq Polymerase (Agena Bioscience), & 1 mmol/L supplemental $MgCl_2$ (Agena Bioscience). The primer sequences are listed in Table 2. The reaction was performed in an ABI 9700 PCR system (Applied Biosystems). PCR protocol included an initial denaturation step at 95° C. for 2 min followed by 45 cycles of denaturation at 95° C. for 30 s, annealing at 60° C. for 30 s, and elongation at 72° C. for 1 min.

TABLE 2

Multiplex PCR Primers

| PCR Primer | Sequence |
|---|---|
| KRAS G12S Forward (SEQ ID NO: 1) | 5'-ACGTTGGATGAAGGCCTGCTGAAAA TGACT-3' |
| KRAS G12S Forward (SEQ ID NO: 2) | 5'-ACGTTGGATGTTGTTGGATCATATT CGTCCAC-3' |
| KRAS G12C Forward (SEQ ID NO: 1) | 5'-ACGTTGGATGAAGGCCTGCTGAAAA TGACT-3' |
| KRAS G12C Reverse (SEQ ID NO: 2) | 5'-ACGTTGGATGTTGTTGGATCATATT CGTCCAC-3' |
| PIK3CA E542K Forward (SEQ ID NO: 3) | 5'ACGTTGGATGGCTAGAGACAATGAAT TAAGGGAAA-3' |
| PIK3CA E542K Reverse (SEQ ID NO: 4) | 5'ACGTTGGATGAAGAAAAAGAAACAGA GAATCTCCA-3' |
| Albumin_Forward) (PCR Control) (SEQ ID NO: 5) | 5'-ACGTTGGATGCAAGCCCTGAAGCTC AACTC-3' |
| Albumin_Reverse (PCR Control) (SEQ ID NO: 6) | 5'-ACGTTGGATGGATTTGTGTGGGCAT GACAG-3' |

Shrimp Alkaline Phosphatase

Amplified DNA was treated with shrimp alkaline phosphatase (SAP) to dephosphorylate unincorporated nucleotides from the PCR reaction. Reaction conditions use 1×SAP buffer (Agena Bioscience), 0.5U of SAP, and 5 ul of the multiplex amplified product in a total volume of 7 ul. The reaction was performed in an ABI 9700 PCR system (Applied Biosystems). SAP protocol included 37° C. incubation for 40 min followed by a protein denaturing step at 85° C. for 5 minutes.

Extension Reaction

SAP treated amplified products were probed at specific residues in a single base extension reaction. Reaction conditions use 1× Buffer Plus (Agena Bioscience), 5.56 uM bio-ddUTP (Perkin Elmer), 0.625-1.25 uM probes (Albumin probe was at 62.5 nM), 0.14U iPLEX® Pro enzyme (Agena Bioscience), and 7 ul of SAP treated amplified product in a total reaction volume of 9 ul. The probe sequences are listed in Table 3. The reaction was performed in an ABI 9700 PCR system (Applied Biosystems). Extension protocol included an initial denaturation step at 94° C. for 30 s, followed by 40 cycles of denaturation at 94° C. for 5 s, annealing at 52° C. for 5 s. Within the 40 cycles is another cycle between 52° C. annealing and 80° C. denaturing. Each step is 5 s and cycles 5× before continuing with the 40 main cycles. In this rationale, 200 cycles are explored (see Table 4 for cycling protocol).

TABLE 3

Extension Probes-/5Biosg/ = 5' Biotin; /3InvdT/ = 3' Inverted dT

| Probe | Sequence |
|---|---|
| KRAS_G12C_PlxT (SEQ ID NO: 7) | TTGTGGTAGTTGGAGCT |
| KRAS_G12S_PlxT (SEQ ID NO: 8) | CACTCTTGCCTACGCCAC |
| PIK3CA_E542K_PlxT (SEQ ID NO: 9) | CCTGCTCAGTGATTT |
| Albumin (PCR Control) (SEQ ID NO: 10) | GTTGCTGTCATCTCTTGTGGGC |
| Capture Control 1 (SEQ ID NO: 11) | /5Biosg/GTTGACTCGTGGT/3InvdT/ |
| Capture Control 2 (SEQ ID NO: 12) | /5Biosg/GTTGACTCTGTGGT/3InvdT/ |
| Capture Control 3 (SEQ ID NO: 13) | /5Biosg/GTTTGGGGCCAGACTCTGC CCGTTTGGT/3InvdT/ |
| Capture Control 4 (SEQ ID NO: 14) | /5Biosg/GTTTGGGGTCCAGACTCTG CCCGTTTGGT/3InvdT/ |
| Capture Control 5 (SEQ ID NO: 15) | /5Biosg/GAAGCCAGACTCTTCGTTT GG/3InvdT/ |

TABLE 4

Single Base Extension Cycling Protocol

| | | |
|---|---|---|
| 95° C. for 30 seconds | | |
| 95° C. for 5 seconds | | 40 cycles |
| 52° C. for 5 seconds | 5 cycles | |
| 80° C. for 5 seconds | | |
| 72° C. for 3 minutes | | |
| 4° C. for ∞ | | |

Chop Block

Extension reaction products were cleaned of unreacted probes in the Chop Block reaction. Reaction conditions use 1× Buffer (20 mM Hepes, 100 mM KCl, and 5 mM MgCl2, pH 7.5), 1.5 µg Chop Block, and 9 ul extension reaction products in a total volume of 12 µl. The chop block reaction was incubated in an ABI 9700 PCR system (Applied Biosystems). The reaction is incubated at 60° C. for 30 min and then the Chop Block protein is heat denatured at 85° C. for 10 min.

Sample Conditioning

Chop Block treated samples were diluted to 25 ul by adding 13 ul of water. Diluted samples were reacted with 5 µl anion exchange resin (Agena Bioscience) slurry that introduces about 3.5 mg of resin. The reaction was incubated at room temperature for 30 min on a rotating hematology mixer.

Sample Dispensing

Resin treated analyte were dispensed onto matrix elements arrayed on a silica chip using the Chip Prep Module (CPM—Agena Bioscience). Dispense volumes range between 80 to 120 nl. Calibrant analyte that consists of three distinct peaks are dispensed onto separate elements of the silica chip by the CPM.

Data Acquisition

Dispensed chip arrays were introduced to the Agena MassARRAY® instrument. The instrument is a Matrix Assisted Laser Desorption/Ionization Time-of-Flight (MALDI-TOF) mass spectrometer. Acquisition parameters include the following: shots (n)—30; Maximum Acquisitions—15; Minimum Good Spectra—15; Maximum Good Spectra—15. Mass spectra peaks are reported out as normalized intensity by reporting software. By normalizing, peaks across spectra can be compared. To create the normalized value, either peak signal to noise, area, or height is used. The normalization was done by dividing this value (SNR, area, or height) to the value at that mass on a linear fit of internal standards (Capture controls) in the spectra.

FIG. 8 shows a spectra of the products of a multiplex ultra-high sensitivity assay with Chop block reagent targeting KRAS G12S, KRAS G12C, and PIK3CA E542K and Albumin. Peaks labelled "c" are capture control peaks (used for normalization). Peak labelled "p" is a process control peak. Peak labelled "a" is the analyte peak (KRAS G12S positive mutation). There is only one analyte peak because there is only one variant in the sample. The other targets in the sample represent wild type, which are not extended and cannot result in a peak in the spectra.

Example 3: Ultra-High Sensitivity Assay with and without Chop Block Reagent

Multiplex PCR (Standard UltraSEEK™ & UltraSEEK™ w/Chop Block Reagent)

This example used a multiplex mutation standard covering six variants of differing allelic frequencies. Multiplex PCR reactions targeting variants ABL1 T315I, AIK F1174L, BRAF V600E, EGFR G719S, EGFR L861Q, EGFR T790M, KRAS G12D and Albumin were prepared in a final volume of 25 uL [Genomic DNA mix with each variant (Albumin excepted) in the mix at 2% allelic frequency in a background of 33 ng (Mutant DNA—Horizon Diagnostics, wild type background—Cordell Institute)]. In addition to the DNA, reaction conditions utilized 1×PCR buffer (Agena Bioscience), 100 nmol/L of each primer, 125 µmol/L of each of the 4 deoxynucleotide triphosphates (Agena Bioscience), 1.5U of Taq Polymerase (Agena Bioscience), & 1 mmol/L supplemental $MgCl_2$ (Agena Bioscience). The primer sequences are listed in Table 5. The reaction was performed in an ABI 9700 PCR system (Applied Biosystems). PCR protocol included an initial denaturation step at 95° C. for 2 min followed by 45 cycles of denaturation at 95° C. for 30 s, annealing at 60° C. for 30 s, and elongation at 72° C. for 1 min.

TABLE 5

Multiplex PCR Primers.

| PCR Primer | Sequence |
| --- | --- |
| ABL1_T315I_Forward (SEQ ID NO: 16) | 5'-ACGTTGGATGAGTCCTCGTTGT CTTGTTGG-3' |
| ABL1_T315I_Reverse (SEQ ID NO: 17) | 5'-ACGTTGGATGTCTGAGTGGCCA TGTACAGC-3' |
| ALK_F1174L_Forward (SEQ ID NO: 18) | 5'-ACGTTGGATGTTGGTTACATCC CTCTCTGC-3' |
| ALK_F1174L_Reverse (SEQ ID NO: 19) | 5'-ACGTTGGATGATTGCAGGCTCA CCCCAATG-3' |
| BRAF_V600E_Forward (SEQ ID NO: 20) | 5'-ACGTTGGATGTCTTCATGAAGA CCTCACAG-3' |
| BRAF_V600E_Reverse (SEQ ID NO: 21) | 5-ACGTTGGATGCCACAAAATGGAT CCAGACA-3' |
| EGFR_G719S_Forward (SEQ ID NO: 22) | 5'-ACGTTGGATGTGGAGCCTCTTA CACCCAGT-3' |
| EGFR_G719S_Reverse (SEQ ID NO: 23) | 5'-ACGTTGGATGGTGCCAGGGACC TTACCTTA-3' |
| EGFR_L861Q_Forward (SEQ ID NO: 24) | 5'-ACGTTGGATGAGCCAGGAACGT ACTGGTGA-3' |
| EGFR_L861Q_Reverse (SEQ ID NO: 25) | 5'-ACGTTGGATGCCTGGTGTCAGG AAAATGCT-3' |
| EGFR_T790M_Forward (SEQ ID NO: 26) | 5'-ACGTTGGATGCTCCAGGAAGCC TACGTGAT3' |
| EGFR_T790M_Reverse (SEQ ID NO: 27) | 5'-ACGTTGGATGGTCTTTGTGTTC CCGGACAT-3' |
| KRAS_G12D_Forward (SEQ ID NO: 1) | 5'-ACGTTGGATGAAGGCCTGCTGA AAATGACT-3' |
| KRAS_G12D_Reverse (SEQ ID NO: 2) | 5'-ACGTTGGATGTTGTTGGATCAT ATTCGTCCAC-3' |
| Albumin_Forward (PCR Control) (SEQ ID NO: 5) | 5'-ACGTTGGATGCAAGCCCTGAAG CTCAACTC-3' |
| Albumin_Reverse (PCR Control) (SEQ ID NO: 6) | 5'-ACGTTGGATGGATTTGTGTGGG CATGACAG-3' |

Shrimp Alkaline Phosphatase (Standard UltraSEEK™ & Chop Block)

Amplified DNA was treated with shrimp alkaline phosphatase (SAP) to dephosphorylate unincorporated nucleotides from the PCR reaction. Reaction conditions use 1×SAP buffer (Agena Bioscience), 0.5U of SAP, and 5 ul of the multiplex amplified product in a total volume of 7 ul. The reaction was performed in an ABI 9700 PCR system (Applied Biosystems). SAP protocol included 37° C. incubation for 40 min followed by a protein denaturing step at 85° C. for 5 minutes.

Extension Reaction (Standard UltraSEEK™)

SAP treated amplified products were probed at specific residues in a single base extension reaction. Reaction conditions use 1× Buffer Plus (Agena Bioscience), 5.56 uM bio-ddUTP (Perkin Elmer), 0.625-1.25 uM probes (Albumin probe was at 62.5 nM), 0.14U iPLEX® Pro enzyme (Agena Bioscience), and 7 ul of SAP treated amplified product in a total reaction volume of 9 ul. The probe sequences are listed in Table 6. The reaction was performed in an ABI 9700 PCR system (Applied Biosystems). Extension protocol included an initial denaturation step at 94° C. for 30 s, followed by 40 cycles of denaturation at 94° C. for 5 s, annealing at 52° C. for 5 s. Within the 40 cycles is another cycle between 52° C. annealing and 80° C. denaturing. Each step is 5 s and cycles 5× before continuing with the 40 main cycles. In this rationale, 200 cycles are explored (see Table 7 for cycling protocol).

Extension Reaction (Chop Block)

SAP treated amplified products were probed at specific residues in a single base extension reaction. Reaction conditions use 1× Buffer Plus (Agena Bioscience), 222 uM acylo-Bromo-U (New England Biolabs), 0.625-1.25 uM probes (Albumin probe was at 62.5 nM), 0.14U iPLEX® Pro enzyme (Agena Bioscience), and 7 ul of SAP treated amplified product in a total reaction volume of 9 ul. The probe sequences are listed in Table 6. The reaction was performed in an ABI 9700 PCR system (Applied Biosystems). Extension protocol included an initial denaturation step at 94° C. for 30 s, followed by 40 cycles of denaturation at 94° C. for 5 s, annealing at 52° C. for 5 s. Within the 40 cycles is another cycle between 52° C. annealing and 80° C. denaturing. Each step is 5 s and cycles 5× before continuing with the 40 main cycles. In this rationale, 200cycles are explored (see Table 7 for cycling protocol).

TABLE 6

Extension Probes-
/5Biosg/ = 5' Biotin; /3InvdT/ = 3' Inverted dT

| Probe | Sequence |
| --- | --- |
| ABL1 T315I (SEQ ID NO: 28) | GCCCCCGTTCTATATCATCA |
| ALK F1174L (SEQ ID NO: 29) | CCAATGTTCTGGTGGTT |
| BRAF V600E (SEQ ID NO: 30) | CCCACTCCATCGAGATTTC |
| EGFR G719S (SEQ ID NO: 31) | CGAACACACCGGAGC |
| EGFR L861Q (SEQ ID NO: 32) | TCTTCCGCACCCAGC |
| EGFR T790M (SEQ ID NO: 33) | CCGTGCAGCTCATCA |
| KRAS G12D (SEQ ID NO: 34) | CACTCTTGCCTACGCCA |
| Albumin (PCR Control) (SEQ ID NO: 10) | GTTGCTGTCATCTCTTGTGGGC |
| Capture Control 1 (SEQ ID NO: 11) | /5Biosg/GTTGACTCGTGGT/3InvdT/ |
| Capture Control 2 (SEQ ID NO: 12) | /5Biosg/GTTGACTCTGTGGT/3InvdT/ |
| Capture Control 3 (SEQ ID NO: 13) | /5Biosg/GTTTGGGGCCAGACTCTGCCCGTTTGGT/3InvdT/ |
| Capture Control 4 (SEQ ID NO: 14) | /5Biosg/GTTTGGGGTCCAGACTCTGCCCGTTTGGT/3InvdT/ |
| Capture Control 5 (SEQ ID NO: 15) | /5Biosg/GAAGCCAGACTCTTCGTTTGG/3InvdT/ |

TABLE 7

Single Base Extension Cycling Protocol

| | | |
| --- | --- | --- |
| 95° C. for 30 seconds | | |
| 95° C. for 5 seconds | | 40 cycles |
| 52° C. for 5 seconds | 5 cycles | |
| 80° C. for 5 seconds | | |
| 72° C. for 3 minutes | | |
| 4° C. for ∞ | | |

Standard UltraSEEK™ Bead Cleanup 4.25 ul/sample of 10 mg/ml Streptavidin-coated magnetic beads (Agena Bioscience) were conditioned in two rounds with 500 uL binding and wash buffer (Agena Bioscience) and then resuspended in the binding and wash buffer at a concentration of 1 mg/mL. A total volume of 41 mL of conditioned beads was added to each 9 ul extension reaction, and capture was performed at room temperature for 30 minutes under constant rotation in a hematology mixer. Beads with captured products were pelleted using a magnet, and the binding and wash solution was discarded. The beads were washed once with 100 mL of high-performance liquid chromatography-grade water, resuspended with 13 ul of elution solution (Agena Bioscience), and incubated at 95° C. for 5 minutes. Incubation was performed in an ABI PCR System 9700.

Chop Block Cleanup

Extension reaction products were cleaned of unreacted probes in the Chop Block reaction. Reaction conditions use 1× Buffer (Agena Bioscience, PCR Buffer), 1.5 µg Chop Block, and 9 ul extension reaction products in a total volume of 14 µl. The chop block reaction was incubated in an ABI 9700 PCR system (Applied Biosystems). The reaction was incubated at 60° C. for 30 min and then the Chop Block protein is heat denatured at 85° C. for 10 min.

Sample Conditioning

Standard UltraSEEK™ Bead treated, and Chop Block treated samples were reacted with 5 µl anion exchange resin (Agena) slurry that introduces about 3.5 mg of resin. The reaction was incubated at room temperature for 30 min on a rotating hematology mixer.

Sample Dispensing

Resin treated analyte was dispensed onto matrix elements arrayed on a silica chip using the rs1000 Nanodispenser (Agena Bioscience). Dispense volumes range between 12 to 20 nl. Calibrant analyte that consists of three distinct peaks are dispensed onto separate elements of the silica chip by the Nanodispenser.

Data Acquisition

Dispensed chip arrays were introduced to the Agena MassARRAY® instrument. The instrument is a Matrix Assisted Laser Desorption/Ionization Time-of-Flight (MALDI-TOF) mass spectrometer. Acquisition parameters include the following: shots (n)—30; Maximum Acquisitions—15; Minimum Good Spectra—15; Maximum Good Spectra—15. Mass spectra peaks are reported out as normalized intensity by reporting software. By normalizing, peaks across spectra can be compared. To create the normalized value, either peak signal to noise, area, or height is used. The normalization is done by deriving a peak ratio (dividing a mutant peak value (SNR, area, or height) by the wild-type peak value (SNR, area, or height)).

Figure 6A:
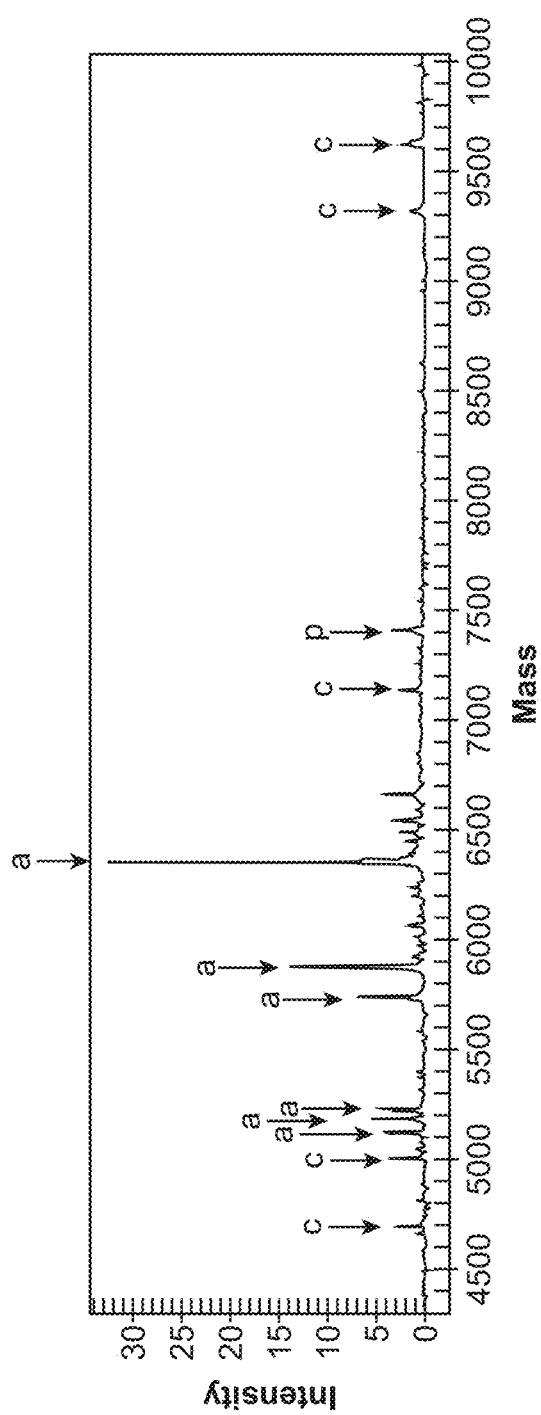
FIG. 6A and FIG. 6B show spectra of an ultra-high sensitivity assay (UltraSEEK™) with bead-based processing (6A) and processed with an endonuclease reagent (Chop Block reagent) (6B).
Figure 6B:
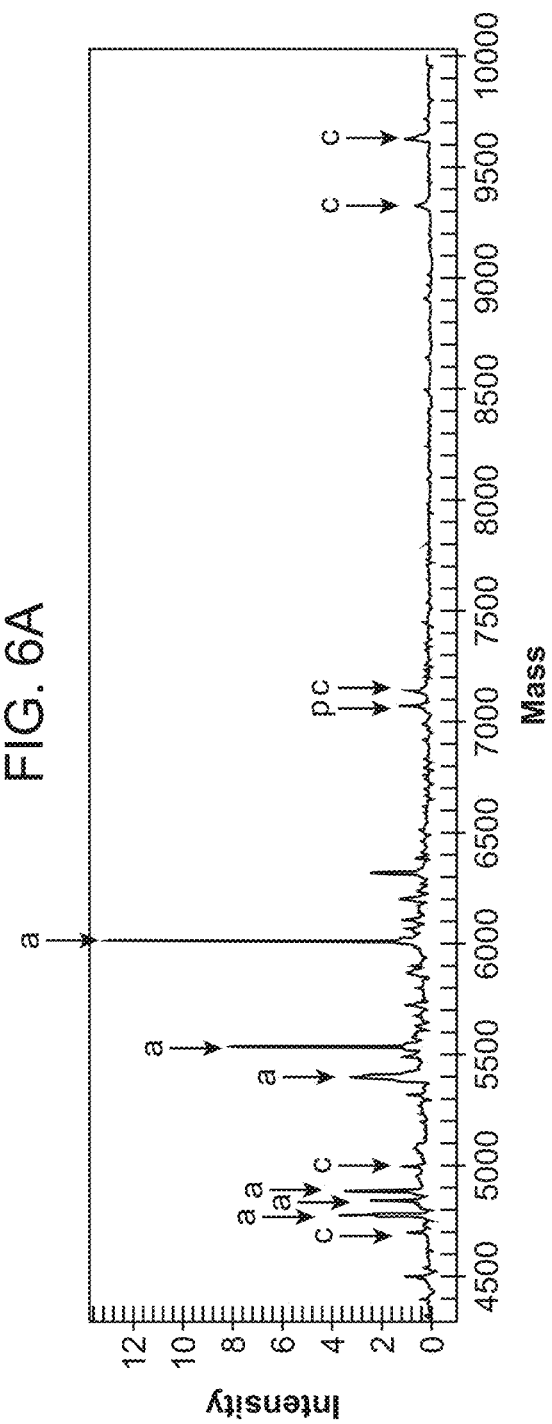

FIGS. 6A and 6B show spectra for Standard UltraSEEK™ (bead treated) assays and UltraSEEK™ assays w/Chop Block reagent, respectively. Peaks labeled "c" denote the capture control peaks, peaks labeled "p" denote the process control and the peaks labeled "a" denote peaks representing the extended oligonucleotides for low-abundance species peaks (positive mutants). In FIG. 6B (Chop Block Reaction) peaks labeled a are more pronounced over background noise than corresponding peaks labeled a in FIG. 6A (bead treated). Digesting un-extended oligonucleotides, which represent most of the oligonucleotides in the assay enables low-abundance species to become visible over noise. In standard UltraSEEK™ un-extended oligonucleotides are removed from a reaction by selectively capturing extended oligonucleotides and washing away the remaining reaction components, including the un-extended oligonucleotides. This process is both time consuming and requires manual pipetting steps with the chance of introducing manual error. Use of a Chop Block reagent may increase sensitivity, improves workflow and may reduce the chance of manual error.

A lower signal (intensity) is observed in the Chop Block assay spectra (FIG. 6B) compared to the bead treated spectra (FIG. 6A). However, the relative intensity as compared to capture controls does not change between the Chop Block and the standard bead assay (equivalent normalized intensities). Without being held to a theory, the observed lower signal may be the result of poor dispensing in the Chop Block assay due to the glycerol associated with the Chop Block enzyme when the enzyme is added to a reaction before dispensing onto a bioarray. In some embodiments, this problem is addressed by reducing the concentration of glycerol that the enzyme is stored in or eliminating glycerol completely.

Example 4: Parameters of Ultra-High Sensitivity Assay with Chop Block Reagent

Figure 4:
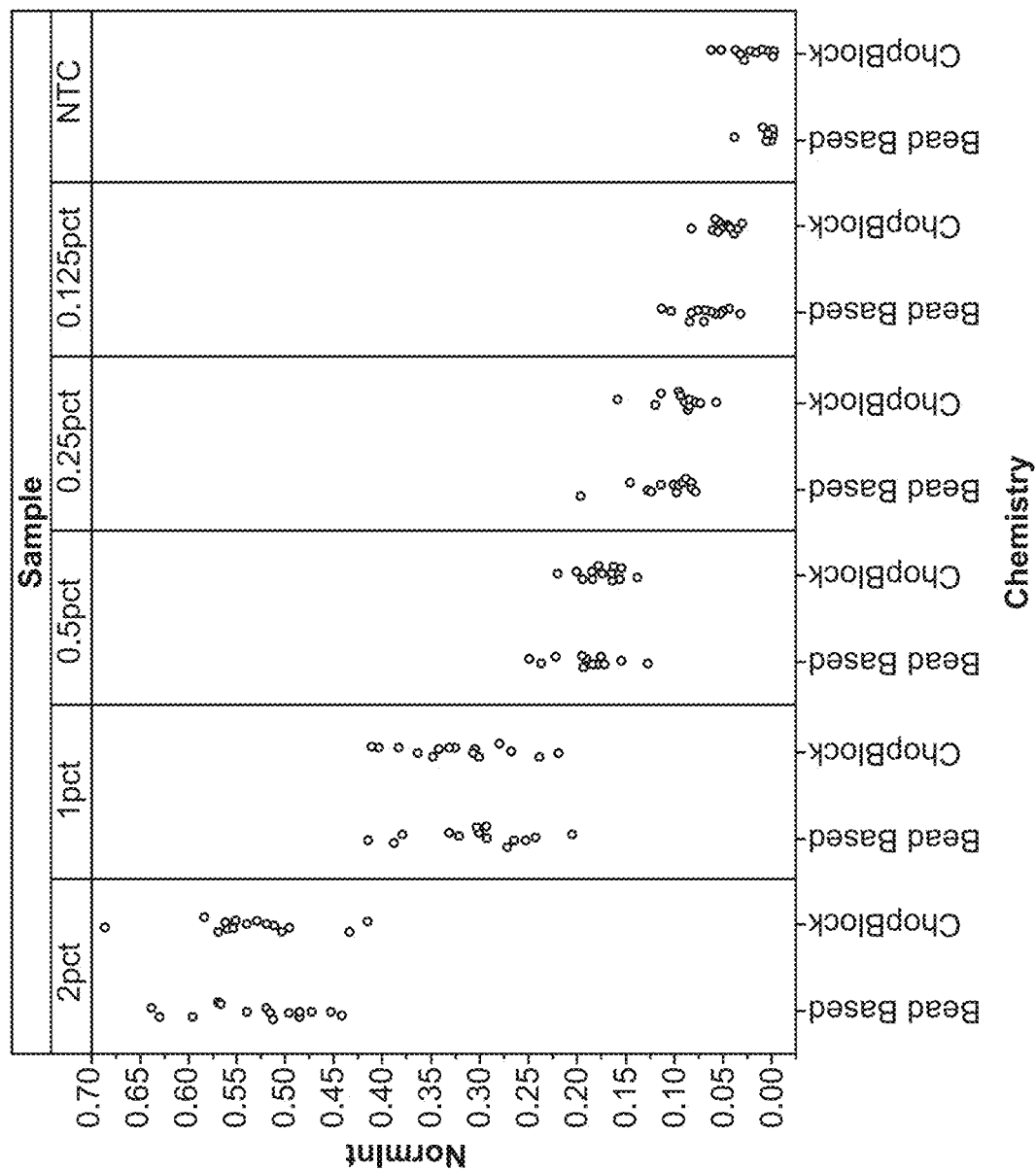
FIG. 4 shows plots for an ultra-high sensitivity assay comparing processing using bead-based chemistry (left column) vs an exonuclease reagent (Chop Block reagent)(right column).

Bead protocol (standard) was compared to Chop Block reaction for an UltraSEEK™ assay targeting IDH2 R172K (an isocitrate dehydrogenase variant) over a range of minor variant amounts (2%, 1%, 0.5%, 0.25% and 0.125% (NTC) (see panels). The experimental protocol used is described in Example 3. Assay results are depicted in FIG. 4 as normalized intensity based on SNR (y-axis). Results of processing using bead-based chemistry are shown on the left side of each panel. Results of processing using an exonuclease reagent (Chop Block reagent) are shown on the right side of each panel. In both assays, the chain terminating nucleotide was biotinylated ddUTP. Each dot is a replicate assay (16 replicates for each minor variant amount). FIG. 4 shows that over a range of levels of low abundance variants the Chop Block reaction performed similar to standard bead processing in the sensitivity level of detection.

Figure 5A:
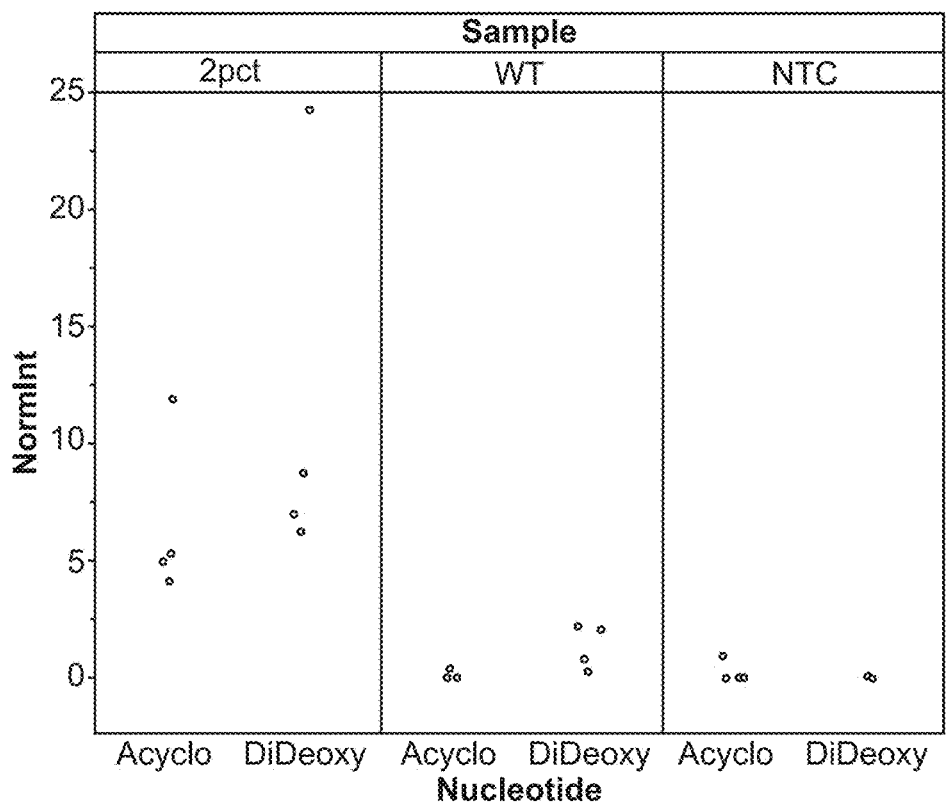
FIG. 5A and FIG. 5B show plots of normalized intensity for products of an ultra-high sensitivity assay extended with an acyclic nucleotide or a dideoxynucleotide and conditioned using an endonuclease reagent (Chop Block reagent).
Figure 5B:
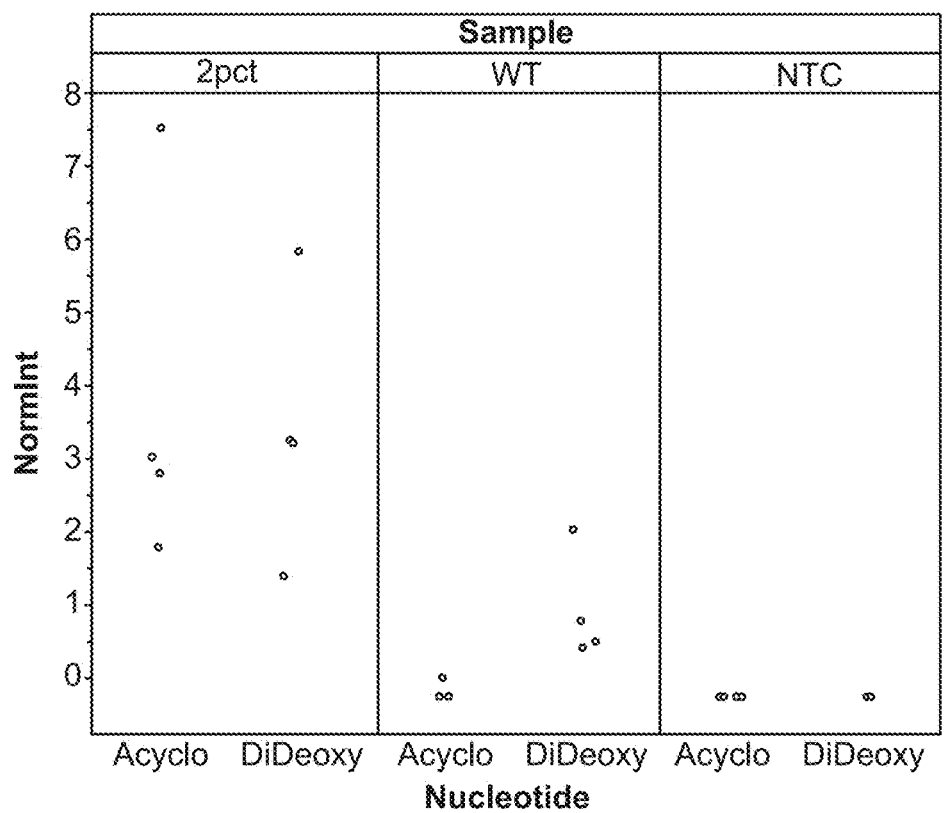

An evaluation of an UltraSEEK™ assay with Chop Block reaction was conducted comparing use of dideoxynucleotides vs acyclic nucleotides. The experiment was carried out using a protocol as described in Example 3. Assay results are depicted as normalized intensity based on SNR (y-axis) for products of an ultra-high sensitivity assay of EGFR G719S (5A) and EGFR T790M (5B) using a 2% minor variant, VVT and an NTC extended with either an acyclic nucleotide (left side of each panel) or a dideoxynucleotide (right side of each panel) and conditioned using an endonuclease reagent (Chop Block reagent). FIGS. 5A and 5B show that dideoxynucleotides result in more background noise than acyclic nucleotides.

Figure 2:
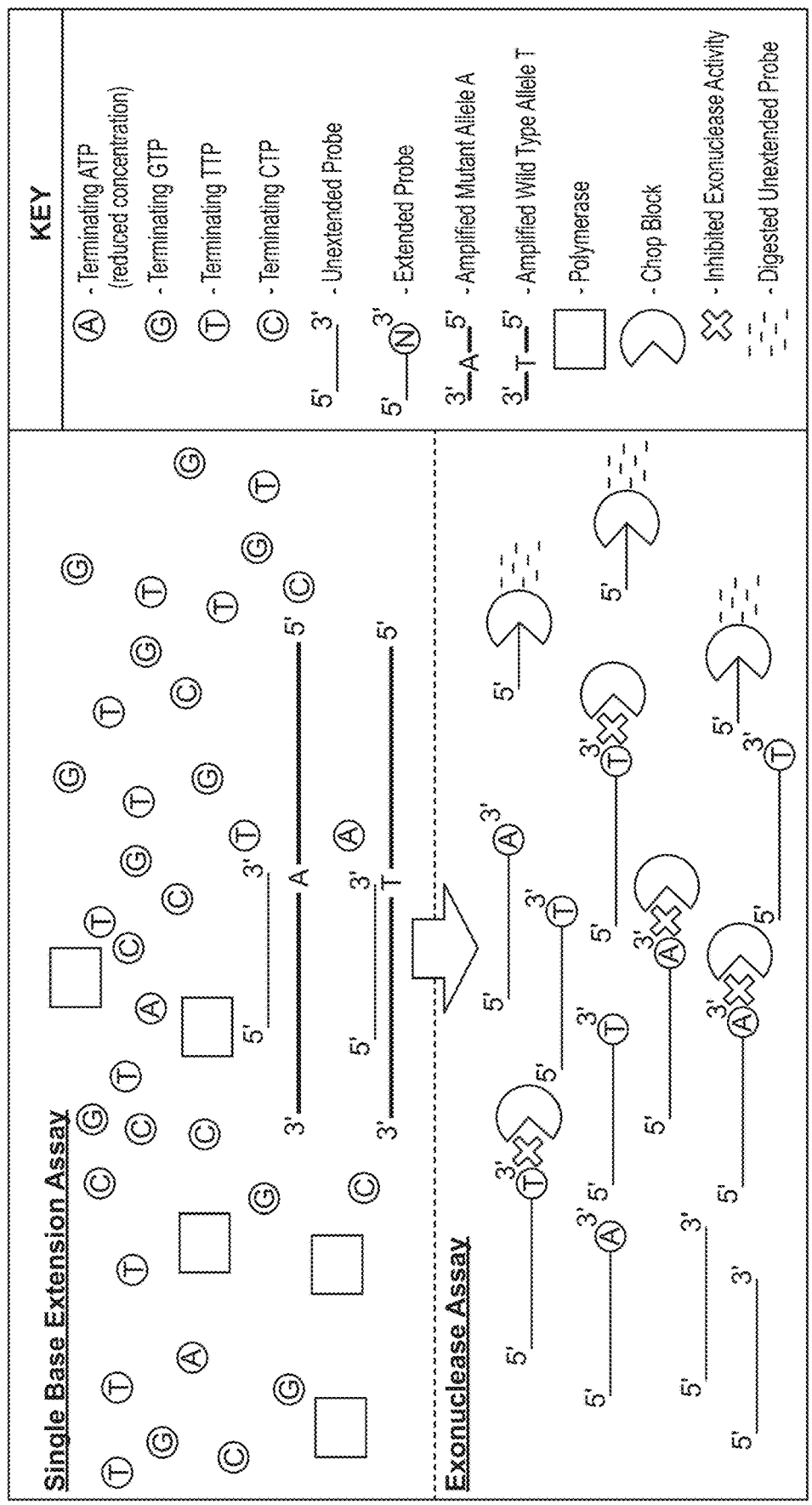
FIG. 2 is a schematic showing a single base extension high sensitivity assay with an exonuclease reagent (Chop Block reagent).

Example 5: High Sensitivity Assay (iPLEX® HS) with and without Chop Block Reagent FIG. 2 is a schematic of an embodiment of a high sensitivity assay using a single chain terminating reagent (e.g., terminating ATP) specific for extending a probe bound to high-abundance variants and three chain terminating reagents specific for extending probes bound to low-abundance variants (e.g. terminating GTP, terminating TTP terminating CTP) (see upper panel, single base extension assay). For simplicity, the figure shows a single nucleic acid species with two variants. In a multiplex assay there would be a plurality of species each having two variants. The concentration of the chain terminating reagent for high abundance variants is lower than the concentration of the chain terminating reagents for the low-abundance variants. In the lower panel (exonuclease assay) the extended probes for both variants (high and low-abundance) are protected from digestion by the Chop Block enzyme, while the unextended probes are not. For this particular example, the materials and protocols are based on Agena Bioscience's iPLEX® HS assay. One of ordinary skill in the art will recognize that an assay can be directed to different targets and/or utilize different reagents with minor adjustments to the protocol.

Multiplex PCR (Standard iPLEX® HS and iPLEX® HS w/Chop Block Reagent)

Multiplex PCR reactions targeting variants BRAF V600E, EGFR L858R, EGFR L747-T751del, EGFR L746-P750del were prepared in a final volume of 25 uL [Genomic DNA mix with each variant (Albumin excepted) in the mix at 5% allelic frequency in a background of 33 ng (Mutant DNA—Horizon Diagnostics, wild type background—Corriell Institute)]. In addition to the DNA, reaction conditions utilized 1×PCR buffer (Agena Bioscience), 100 nmol/L of each primer, 125 µmol/L of each of the 4 deoxynucleotide triphosphates (Agena Bioscience), 1.5U of Taq Polymerase (Agena Bioscience), & 1 mmol/L supplemental $MgCl_2$ (Agena Bioscience). The primer sequences are listed in Table 8. The reaction was performed in an ABI 9700 PCR system (Applied Biosystems). PCR protocol included an initial denaturation step at 95° C. for 2 min followed by 45 cycles of denaturation at 95° C. for 30 s, annealing at 60° C. for 30 s, and elongation at 72° C. for 1 min.

TABLE 8

Multiplex PCR Primers.

| PCR Primer | Sequence |
| --- | --- |
| BRAF V600E Forward (SEQ ID NO: 35) | 5'-ACGTTGGATGTTTCTTCATGAAGACC TCACAGTAA-3' |
| BRAF V600E Reverse (SEQ ID NO: 36) | 5'-ACGTTGGATGTCAATTCTTACCATCC ACAAAATG-3' |
| EGFR L858R Forward (SEQ ID NO: 37) | 5'-ACGTTGGATGGCCAGGAACGTACTGG TGAAA-3' |
| EGFR L858R Reverse (SEQ ID NO: 38) | 5'-ACGTTGGATGCCTCCTTACTTTGCCT CCTTCT-3' |
| EGFR Exon19 Forward (SEQ ID NO: 39) | 5'-ACGTTGGATGTCTCTCTGTCATAGGG ACTCTGG-3' |

TABLE 8-continued

Multiplex PCR Primers.

| PCR Primer | Sequence |
|---|---|
| EGFR Exon19 Reverse (SEQ ID NO: 40) | 5'-ACGTTGGATGGTGGGCCTGAGGTTCAGA-3' |

Shrimp Alkaline Phosphatase (Standard iPLEX® HS & iPLEX® HS w/Chop Block)

Amplified DNA was treated with shrimp alkaline phosphatase (SAP) to dephosphorylate unincorporated nucleotides from the PCR reaction. Reaction conditions use 1×SAP buffer (Agena Bioscience), 0.5U of SAP, and 5 ul of the multiplex amplified product in a total volume of 7 ul. The reaction was performed in an ABI 9700 PCR system (Applied Biosystems). SAP protocol included 37° C. incubation for 40 min followed by a protein denaturing step at 85° C. for 5 minutes.

Extension Reaction (Standard iPLEX® HS & iPLEX® HS w/Chop Block)

SAP treated amplified products were probed at specific residues in a single base extension reaction. Reaction conditions use 1× Buffer Plus (Agena Bioscience), 222 uM acyclo-TTP and 1 uM acyclo-ATP, acyclo-GTP & acyclo-CTP (New England Biolabs), 0.625-1.25 uM probes (Albumin probe was at 62.5 nM), 0.14U iPLEX® Pro enzyme (Agena Bioscience), and 7 ul of SAP treated amplified product in a total reaction volume of 9 ul. The probe sequences are listed in Table 9. The reaction was performed in an ABI 9700 PCR system (Applied Biosystems). Extension protocol included an initial denaturation step at 94° C. for 30 s, followed by 40 cycles of denaturation at 94° C. for 5 s, annealing at 52° C. for 5 s. Within the 40 cycles is another cycle between 52° C. annealing and 80° C. denaturing. Each step is 5 s and cycles 5× before continuing with the 40 main cycles. In this rationale, 200cycles are explored (see Table 10 for cycling protocol).

TABLE 9

Extension Probes-/3InvdT/ = 3' Inverted dT

| Probe | Sequence |
|---|---|
| BRAF V600E (SEQ ID NO: 41) | 5'-TGATTTTGGTCTAGCTACAG-3' |
| EGFR L858R (SEQ ID NO: 42) | 5'-TGTCAAGATCACAGATTTTGGGC-3' |
| EGFR_Exon_19_2250 (SEQ ID NO: 43) | 5'-TTTCCTTGTTGGCTTTCGGAGATGT-3' |
| EGFR_Exon_19_2240 (SEQ ID NO: 44) | 5'-CGTCGCTATCAAGGAAT-3' |
| Low Mass Control (SEQ ID NO: 45) | 5'-GTGACTCGTGGT/3InvdT/ |
| High Mass Control (SEQ ID NO: 46) | 5'-GTTGGGGTCCAGACTCTGCCCGTTTGGT/3InvdT/ |

TABLE 10

Single Base Extension Cycling Protocol

| | | |
|---|---|---|
| 95° C. for 30 seconds | | |
| 95° C. for 5 seconds | | 40 cycles |
| 52° C. for 5 seconds | 5 cycles | |
| 80° C. for 5 seconds | | |
| 72° C. for 3 minutes | | |
| 4° C. for ∞ | | |

Chop Block Cleanup

Extension reaction products were cleaned of unreacted probes in the Chop Block reaction. Reaction conditions use 1× Buffer (Agena Bioscience, PCR Buffer), 1.5 µg Chop Block, and 9 ul extension reaction products in a total volume of 14 µl. The chop block reaction was incubated in an ABI 9700 PCR system (Applied Biosystems). The reaction is incubated at 60° C. for 30 min and then the Chop Block protein is heat denatured at 85° C. for 10 min.

Sample Conditioning (Standard iPLEX® HS)

Standard iPLEX® HS extension products are diluted with 41 ul water and are reacted with 5 µl anion exchange resin (Agena Bioscience) slurry that introduces about 3.5 mg of resin. The reaction was incubated at room temperature for 30 min on a rotating hematology mixer.

Sample Conditioning (iPLEX® HS w/Chop Block)

iPLEX® HS with Chop Block treated samples were diluted with 36 ul water and reacted with 5 µl anion exchange resin (Agena Bioscience) slurry that introduces about 3.5 mg of resin. The reaction was incubated at room temperature for 30 min on a rotating hematology mixer.

Sample Dispensing (Standard iPLEX® HS & iPLEX® HS w/Chop Block)

Resin treated analyte was dispensed onto matrix elements arrayed on a silica chip using the rs1000 Nanodispenser (Agena Bioscience). Dispense volumes range between 12 to 20 nl. Calibrant analyte that consists of three distinct peaks were dispensed onto separate elements of the silica chip by the Nanodispenser.

Data Acquisition (Standard iPLEX® HS & iPLEX® HS w/Chop Block)

Dispensed chip arrays were introduced to the Agena MassARRAY® instrument. The instrument is a Matrix Assisted Laser Desorption/Ionization Time-of-Flight (MALDI-TOF) mass spectrometer. Acquisition parameters include the following: shots (n)—20; Maximum Acquisitions—9; Minimum Good Spectra—9; Maximum Good Spectra—9. Mass spectra peaks were reported out as normalized intensity by reporting software. By normalizing, peaks across spectra can be compared. To create the normalized value, either peak signal to noise, area, or height is used. The normalization is done by deriving a peak ratio (dividing a mutant peak value (SNR, area, or height) by the wild-type peak value (SNR, area, or height).

FIGS. 7A and 7B show spectra for Standard iPLEX® HS assay and iPLEX® HS assay w/Chop Block reaction), respectively. Both reactions used the same 4-plex PCR and extension reactions according to iPLEX® HS processing. The positive mutant is a 5% EGFR L858R. The peaks labeled "w" denote wild type analyte peaks, the peak labeled "a" denotes mutant analyte peak, the peaks labeled "I" denote the internal standards, the peaks labeled with downward arrow marked "u" denote un-extended probe and the upward arrow marked "u" denote the masses of the un-extended probes that have been digested by the Chop Block reagent. Peaks (labeled u down arrow) representing un-extended probe in the spectra of FIG. 7A (No Chop Block reaction) that are digested (Chop Block reaction) and thus no longer present (labeled u up arrow) in the spectra of FIG. 7B. In FIG. 7B the peak labelled a (representing mutant) and w (representing wild-type) have a greater signal above noise as compared to corresponding peaks in FIG. 7A where the un-extended oligonucleotides u represent a significant signal in the spectra. Cleaning up the spectra of unextended oli-gonucleotides (using Chop Block enzyme) that might scale out minor variants into noise may potentially increase the sensitivity of the iPLEX® HS assay. Also, removing the signal peaks produced by unextended oligonucleotides frees up portions of the spectra occupied by the unextended oligonucleotides allowing for more mass regimes to be used in an iPLEX® HS assay.

Example 6: Multiplex Genotyping Assay (iPLEX®)

FIG. 1 is a schematic of an embodiment of a genotyping assay. All four chain terminating reagents are used at the same concentration to extend probes bound to target nucleic acid species (both variants) (see upper panel, single base extension assay). For simplicity, the figure shows a single nucleic acid species with two variants. In a multiplex assay there would be a plurality of species each having two variants. In the lower panel (exonuclease assay) the extended probes for both variants of a nucleic acid species are protected from digestion by the Chop Block enzyme, while the unextended probes are not. For this particular example, the materials and protocols are based on Agena Bioscience's iPLEX® PRO assay.

Multiplex PCR

Multiplex PCR reactions were prepared in a final volume of 25 ul. In addition to the DNA, reaction conditions utilized 1×PCR buffer (Agena Bioscience), 100 nmol/L of each primer, 500 µmol/L of each of the 4 deoxynucleotide tri-phosphates (Agena Bioscience), 1.5U of Taq Polymerase (Agena Bioscience), & 1 mmol/L supplemental $MgCl_2$ (Agena Bioscience). PCR protocol included an initial dena-turation step at 95° C. for 2 min followed by 45 cycles of denaturation at 95° C. for 30 s, annealing at 60° C. for 30 s, and elongation at 72° C. for 1 min.

Shrimp Alkaline Phosphatase

Amplified DNA was treated with shrimp alkaline phos-phatase (SAP) to dephosphorylate unincorporated nucleo-tides from the PCR reaction. Reaction conditions use 1×SAP buffer (Agena Bioscience), 0.5U of SAP, and 5 ul of the multiplex amplified product in a total volume of 7 ul. SAP protocol included 37° C. incubation for 40 min followed by a protein denaturing step at 85° C. for 5 minutes.

Extension Reaction

SAP treated amplified products were probed at specific residues in a single base extension reaction. Reaction con-ditions use 1× Buffer Plus (Agena Bioscience), 222 uM acyclo-NTP mix (Agena Bioscience), 0.625-1.25 uM probes, 0.14U iPLEX® Pro enzyme (Agena Bioscience), and 7 ul of SAP treated amplified product in a total reaction volume of 9 ul. Extension protocol included an initial denaturation step at 94° C. for 30 s, followed by 40 cycles of denaturation at 94° C. for 5 s, annealing at 52° C. for 5 s. Within the 40 cycles is another cycle between 52° C. annealing and 80° C. denaturing. Each step is 5 s and cycles 5× before continuing with the 40 main cycles. In this rationale, 200cycles are explored (see Table 11 for cycling protocol).

TABLE 11

Single Base Extension Cycling Protocol

| 95° C. for 30 seconds | | |
| 95° C. for 5 seconds | | 40 cycles |
| 52° C. for 5 seconds | 5 cycles | |
| 80° C. for 5 seconds | | |
| 72° C. for 3 minutes | | |
| 4° C. for ∞ | | |

Chop Block

Extension reaction products were cleaned of unreacted probes in the Chop Block reaction. Reaction conditions use 1× Buffer (20 mM Hepes, 100 mM KCl, and 5 mM MgCl2, pH 7.5), 1.5 µg Chop Block, and 9 ul extension reaction products in a total volume of 12 µl. The chop block reaction was incubated in an ABI 9700 PCR system (Applied Bio-systems). The reaction was incubated at 60° C. for 30 min and then the Chop Block protein was heat denatured at 85° C. for 10 min.

Sample Dispensing

Resin treated analyte was dispensed onto matrix elements arrayed on a silica chip using the rs1000 Nanodispenser (Agena Bioscience) or Chip Prep Module (CPM-Agena Bioscience). Dispense volumes range between 12 to 20 nl for rs1000 dispensing and 50-80 nl for the CPM. Calibrant analyte that consists of three distinct peaks were dispensed onto separate elements of the silica chip by either dispenser.

Data Acquisition

Dispensed chip arrays were introduced to the Agena MassARRAY® instrument. The instrument is a Matrix Assisted Laser Desorption/Ionization Time-of-Flight (MALDI-TOF) mass spectrometer. Acquisition parameters include the following: shots (n)—20; Maximum Acquisi-tions—9; Minimum Good Spectra—9; Maximum Good Spectra—9. Mass spectra peaks were reported out as nor-malized intensity by reporting software. By normalizing, peaks across spectra can be compared. To create the nor-malized value, either peak signal to noise, area, or height is used. The normalization was done by deriving a peak ratio (dividing a mutant peak value (SNR, area, or height) by the wild-type peak value (SNR, area, or height).

Example 7: Synthesis of Chop Block Protein

A His-tagged Chop Block protein (His-TTHB178, having the sequence set forth as SEQ ID NO:49) was synthesized as follows (GenScript, Piscataway, NJ and Empirical Biosci-ence, Grand Rapids, MI):
  (a) Published amino acid sequence was used (e.g., sub-mitted as GenBank Accession No. BAD71974.1 and set forth as SEQ ID NO:47) for gene synthesis and codon optimization.
  (b) Gene synthesis and codon optimization
  (c) Sub cloning into appropriate expression vector—*E. Coli*, Expression Vector pET30a. The gene was expressed as an N-His tagged protein (SEQ ID NO:49) in *E. Coli*, using the expression vector pET30a, and the expression was optimized. Plasmid prep and DNA QC was performed, before transformation of the plasmids into the appropriate bacterial expression strain (GenScript: *E. Coli* strain BL21 (DE3) was transformed with the recombinant plasmid. A single colony was inoculated into LB medium containing kanamycin. The culture was incubated at 37° C., 200 rpm and then induced with IPTG. SDS-PAGE was used to monitor the expression.

(d) Protein expression evaluation and optimization (scale up protein expression using optimized conditions (5 L TB fermentation (GenScript); 50 mL LB fermentation (Empirical)). GenScript: For the scale up, BL21 (DE3) stored in glycerol was inoculated into LB medium containing kanamycin and cultured at 37° C. When the $OD_{600}$ reached about 4, the cell culture was induced with IPTG at 15° C. for 16 hours. The cells were harvested by centrifugation.

(e) Purification to reach desired protein amounts and purity (GenScript: Cell pellets were resuspended in lysis buffer followed by sonication. The supernatant after centrifugation was kept for future purification. Protein was obtained from supernatant of cell lysate, two-step purification by Ni column and Superdex 75 column. The protein was dialyzed and sterilized using a 0.22 µM filter, before being stored in aliquots; Empirical: the protein was obtained from the supernatant of the cell lysate. The supernatant was then purified via $Ni^{2+}$ affinity chromatography. A desalting step was then performed to remove imidazole and exchange the protein into the glycerol free storage buffer (50 mM Tris-HCl, 150 mM NaCl))

(f) Tag removal and separation of tag-free protein (not done, but can be done if desired)

(g) Refolding in case of insoluble protein (not done, but can be done if needed)

(h) Purity and molecular weight analysis and detection of the N-His tagged protein using SDS-PAGE and Western Blot (for tagged protein).

GenScript: The purity and molecular weight of the protein was estimated by densitometric analysis of the Coomassie Blue-stained SDS-PAGE gel under reducing conditions. Western Blot analysis also was performed. The purity of the protein in Buffer 1 (50 mM Tris-HCl, 150 mM NaCl, 10% glycerol, pH 8.0) was found to be about 85%; in Buffer 2 (50 mM Tris-HCl, 150 mM NaCl, pH 8.0) was found to be about 85% and in Buffer 3 (1×PBS, pH 7.4) was found to be about 90%.

Empirical: The purity and molecular weight of the protein in buffer (50 mM Tris-HCl, 150 mM NaCl) was estimated by analysis of Coomassie Blue-stained SDS-PAGE and found to be about 75%

(i) Bradford assay for quantitation was performed by GenScript, using BSA as the standard. The concentration of the N-His tagged TTHB178 protein was found to be 24.5 mg/ml in Buffer 1, 23.2 mg/ml in Buffer 2 and 28.2 mg/ml in Buffer 3.

Empirical: The concentration of the protein was estimated by measuring the absorbance at 280 nm using a Nanodrop 2000 spectrophotometer. The activity of the protein was found to be 1.70+/−0.02 $pmole_{probe}$/min, as detected via hydrolysis of the exonuclease detection probe.

Example 8: Non-Limiting Examples of Embodiments

Listed hereafter are non-limiting examples of certain embodiments of the technology.

A1. A method for detecting the presence, absence or amount of one or more target nucleic acids, comprising:
(a) hybridizing each of the one or more target nucleic acids to an oligonucleotide that comprises a region that corresponds to a portion of a target nucleic acid, thereby generating hybridized oligonucleotides;
(b) contacting the hybridized oligonucleotides with an extension composition comprising one or more chain terminating reagents under extension conditions; thereby generating extended oligonucleotides;
(c) contacting the products of (b) with an enzyme having 3' to 5' exonuclease activity, whereby unextended oligonucleotides are digested and extended oligonucleotides comprising a chain terminating reagent are not digested; and
(c) analyzing the extended oligonucleotides, thereby detecting the presence, absence or amount of the one or more target nucleic acids.

A2. The method of embodiment A1, wherein the chain terminating reagent when incorporated into an oligonucleotide blocks the 3' to 5' exonuclease activity of the enzyme.

A2.1. The method of embodiment A2, wherein the chain terminating reagent is is a chain terminating nucleotide.

A2.2. The method of embodiment A2.1, wherein the chain terminating nucleotide is modified at a 3' carbon of a pentose sugar moiety of the chain terminating nucleotide.

A2.3. The method of embodiment A2.2, wherein the chain terminating reagent is a dideoxynucleotide.

A2.4. The method of embodiment A2.3, wherein the dideoxynucleotide is selected from ddATP, ddGTP, ddCTP, ddTTP and ddUTP.

A2.5. The method of embodiment A2.1, wherein the chain terminating reagent is an acyclic nucleotide.

A2.5.1. The method of embodiment A2.5, wherein the acyclic nucleotide is selected from acyATP, acyCTP, acyGTP, acyTTP and acy-Bromo-UTP.

A2.6. The method of any one of embodiments A1 to A2.5.1, wherein a plurality of target nucleic acids are detected in a single, multiplexed reaction.

A3. The method of any one of embodiments A1 to A2.6, wherein the enzyme is specific for single-stranded DNA.

A4. The method of any one of embodiments A1 to A3, wherein the the 3' to 5' exonuclease activity of the enzyme is inhibited by a dideoxynucleotide or an acyclic nucleotide.

A4.1. The method of embodiment A4, wherein the enzyme is from *Thermus thermophilus*.

A4.2. The method of embodiment A4.1, wherein the enzyme is TTHB178.

A5. The method of any one of embodiment of A1 to A4.2, wherein the extended oligonucleotide comprises a detectable label.

A5.1. The method of embodiment of A5, wherein the terminating nucleotide comprises the detectable label.

A5.2. The method of embodiment of A5.1, wherein the detectable label is a fluorescent label or dye.

A5.3. The method of embodiment of A5.2, wherein the fluorescent label or dye is detected by electrophoresis or real time PCR.

A6. The method of embodiment A5, wherein the detectable label is a mass label.

A7. The method of embodiment A6, wherein the mass label is a mass distinguishable tag that is located 5' of the region of the oligonucleotide that corresponds to a portion of the target nucleic acid or the chain terminating reagent comprises the mass-distinguishable tag.

A8. The method of embodiment A6 or A7, wherein detection of the mass label is by mass spectrometry.

49

A9. The method of embodiment A8, wherein the mass spectrometry is Matrix Assisted Laser Desorption Ionization (MALDI) mass spectrometry.

A10. The method of any one of embodiments A1 to A9, wherein the enzyme is in a buffer with a glycerol concentration of about 50%.

A10.1. The method of any one of embodiments A1 to A9, wherein the enzyme is in a buffer with a glycerol concentration of less than about 50%.

A11. The method of any one of embodiments A1 to A9, wherein the enzyme in a buffer without glycerol.

A12. The method of any one of embodiments A1 to A9, wherein the enzyme is in a 10% glycerol
Tris buffer, or a Tris buffer without glycerol.

A13. The method of any one of embodiments A1 to A12, wherein prior to (a) the target nucleic acid is amplified to produce amplicons.

A14. The method of embodiment A13, wherein the amplicons are contacted with an agent that removes terminal phosphates from any nucleotides not incorporated into the amplicons.

A15. The method of embodiment A14, wherein the agent that removes terminal phosphates is a phosphatase.

A16. The method of embodiment A15, wherein the phosphatase is alkaline phosphatase.

A17. The method of embodiment A16, wherein the alkaline phosphatase is shrimp alkaline phosphatase or recombinant shrimp alkaline phosphatase.

A18. The method of any one of embodiments A1 to A17, wherein the one or more chain terminating reagents consist of one chain terminating reagent.

A19. The method of any one of embodiments A1 to A17, wherein the one or more chain terminating reagents consist of two chain terminating reagents.

A20. The method of any one of embodiments A1 to A17, wherein the one or more chain terminating reagents consist of three chain terminating reagents.

A21. The method of any one of embodiments A1 to A17, wherein the one or more chain terminating reagents consist of four chain terminating reagents.

B1. A method for detecting the presence, absence or amount of variants of a plurality of target nucleic acid species, comprising:
  (a) preparing a plurality of amplicons derived from a plurality of target nucleic acid species, or portions thereof, wherein each target nucleic acid species comprises a low-abundance variant and a high-abundance variant;
  (b) hybridizing the amplicons to a plurality of oligonucleotide species, each oligonucleotide species specifically corresponds to amplicons of a target nucleic acid species, wherein (i) an oligonucleotide species hybridizes to amplicons derived from the low-abundance variant and the high-abundance variant of a target nucleic acid species at a position 5' to a single base position that differs between the low-abundance variant and the high-abundance variant of the target nucleic acid species, thereby generating hybridized oligonucleotides;
  (c) contacting the hybridized oligonucleotides with an extension composition comprising a chain terminating reagent specific for the low-abundance variants under extension conditions; wherein the hybridized oligonucleotides that hybridize to the low-abundance variants are extended by the chain terminating reagent, thereby generating extended oligonucleotides and the hybridized oligonucleotides that hybridize to the high-abundance variants are not extended;

50

(d) contacting the products of (c) with an enzyme having 3' to 5' exonuclease activity, whereby unextended oligonucleotides are digested and extended oligonucleotides are not digested; and
  (e) analyzing the extended oligonucleotides of (d), thereby detecting the presence, absence or amount of variants of a plurality of target nucleic acid species.

B2. The method of embodiment B1, wherein the enzyme is from *Thermus thermophilus*.

B2.1. The method of embodiment B2, wherein the enzyme is TTHB178.

B2.2. The method of any one of embodiment B1 to B2.1, wherein variants of a plurality of target nucleic acids are detected in a single, multiplexed reaction.

B3. The method of any one of embodiments B1 to B2.2, wherein a low-abundance variant is a mutant allele and a high-abundance variant is a wild type of the allele.

B4. The method of any one of embodiments B1 to B3, wherein a low-abundance variant is a somatic mutation.

B5. The method of any one of embodiments B1 to B4, wherein a low-abundance variants has one or more insertions or a deletions and a high-abundance variant does not have one or more insertions or deletions.

B6. The method of any one of embodiments B1 to B5, wherein the low-abundance variant of a target nucleic acid species is present in a copy number that is about 0.1% to about 5% of the copy number of the target nucleic acid species.

B7. The method of any one of embodiments B1 to B6, wherein a low-abundance variant of a target nucleic acid species is present in a copy number that is about 1% or less of the copy number of the target nucleic acid species.

B7.1. The method of any of embodiments B1 to B5, wherein for a nucleic acid species the total copy number of the low-abundance variant and the high-abundance variant is at least about 1000 copies and the low-abundance variant represents about 0.1% of the total copy number.

B7.2. The method of any of embodiments B1 to B5, wherein for a nucleic acid species the total copy number of the low-abundance variant and the high-abundance variant is at least about 100 copies and the low-abundance variant represents about 0.1% of the total copy number.

B7.3. The method of any of embodiments B1 to B5, wherein for a nucleic acid species the copy number of the low-abundance variant is about 0.01% to about 0.1% of the total copy number of the target nucleic acid species.

B8. The method of any one of embodiments B1 to B7.3, wherein the chain terminating reagent when incorporated into an oligonucleotide blocks the 3' to 5' exonuclease activity of the enzyme.

B8.1. The method of embodiment B8, wherein the chain terminating reagent is a chain terminating nucleotide.

B8.2. The method of embodiment B8.1, wherein the chain terminating nucleotide is modified at a 3' carbon of a pentose sugar moiety of the chain terminating nucleotide.

B9. The method of embodiment B8.2, wherein the chain terminating reagent is a di deoxynucleotide.

B9.1. The method of embodiment B9, wherein the dideoxynucleotide is selected from ddATP, ddGTP, ddCTP, ddTTP and ddUTP.

B10. The method of embodiment B8.1, wherein the chain terminating nucleotide is an acyclic nucleotide.

B10.1 The method of embodiment B10, wherein the acyclic nucleotide is selected from acyATP, acyCTP, acyGTP, acyTTP and acy-Bromo-UTP.

B10.2 The method of any one of embodiments B1 to B10.1, wherein the enzyme is specific for single-stranded DNA.

B10.3. The method of any one of embodiments B1 to B10.2, wherein the 3' to 5' exonuclease activity of the enzyme is inhibited by a dideoxynucleotide or an acyclic nucleotide.

B11. The method of any one of embodiments B1 to B10.3, wherein the plurality of target nucleic acid species is about 2 to about 100 target nucleic acid species and are in a single reaction.

B12. The method of any one of embodiment of B1 to B11, wherein each extended oligonucleotide comprises a detectable label.

B12.1. The method of embodiment of B12, wherein the terminating nucleotide comprises the detectable label.

B12.2. The method of embodiment of B12.1, wherein the detectable label is a fluorescent label or dye.

B12.3. The method of embodiment of B12.2, wherein the fluorescent label or dye is detected by electrophoresis or real time PCR.

B13. The method of embodiment B12, wherein the detectable label is a mass label.

B14. The method embodiment of B13, wherein the mass label is a mass distinguishable tag that is located 5' of a region of the oligonucleotide that hybridizes to an amplicon or the chain terminating reagent comprises the mass-distinguishable tag.

B15. The method of embodiment B13 or B14, wherein detection of the mass of the extended oligonucleotide is by mass spectrometry.

B16. The method of embodiment B15, wherein the mass spectrometry is Matrix Assisted Laser Desorption Ionization (MALDI) mass spectrometry.

B17. The method of any one of embodiments B1 to B16, wherein the enzyme is in a buffer with a glycerol concentration of about 50%.

B18. The method of any one of embodiments B1 to B16, wherein the enzyme is in a buffer with a glycerol concentration of less than about 50%.

B19. The method of any one of embodiments B1 to B16, wherein the enzyme in a buffer without glycerol.

B20. The method of any one of embodiments B1 to B16, wherein the enzyme is in a 10% glycerol Tris buffer, or a Tris buffer without glycerol.

B21. The method of any one of embodiments B1 to B20, wherein the amplicons produced in (a) are contacted with an agent that removes terminal phosphates from any nucleotides not incorporated into the amplicons.

B22. The method of embodiment B21, wherein the agent that removes terminal phosphates is a phosphatase.

B23. The method of embodiment B22, wherein the phosphatase is alkaline phosphatase.

B24. The method of embodiment B23, wherein the alkaline phosphatase is shrimp alkaline phosphatase or recombinant shrimp alkaline phosphatase.

B25. The method of any one of embodiments B1 to B24, wherein the signal to noise ratio for the detecting the presence, absence or amount of variants of a plurality of target nucleic acid species is greater when un-extended oligonucleotides are digested by the enzyme than the signal to noise ratio when un-extended oligonucleotides are not digested by the enzyme.

C1. A method for detecting the presence, absence or amount of variants of a plurality of target nucleic acid species, comprising:
  (a) preparing a plurality of amplicons derived from a plurality of target nucleic acid species, or portions thereof, wherein each target nucleic acid species comprises a low-abundance variant and a high-abundance variant;
  (b) hybridizing the amplicons to a plurality of oligonucleotide species, each oligonucleotide species specifically corresponds to amplicons of a target nucleic acid species, wherein (i) an oligonucleotide species hybridizes to amplicons derived from the low-abundance variant and the high-abundance variant of a target nucleic acid species at a position 5' to a single base position that differs between the low-abundance variant and the high-abundance variant of the target nucleic acid species, (ii) the nucleotide at the single base position is the same or different for each of the high-abundance variants of the plurality of target nucleic acid species, (iii) the nucleotide at the single base position is the same for each of the low-abundance variants of the plurality of target nucleic acid species and (iv) none of the nucleotides at the single base position for the high-abundance variants of the plurality of target nucleic acid species is the same as the nucleotide at the single base position for the low-abundance variants of the plurality of target nucleic acid species; thereby generating hybridized oligonucleotides;
  (c) contacting the hybridized oligonucleotides with an extension composition comprising a chain terminating reagent specific for the low-abundance variants and one, two or three chain terminating reagents specific for one or more of the high-abundance variants under extension conditions; wherein: (i) the concentration of the one, two or three chain terminating reagents specific for one or more high-abundance variants are each at a concentration less than the concentration of the chain terminating reagent specific for the low-abundance variants and (ii) the extension conditions comprise multiple thermal cycles, thereby generating extended oligonucleotides comprising a chain terminating reagent specific for the low-abundance variants of the plurality of target nucleic acid species and extended oligonucleotides comprising a chain terminating reagent specific for the high-abundance variants of the plurality of target nucleic acid species;
  (d) contacting the products of (c) with an enzyme having 3' to 5' exonuclease activity, whereby unextended oligonucleotides are digested and extended oligonucleotides comprising a chain terminating reagent are not digested; and
  (e) detecting the extended oligonucleotides; thereby detecting the presence, absence or amounts of the variants of a plurality of nucleic acid species.

C2. The method of embodiment C1, wherein the enzyme is from *Thermus thermophilus*.

C2.1. The method of embodiment C2, wherein the enzyme is TTHB178.

C2.2. The method of any one of embodiments C1 to C2.1, wherein variants of a plurality of nucleic acid species are detected in a single, multiplexed reaction.

C3. The method of any one of embodiments C1 to C2.2, wherein a low-abundance variant is a mutant allele and a high-abundance variant is a wild type of the allele.

C4. The method of any one of embodiments C1 to C3, wherein a low-abundance variant is a somatic mutation.

C5. The method of any one of embodiments C1 to C4, wherein a low-abundance variant has one or more insertions or a deletions and a high-abundance variant does not have one or more insertions or deletions.

C6. The method of any one of embodiments C1 to C5, wherein the low-abundance variant of a target nucleic acid species is present in a copy number that is about 0.1% to about 5% of the copy number of the target nucleic acid species.

C7. The method of any one of embodiments C1 to C5, wherein the low-abundance variant of a target nucleic acid species is present in a copy number that is about 1% or less of the copy number of the target nucleic acid species.

C8. The method of any of embodiments C1 to C5, wherein for a nucleic acid species the total copy number of the low-abundance variant and the high-abundance variant is at least about 1000 copies and the low-abundance variant represents about 0.1% of the total copy number.

C9. The method of any of embodiments C1 to C5, wherein for a nucleic acid species the total copy number of the low-abundance variant and the high-abundance variant is at least about 100 copies and the low-abundance variant represents about 0.1% of the total copy number.

C10. The method of any of embodiments C1 to C8, wherein for a nucleic acid species the copy number of the low-abundance variant is about 0.01% to about 0.1% of the total copy number of the target nucleic acid species.

C11. The method of any of embodiments C1 to 010, wherein the concentration of each of the one, two or three chain terminating reagents specific for the high-abundance variants is at a concentration of about 0.01% to about 30% relative to the concentration of the specific chain terminating reagent for the low-abundance variants.

C12. The method of any of embodiments C1 to 010, wherein the concentration of each of the one, two or three chain terminating reagents specific for the high-abundance variant is about 0.3% to about 30% of the concentration of the chain terminating reagent specific for the low-abundance variants.

C13. The method of any of embodiments C1 to 010, wherein the concentration of each of the one, two or three chain terminating reagents specific for the high-abundance variant is about 1% to about 20% of the concentration of the chain terminating reagent specific for the low-abundance variants.

C14. The method of any of embodiments C1 to 010, wherein the concentration of each of the one, two or three chain terminating reagents specific for the high-abundance variant is about 1% to about 10% of the concentration of the chain terminating reagent specific for the low-abundance variants.

C15 The method of any of embodiments C1 to 010, wherein the concentration of each of the one, two or three chain terminating reagents specific for the high-abundance variants is at a concentration of about 1% to about 2% relative to the concentration of the specific chain terminating reagent for the low-abundance variants.

C16. The method of any one of embodiments C1 to C15, wherein the one, two or three chain terminating reagents specific for the high-abundance variants consist of one chain terminating reagent.

C17. The method of any one of embodiments C1 to C15, wherein one, two or three chain terminating reagents specific for the high-abundance variants consist of two chain terminating reagents.

C18. The method of any one of embodiments C1 to C15, wherein the one, two or three chain terminating reagents specific for the high-abundance variants consist of three chain terminating reagents.

C18.1. The method of any one of embodiments C1 to C18, wherein a chain terminating reagent when incorporated into an oligonucleotide blocks the 3' to 5' exonuclease activity of the enzyme.

C18.2. The method of embodiment C18.1, wherein the chain terminating reagent is is a chain terminating nucleotide.

C18.3. The method of embodiment C18.2, wherein the chain terminating nucleotide is modified at a 3' carbon of a pentose sugar moiety of the chain terminating nucleotide.

C19. The method of embodiment C18.3, wherein the chain terminating reagent is a di deoxynucleotide.

C20. The method of embodiment C19, wherein the dideoxynucleotide is selected from ddATP, ddGTP, ddCTP, ddTTP and ddUTP.

C21. The method of embodiment C18.2, wherein the chain terminating nucleotide is an acyclic nucleotide.

C21.1. The method of embodiment C21, wherein the acyclic nucleotide is selected from acyATP, acyCTP, acyGTP, acyTTP and acy-Bromo-UTP.

C21.2. The method of any one of embodiments C1 to C21.1, wherein the enzyme is specific for single-stranded DNA.

C21.3. The method of any one of embodiments C1 to C21.2, wherein the 3' to 5' exonuclease activity of the enzyme is inhibited a dideoxynucleotide or an acyclic nucleotide.

C22. The method of any one of embodiments C1 to C21.3, wherein the plurality of target nucleic acid species is about 2 to about 100 target nucleic acid species and are in a single reaction.

C23. The method of any one of embodiment of C1 to C22, wherein each extended oligonucleotide comprises a detectable label.

C23.1. The method of embodiment of C23, wherein the terminating nucleotide comprises the detectable label.

C23.2. The method of embodiment of C23.1, wherein the detectable label is a fluorescent label or dye.

C23.3. The method of embodiment of C23.2, wherein the fluorescent label or dye is detected by electrophoresis or real time PCR.

C24. The method of embodiment C23, wherein the detectable label is a mass label.

C25. The embodiment of C24, wherein the mass label is a mass distinguishable tag that is located 5' of a region of the oligonucleotide that hybridizes to an amplicon or the chain terminating reagent comprises the mass-distinguishable tag.

C26. The method of embodiment C24 or C25, wherein detection of the mass of the extended oligonucleotide is by mass spectrometry.

C27. The method of embodiment C26, wherein the mass spectrometry is Matrix Assisted Laser Desorption Ionization (MALDI) mass spectrometry.

C28. The method of any one of embodiments C1 to C27, wherein the enzyme is in a buffer with a glycerol concentration of about 50%.

C29. The method of any one of embodiments C1 to C27, wherein the enzyme is in a buffer with a glycerol concentration of less than about 50%.

C30. The method of any one of embodiments C1 to C27, wherein the enzyme in a buffer without glycerol.

C31. The method of any one of embodiments C1 to C27, wherein the enzyme is in a 10% glycerol Tris buffer, or a Tris buffer without glycerol.

C32. The method of any one of embodiments C1 to C31, wherein the amplicons produced in (a) are contacted with an agent that removes terminal phosphates from any nucleotides not incorporated into the amplicons.

C33. The method of embodiment C32, wherein the agent that removes terminal phosphates is a phosphatase.

C34. The method of embodiment C33, wherein the phosphatase is alkaline phosphatase.

C35. The method of embodiment C34, wherein the alkaline phosphatase is shrimp alkaline phosphatase or recombinant shrimp alkaline phosphatase.

C36. The method of any one of embodiments C1 to C35, wherein in the absence of detection of an extended oligonucleotide comprising a chain terminating reagent specific for a low-abundance variant, the detection of an extended oligonucleotide comprising a chain terminating reagent specific for a high-abundance variant provides a positive control to assess whether a reaction failed or if the sample only contains the high-abundance variant.

C37. The method of any one of embodiments C1 to C36, wherein the signal to noise ratio for the detecting the presence, absence or amount of variants of a plurality of nucleic acid species is greater when un-extended oligonucleotides are digested by the enzyme than the signal to noise ratio when un-extended oligonucleotides are not digested by the enzyme.

D1. A method for detecting the presence, absence or amount of variants of a plurality of target nucleic acid species, comprising:
  (a) preparing a plurality of amplicons derived from a plurality of target nucleic acid species, or portions thereof, wherein each target nucleic acid species comprises a low-abundance variant and a high-abundance variant;
  (b) hybridizing the amplicons to a plurality of oligonucleotide species, each oligonucleotide species specifically corresponds to amplicons of a target nucleic acid species, wherein (i) an oligonucleotide species hybridizes to amplicons derived from the low-abundance variant and the high-abundance variant of a target nucleic acid species at a position 5' to a single base position that differs between the low-abundance variant and the high-abundance variant of the target nucleic acid species, thereby generating hybridized oligonucleotides;
  (c) contacting the hybridized oligonucleotides with an extension composition comprising chain terminating reagents, under extension conditions, wherein: (i) the high-abundance variants share a common chain terminating reagent that is specific for the high-abundance variants and is not specific for the low-abundance variants, and (ii) each of the low-abundance variants has a chain terminating reagent that is specific for the low-abundance variant and is not specific for the high-abundance variant, wherein the chain terminating reagent that is specific for the low-abundance variant either: (A) is unique for a particular low-abundance variant in the amplified mixture and is not shared by the other low-abundance variants in the amplified mixture, or (B) at least one of the low-abundance variants share a common chain terminating reagent with at least one other low-abundance variant in the amplified mixture, whereby the oligonucleotides are extended up to, or through, the nucleotide positions that are different in the low-abundance variant relative to the high-abundance variant, thereby generating chain terminated extension products corresponding to the low-abundance variants and the high-abundance variants, respectively, wherein the concentration of the chain terminating reagent specific for the high-abundance variants is less than the concentration of each of the chain terminating reagent(s) specific for the low-abundance variants;
  (d) contacting the products of (c) with an enzyme with 3' to 5' exonuclease activity, whereby unextended oligonucleotides are digested and extended oligonucleotides comprising a chain terminating reagent are not digested; and
  (e) analyzing the extended oligonucleotides, thereby detecting the presence, absence or amount of the low-abundance variants.

D2. The method of embodiment D1, wherein variants of a plurality of nucleic acid species are detected in a single, multiplexed reaction.

D3. The method of embodiment D1 or D2, wherein the sequence of a low-abundance variant, comprises an insertion or a deletion relative to the sequence of a high-abundance variant.

D4. The method of embodiment D1 or D2, wherein a low abundance variant is a single nucleotide polymorphism (SNP) variant of a high abundance variant.

D5. The method of any one of embodiments D1 to D4, wherein the low-abundance and high-abundance variants of a target nucleic acid species are mutant and wild type alleles, respectively, of the same gene.

D6. The method of any one of embodiments D1 to D3, wherein a low-abundance variant is a somatic mutation.

D7. The method of any one of embodiments D1 to D6, wherein the enzyme is from *Thermus thermophilus*.

D7.1. The method of embodiment D7, wherein the enzyme is TTHB178.

D8. The method of any one of embodiments D1 to D7.1, wherein a high-abundance variant is from a host subject and a low-abundance variant is from a subject other than a host or a low-abundance variant is from a host subject and a high-abundance variant is from a subject other than a host.

D9. The method of any one of embodiments D1 to D8, wherein the low-abundance variant of a target nucleic acid species is present at a copy number that is about 1% to about 10% of the copy number of the target nucleic acid species.

D10. The method of any one of embodiments D1 to D9, wherein the low-abundance variant of a target nucleic acid species is present at a copy number that is about 5% or less of the copy number of the target nucleic acid species.

D11. The method of any of embodiments D1 to D10, wherein the concentration of the chain terminating reagent specific for the high-abundance variant is about 0.01% to about 30% of the concentration of each of the chain terminating reagent(s) specific for the low-abundance variants.

D12. The method of any of embodiments D1 to D10, wherein the concentration of the chain terminating reagent specific for the high-abundance variant is about 0.3% to about 30% of the concentration of each of the chain terminating reagent(s) specific for the low-abundance variants.

D13. The method of any of embodiments D1 to D10, wherein the concentration of the chain terminating reagent specific for the high-abundance variant is about 1% to about 20% of the concentration of each of the chain terminating reagent(s) specific for the low-abundance variants.

D14. The method of any of embodiments D1 to D10, wherein the concentration of the chain terminating reagent specific for the high-abundance variant is about 1% to about 10% of the concentration of each of the chain terminating reagent(s) specific for the low-abundance variants.

D14.1. The method of any of embodiments D1 to D10, wherein the concentration of the chain terminating reagent specific for the high-abundance variant is about 1% to about 2% of the concentration of each of the chain terminating reagent(s) specific for the low-abundance variants.

D15. The method of any one of embodiments D1 to D14, wherein the concentration of the chain terminating reagent for the high-abundance variant varies based on the specific high-abundance variant/low-abundance variant transition.

D16. The method of any one of embodiments D1 to D15, wherein a chain terminating reagent when incorporated into an oligonucleotide blocks the 3' to 5' exonuclease activity of the enzyme.

D16.1. The method of embodiment D16, wherein the chain terminating reagent is a chain terminating nucleotide.

D16.2. The method of embodiment D16.1, wherein a chain terminating nucleotide is modified at a 3' position of a pentose sugar moiety of a chain terminating nucleotide.

D16.3. The method of embodiment D16.2, wherein the chain terminating reagent is a di deoxynucleotide.

D16.4. The method of embodiment D16.3, wherein the dideoxynucleotide is selected from ddATP, ddGTP, ddCTP, ddTTP and ddUTP.

D17. The method of embodiment D16.1, wherein the chain terminating nucleotide is an acyclic nucleotide.

D17.1. The method of embodiment D17, wherein the acyclic nucleotide is selected from acyATP, acyCTP, acyGTP, acyTTP and acy-Bromo-UTP.

D18. The method of any one of embodiments D1 to D17, wherein the enzyme is specific for single-stranded DNA.

D18.1 The method of any one of embodiments D1 to D18, wherein the 3' to 5' exonuclease activity of the enzyme is inhibited by a dideoxynucleotide or an acyclic nucleotide.

D19. The method of any one of embodiment D1 to D18.1, wherein the chain terminating reagent specific for the low-abundance variants consist of one chain terminating reagent.

D20. The method of any one of embodiment D1 to D18, wherein the chain terminating reagents specific for the low-abundance variants consist of two chain terminating reagents.

D21. The method of any one of embodiment D1 to D18, wherein the chain terminating reagents specific for the low-abundance variants consist of three chain terminating reagents.

D22. The method of any one of embodiments D1 to D21, wherein the plurality of target nucleic acid species is about 2 to about 100 target nucleic acid species and the target nucleic acid species are detected in a single reaction.

D23. The method of any one of embodiment of D1 to D22, wherein each extended oligonucleotide comprises a detectable label.

D23.1. The method of embodiment of D23, wherein the terminating nucleotide comprises the detectable label.

D23.2. The method of embodiment of D23.1, wherein the detectable label is a fluorescent label or dye.

D23.3. The method of embodiment of D23.2, wherein the fluorescent label or dye is detected by electrophoresis or real time PCR.

D24. The method of embodiment of D23, wherein the detectable label is a mass label.

D25. The embodiment of D24, wherein the mass label is a mass distinguishable tag that is located 5' of the region of the oligonucleotide that hybridizes to an amplicon or the chain terminating reagent comprises the mass-distinguishable tag.

D26. The method of embodiment D24 or D25, wherein detection of the mass of the extended oligonucleotide is by mass spectrometry.

D27. The method of embodiment D26, wherein the mass spectrometry is Matrix Assisted Laser Desorption Ionization (MALDI) mass spectrometry.

D28. The method of any one of embodiments D1 to D27, wherein the enzyme is in a buffer with a glycerol concentration of about 50%.

D29. The method of any one of embodiments D1 to D27, wherein the enzyme is in a buffer with a glycerol concentration of less than about 50%.

D30. The method of any one of embodiments D1 to D27, wherein the enzyme in a buffer without glycerol.

D31. The method of any one of embodiments D1 to D27, wherein the enzyme is in a 10% glycerol Tris buffer, or a Tris buffer without glycerol.

D32. The method of any one of embodiments D1 to D31, wherein the amplicons produced in (a) are contacted with an agent that removes terminal phosphates from any nucleotides not incorporated into the amplicons.

D33. The method of embodiment D32, wherein the agent that removes terminal phosphates is a phosphatase.

D34. The method of embodiment D33, wherein the phosphatase is alkaline phosphatase.

D35. The method of embodiment D34, wherein the alkaline phosphatase is shrimp alkaline phosphatase or recombinant shrimp alkaline phosphatase.

D36. The method of any one of embodiments D1 to D35, wherein the signal to noise ratio for the detecting the presence, absence or amount of variants of a plurality of nucleic acid species is greater when un-extended oligonucleotides are digested by the enzyme than the signal to noise ratio when un-extended oligonucleotides are not digested by the enzyme.

E1. A method for detecting the presence, absence or amount of variants of a plurality of target nucleic acid species, comprising:
  (a) preparing a plurality of amplicons derived from a plurality of target nucleic acid species, or portions thereof, wherein each target nucleic acid species comprises at least two variants;
  (b) hybridizing the amplicons to a plurality of oligonucleotide species, each oligonucleotide species specifically corresponds to amplicons of a target nucleic acid species, wherein (i) an oligonucleotide species hybridizes to amplicons derived from the variants of a target nucleic acid species at a position 5' to a single base position that differs between the variants of the target nucleic acid species, thereby generating hybridized oligonucleotides;
  (c) contacting the hybridized oligonucleotides with an extension composition comprising two, three or four chain terminating reagents in equimolar concentrations, whereby the oligonucleotides are extended up to, or through, the nucleotide position that is different between the variants of a target nucleic acid species, thereby generating chain terminated extension products corresponding to the variants;
  (d) contacting the products of (c) with an enzyme with 3' to 5' exonuclease activity, whereby unextended oligonucleotides are digested and extended oligonucleotides are not digested; and
  (e) analyzing the extended oligonucleotides; thereby detecting the presence, absence or amount of the variants.

E2. The method of embodiment E1, wherein variants of a plurality of nucleic acid species are detected in a single, multiplexed reaction.

E3. The method of embodiment E1 or E2, wherein one of the variants of a target nucleic acid species, comprises an insertion or a deletion relative to the other variant of the target nucleic acid species.

E4. The method of embodiment E1 or E2, wherein the variants of a target nucleic acid species are single nucleotide polymorphism (SNP) variants.

E5. The method of any one of embodiments E1 to E4, wherein the variants of a target nucleic acid species are mutant and wild type alleles, respectively, of the same gene.

E6. The method of embodiment E5, wherein one variant of a target nucleic acid species is a somatic mutation.

E7. The method of any one of embodiments E1 to E6, wherein the enzyme is from *Thermus thermophilus*.

E7.1. The method of embodiment E7, wherein the enzyme is TTHB178.

E8. The method of any one of embodiments E1 to E7.1, wherein each variant of a target nucleic acid species is present in a copy number that is at least about 10% of the target nucleic acid species.

E9. The method of any one of embodiments E1 to E7.1, wherein one variant of the target nucleic acid species is from a host subject and the other variant of the target nucleic acid species is from a subject other than the host.

E9.1. The method of any one of embodiments E1 to E9, wherein a chain terminating reagent when incorporated into an oligonucleotide blocks the 3' to 5' exonuclease activity of the enzyme.

E10. The method of embodiment E9.1, wherein the chain terminating reagent is a chain terminating nucleotide.

E10.1. The method of embodiment E10, wherein the chain terminating nucleotide is modified at a 3' position of a pentose sugar moiety of the chain terminating nucleotide.

E10. The method of embodiment E10.1, wherein the chain terminating reagent is a dideoxynucleotide.

E11. The method of embodiment E10, wherein a dideoxynucleotide is selected from among ddATP, ddGTP, ddCTP, ddTTP and ddUTP.

E12. The method of embodiment E10, wherein the chain terminating nucleotide is an acyclic nucleotide.

E12.1. The method of embodiment E12, wherein the acyclic nucleotide is selected from acyATP, acyCTP, acyGTP, acyTTP and acy-Bromo-UTP.

E12.2. The method of any one of embodiments E1 to E12.1, wherein the enzyme is specific for single-stranded DNA.

E12.3. The method of any one of embodiment E1 to E12.2, wherein the chain terminating reagent consists of two chain terminating reagents.

E12.4. The method of any one of embodiments E1 to E12.2, wherein the chain terminating reagent consists of three chain terminating reagents.

E12.5. The method of any one of embodiments E1 to E12.2, wherein the chain terminating reagent consists of four chain terminating reagents.

E12.6. The method of any one of embodiments E1 to E12.5, wherein the 3' to 5' exonuclease activity of the enzyme is inhibited by a dideoxynucleotide or an acyclic nucleotide.

E13. The method of any one of embodiments E1 to E12.6, wherein the plurality of target nucleic acid species is about 2 to about 100 target nucleic acid species and the target nucleic acid species are detected in a single reaction.

E14. The method of any one of embodiment of E1 to E13, wherein each extended oligonucleotide comprises a detectable label.

E14.1. The method of embodiment of E14, wherein the terminating nucleotide comprises the detectable label.

E14.2. The method of embodiment of E14.1, wherein the detectable label is a fluorescent label or dye.

E14.3. The method of embodiment of E14.2, wherein the fluorescent label or dye is detected by electrophoresis or real time PCR.

E15. The method of embodiment E14, wherein the detectable label is a mass label.

E16. The embodiment of E15, wherein the mass label is a mass distinguishable tag that is located 5' of the region of the oligonucleotide that hybridizes to an amplicon or the chain terminating reagent comprises the mass-distinguishable tag.

E17. The method of embodiment E15 or E16, wherein detection of the mass of the extended oligonucleotide is by mass spectrometry.

E18. The method of embodiment E17, wherein the mass spectrometry is Matrix Assisted Laser Desorption Ionization (MALDI) mass spectrometry.

E19. The method of any one of embodiments E1 to E18, wherein the enzyme is in a buffer with a glycerol concentration of about 50%.

E20. The method of any one of embodiments E1 to E18, wherein the enzyme is in a buffer with a glycerol concentration of less than about 50%.

E21. The method of any one of embodiments E1 to E18, wherein the enzyme in a buffer without glycerol.

E22. The method of any one of embodiments E1 to E18, wherein the enzyme is in a 10% glycerol Tris buffer, or a Tris buffer without glycerol.

E23. The method of any one of embodiments E1 to E22, wherein the amplicons produced in (a) are contacted with an agent that removes terminal phosphates from any nucleotides not incorporated into the amplicons.

E24. The method of embodiment E23, wherein the agent that removes terminal phosphates is a phosphatase.

E25. The method of embodiment E24, wherein the phosphatase is alkaline phosphatase.

E26. The method of embodiment E25, wherein the alkaline phosphatase is shrimp alkaline phosphatase or recombinant shrimp alkaline phosphatase.

E27. The method of any one of embodiments E1 to E26, wherein the signal to noise ratio for the detecting the presence, absence or amount of variants of a plurality of nucleic acid species is greater when un-extended oligonucleotides are digested by the enzyme than the signal to noise ratio when un-extended oligonucleotides are not digested by the enzyme.

F1. A method for primer extension comprising:
  (a) hybridizing a target nucleic acid to an oligonucleotide that comprises a region that corresponds to a portion of the target nucleic acid, thereby generating a hybridized oligonucleotide;
  (b) contacting the hybridized oligonucleotide with an extension composition comprising one or more chain terminating reagents under extension conditions; thereby generating extended oligonucleotides; and
  (c) contacting the products of (b) with an enzyme having 3' to 5' exonuclease activity, whereby unextended oligonucleotides are digested and extended oligonucleotides comprising a chain terminating reagent are not digested.

F2. The method of embodiment F1, wherein a chain terminating reagent when incorporated into an oligonucleotide blocks the 3' to 5' exonuclease activity of the enzyme.

F2.1. The method of embodiment F2, wherein the chain terminating reagent is is a chain terminating nucleotide.

F2.2. The method of embodiment F2.1, wherein the chain terminating nucleotide is modified at a 3' position of a pentose sugar moiety of the chain terminating nucleotide.

F2.3. The method of embodiment F2.2, wherein the chain terminating reagent is a di deoxynucleotide.

F2.4. The method of embodiment F2.3, wherein the dideoxynucleotide is selected from ddATP, ddGTP, ddCTP, ddTTP and ddUTP.

F2.5. The method of embodiment F2.1, wherein the chain terminating reagent is an acyclic nucleotide.

F2.5.1. The method of embodiment F2.5, wherein the acyclic nucleotide is selected from acyATP, acyCTP, acyGTP, acyTTP and acy-Bromo-UTP.

F3. The method of any one of embodiments F1 to F2.5.1, wherein the enzyme is specific for single-stranded DNA.

F4. The method of any one of embodiments F1 to F3, wherein the 3' to 5' exonuclease activity of the enzyme is inhibited by a dideoxynucleotide or an acyclic nucleotide.

F5. The method of embodiment F4, wherein the enzyme is from *Thermus thermophilus*.

F5.1. The method of embodiment F5, wherein the enzyme is TTHB178.

F6. The method of any one of embodiments F1 to A5.1, wherein the one or more chain terminating reagents consist of one chain terminating reagent.

F7. The method of any one of embodiments F1 to F5.1, wherein the one or more chain terminating reagents consist of two chain terminating reagents.

F8. The method of any one of embodiments F1 to F5.1, wherein the one or more chain terminating reagents consist of three chain terminating reagents.

F9. The method of any one of embodiments F1 to F5.1, wherein the one or more chain terminating reagents consist of four chain terminating reagents.

G1. A kit comprising:
  an enzyme having 3' to 5' exonuclease activity; and
  one or more chain terminating reagents that inhibit the activity of the enzyme on an oligonucleotide when the chain terminating reagent is at the 3' terminus of the oligonucleotide.

G2. The kit of embodiment G1, wherein the enzyme is from *Thermus thermophilus*.

G2.1. The kit of embodiment G2, wherein the enzyme is TTHB178.

G3. The kit of any one of embodiments G1 to G2.1, wherein the enzyme is provided in a buffer with a glycerol concentration of 50% or less.

G4. The kit of any one of embodiments G1 to G2.1, wherein the enzyme in a buffer without glycerol.

G5. The kit of any one of embodiments G1 to G2.1, wherein the enzyme is in a 10% glycerol Tris buffer, or a Tris buffer without glycerol.

G6. The kit of any one of embodiments G1 to G5, wherein the chain terminating reagent is a chain terminating nucleotide.

G7. The kit of embodiment G6, wherein the chain terminating nucleotide is modified at a 3' position of a pentose sugar moiety of the chain terminating nucleotide.

G8. The kit of embodiment G7, wherein the chain terminating reagent is a dideoxynucleotide.

G9. The kit of embodiment G8, wherein the dideoxynucleotide is selected from ddATP, ddGTP, ddCTP, ddTTP and ddUTP.

G10. The kit of embodiment G6, wherein the chain terminating reagent is an acyclic nucleotide.

G10.1. The kit of embodiment G10, wherein the acyclic nucleotide is selected from acyATP, acyCTP, acyGTP, acyTTP and acy-Bromo-UTP.

G10.2. The kit of any one of embodiments G1 to G10.1, wherein the chain terminating reagent comprises a mass-distinguishable tag.

G11. The kit of any one of embodiments G1 to G10.2, wherein the enzyme is specific for single-stranded DNA.

G12. The kit of any one of embodiments G1 to G11, comprising one or more of: oligonucleotides, a polymerase, alkaline phosphatase, one or more buffers and one or more reaction controls.

G13. The kit of any one of embodiments G1 to G12, wherein the one or more chain terminating reagents consist of one chain terminating reagent.

G14. The kit of any one of embodiments G1 to G12, wherein the one or more chain terminating reagents consist of two chain terminating reagents.

G15 The kit of any one of embodiments G1 to G12, wherein the one or more chain terminating reagents consist of three chain terminating reagents.

G16. The kit of any one of embodiments G1 to G12, wherein the one or more chain terminating reagents consist of four chain terminating reagents.

G17. The kit of any one of embodiments, G1 to G12, wherein one, two or three chain terminating reagents are specific for detection of a plurality of high-abundance variants and a chain terminating reagent is specific for detection of a plurality of low-abundance variants and the concentration of each of the one, two or three chain terminating reagents specific for the high-abundance variant is about 0.3% to about 30% of the concentration of the chain terminating reagent that is specific for the low-abundance variants.

G17.1. The kit of embodiment G17, wherein the chain terminating reagent specific for detection of the plurality of low-abundance variants and the one, two or three chain terminating reagents specific for detection of a plurality of high-abundance variants are in a single container.

G17.2. The kit of embodiment G17.1, wherein the kit comprises two or more containers each of which hold a different chain terminating reagent that is specific for detection of a plurality of low-abundance variants and one, two or three chain terminating reagents specific for detection of a plurality of high-abundance variants G18. The kit of any one of embodiments, G1 to G12, wherein one, two or three chain terminating reagents are specific for detection of a plurality of low-abundance variants and a chain terminating reagent is specific for detection of a plurality of high-abundance variants and the concentration of the chain terminating reagent specific for the high-abundance variants is about 0.3% to about 30% of the concentration of each of the one, two or three chain terminating reagents specific for the low-abundance variants.

G18.1. The kit of embodiment G18, wherein the chain terminating reagent specific for detection of the plurality of high-abundance variants and the one, two or three chain terminating reagents specific for detection of a plurality of low-abundance variants are in a single container.

G18.2. The kit of embodiment G18.1, wherein the kit comprises two or more containers each of which hold a different chain terminating reagent that is specific for detection of a plurality of high-abundance variants and one, two or three chain terminating reagents specific for detection of a plurality of low-abundance variants G19. The kit of any one of embodiments, G1 to G12, comprising two, three or four chain terminating reagents at equivalent concentrations.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claims that follow.

What is claimed is:

1. A method for detecting the presence, absence or amount of variants of one or more target nucleic acid species or amplicons thereof, comprising:
(a) contacting a sample comprising one or more target nucleic acid species or amplicons thereof with one or more primer oligonucleotides, wherein each primer oligonucleotide comprises a region that corresponds to a portion of a target nucleic acid species or amplicon thereof and wherein each of the one or more target nucleic acid species or amplicon thereof (1) comprises at least two variants and (2) each of the one or more primer oligonucleotides is specific for a target nucleic acid species or amplicon thereof and is capable of hybridizing to the variants of the target nucleic acid species or amplicon thereof at a position 5' to a single base position that differs between each of the variants of the target nucleic acid species or amplicon thereof, thereby generating hybridized oligonucleotides;
(b) contacting the hybridized oligonucleotides with an extension composition comprising one or more chain terminating reagents each specific for a variant of a target nucleic acid species or amplicon thereof under extension conditions, wherein the hybridized primer oligonucleotides are each extended up to, or through, the nucleotide position that is different between the variants of a corresponding target nucleic acid species or amplicon thereof, thereby generating extended primer oligonucleotides that each comprise a chain terminating reagent specific for one or more variants of the corresponding target nucleic acid species or amplicon thereof;
(c) contacting the products of (b) with an enzyme having 3' to 5' exonuclease activity, whereby unextended primer oligonucleotides are digested and extended primer oligonucleotides comprising a chain terminating reagent are not digested; and
(d) without subjecting the products of (b) or the products of (c) to selective capture of the extended primer oligonucleotides from the mixture of extended primer oligonucleotides and unextended primer oligonucleotides in (b) or (c), analyzing detecting the presence, absence or amount of the extended primer oligonucleotides, thereby detecting the presence, absence or amount of variants of the one or more target nucleic acid species or amplicons thereof in the sample.

2. The method of claim 1, wherein at least one chain terminating reagent, when incorporated into a primer oligonucleotide in (b), blocks the 3' to 5' exonuclease activity of the enzyme.

3. The method of claim 2, wherein at least one chain terminating reagent is a chain terminating nucleotide or all of the one or more chain terminating reagent(s) is/are a chain terminating nucleotide.

4. The method of claim 3, wherein the chain terminating reagent(s) is/are a dideoxynucleotide or an acyclic nucleotide.

5. The method of claim 4, wherein the dideoxynucleotide is selected from among ddATP, ddGTP, ddCTP, ddTTP and ddUTP and the acyclic nucleotide is selected from among acyATP, acyCTP, acyGTP, acyTTP and acy-Bromo-UTP.

6. The method of claim 1, wherein the extension composition comprises two, three or four chain terminating reagents in equimolar concentrations.

7. The method of claim 1, wherein:
(1) each of the one or more target nucleic acid species or amplicons thereof comprises a low-abundance variant and a high-abundance variant;
(2) each of the one or more primer oligonucleotides of (a) is specific for a target nucleic acid species or amplicon thereof and hybridizes to both the low-abundance variant and the high-abundance variant of the target nucleic acid species or amplicon thereof at a position 5' to a single base position that differs between the low-abundance variant and the high-abundance variant of the target nucleic acid species, thereby generating hybridized oligonucleotides;
(3) in (b), the hybridized oligonucleotides of (2) are contacted with an extension composition comprising a chain terminating reagent specific for the low-abundance variants under extension conditions; wherein the primer oligonucleotides that hybridize to the low-abundance variant are extended by the chain terminating reagent, thereby generating extended oligonucleotides, and the primer oligonucleotides that hybridize to the high-abundance variant are not extended;
(4) in (c), the products of (3) are contacted with the enzyme having 3' to 5' exonuclease activity, whereby the unextended primer oligonucleotides are digested and the extended primer oligonucleotides are not digested; and
(5) in (d), the presence, absence or amount of the extended primer oligonucleotides of (4) is detected, thereby detecting the presence, absence or amount of variants of the target nucleic acid species or amplicons thereof.

8. The method of claim 1, wherein:
(1) the sample comprises a plurality of target nucleic acid species or amplicons thereof, wherein each target nucleic acid species or amplicon thereof has a low-abundance variant and a high-abundance variant;
(2) the nucleic acids of (a) are hybridized with a plurality of primer oligonucleotides, and each primer oligonucleotide is specific for a target nucleic acid species or amplicon thereof and hybridizes to both the low-abundance variant and the high-abundance variant of the target nucleic acid species or amplicon thereof at a position 5' to a single base position that differs between the low-abundance variant and the high-abundance variant of the target nucleic acid species, thereby generating hybridized oligonucleotides, wherein:
(i) the nucleotide at the single base position is the same or different for each of the high-abundance variants of the plurality of target nucleic acid species,
(ii) the nucleotide at the single base position is the same for each of the low-abundance variants of the plurality of target nucleic acid species, and
(iii) none of the nucleotides at the single base position for the high-abundance variants of the plurality of target nucleic acid species is the same as the nucleotide at the single base position for the low-abundance variants of the target nucleic acid species, (3) in (b), the hybridized oligonucleotides of (2) are contacted with an extension composition comprising a chain terminating reagent specific for the low-abundance variants and one, two or three chain terminating reagents specific for one or more of the high-abundance variants under extension conditions, wherein:

(i) the one, two or three chain terminating reagents specific for one or more high-abundance variants are each at a concentration less than the concentration of the chain terminating reagent specific for the low-abundance variants, and (ii) the extension conditions comprise multiple thermal cycles, thereby generating extended primer oligonucleotides comprising a chain terminating reagent specific for the low-abundance variants of the plurality of target nucleic acid species and/or extended primer oligonucleotides comprising a chain terminating reagent specific for the high-abundance variants of the target nucleic acid species;

(4) in (c), the products of (3) are contacted with the enzyme having 3' to 5' exonuclease activity, whereby the unextended primer oligonucleotides are digested and the extended primer oligonucleotides comprising a chain terminating reagent are not digested; and (5) in (d), the presence, absence or amount of the extended primer oligonucleotides of (4) is detected, thereby detecting the presence, absence or amount of variants of the target nucleic acid species or amplicons thereof.

9. The method of claim 1, wherein a plurality of target nucleic acid species or amplicons thereof are detected in a single, multiplexed reaction.

10. The method of claim 1, wherein the enzyme is TTHB178.

11. The method of claim 1, wherein the primer oligonucleotides hybridized with the target nucleic acid species or amplicons thereof do not include a detectable label attached thereto and the chain terminating reagent(s) do not include a detectable label attached thereto.

12. The method of claim 1, wherein (d) does not include detection of a detectable label attached to the primer oligonucleotide(s) that are extended or attached to a chain terminating reagent.

13. The method of claim 1, wherein the extended primer oligonucleotides are analyzed by mass spectrometry.

14. The method of claim 1, wherein:

(1) the one or more target nucleic acids comprises a plurality of target nucleic acid species or amplicons thereof, wherein each species or amplicon thereof has a low-abundance variant and a high-abundance variant;

(2) the target nucleic acid species or amplicons thereof of
(a) are hybridized with a plurality of primer oligonucleotides, and each primer oligonucleotide is specific for a target nucleic acid species or amplicon thereof and hybridizes to both the low-abundance variant and the high-abundance variant of the target nucleic acid species or amplicon thereof at a position 5' to a single base position that differs between the low-abundance variant and the high-abundance variant of the target nucleic acid species, thereby generating hybridized oligonucleotides, wherein:

(i) the nucleotide at the single base position is the same for each of the high-abundance variants of the plurality of target nucleic acid species, (ii) the nucleotide at the single base position is the same or different for each of the low-abundance variants of the plurality of target nucleic acid species, and (iii) none of the nucleotides at the single base position for the low-abundance variants of the plurality of target nucleic acid species is the same as the nucleotide at the single base position for the high-abundance variants of the target nucleic acid species;

(3) in (b), the hybridized oligonucleotides of (2) are contacted with an extension composition comprising a chain terminating reagent specific for the high-abundance variants and one or more chain terminating reagents specific for one or more of the low-abundance variants under extension conditions, thereby generating extended primer oligonucleotides comprising a chain terminating reagent specific for the low-abundance variants of the plurality of target nucleic acid species and/or extended primer oligonucleotides comprising a chain terminating reagent specific for the high-abundance variants of the target nucleic acid species wherein:

(i) the high-abundance variants share a common chain terminating reagent that is specific for the high-abundance variants and is not specific for the low-abundance variants, (ii) each of the low-abundance variants has a chain terminating reagent that is specific for the low-abundance variant and is not specific for the high-abundance variant, wherein the chain terminating reagent that is specific for the low-abundance variant either: (A) is unique for a particular low-abundance variant in the composition and is not shared by the other low-abundance variants in the composition, or (B) at least one of the low-abundance variants share a common chain terminating reagent with at least one other low-abundance variant in the composition, and (iii) the concentration of the chain terminating reagent specific for the high-abundance variants is less than the concentration of the chain terminating reagent(s) specific for the low-abundance variants;

(4) in (c), the products of (3) are contacted with the enzyme having 3' to 5' exonuclease activity, whereby the unextended primer oligonucleotides are digested and the extended primer oligonucleotides comprising a chain terminating reagent are not digested; and (5) in (d), the presence, absence or amount of the extended primer oligonucleotides of (4) is detected, thereby detecting the presence, absence or amount of variants of the target nucleic acid species or amplicons thereof.

15. The method of claim 1, wherein the target nucleic acid species or amplicons thereof, the one or more primer oligonucleotides, the products of (b) and the products of (c) are not captured by binding to a solid phase.

16. The method of claim 1, wherein the target nucleic acid species or amplicons thereof, primer oligonucleotides, extended primer oligonucleotides and chain terminating reagents do not comprise a capture agent or member of a binding pair for which the other member of the binding pair is linked to a solid phase.

17. The method of claim 1, wherein the target nucleic acid species or amplicons thereof of the sample are hybridized in (a) to a plurality of primer oligonucleotides each comprising a region that corresponds to a portion of one of a plurality of target nucleic acids.

18. The method of claim 7, wherein the target nucleic acid species or amplicons thereof, the one or more primer oligonucleotides, the products of (3) and the products of (4) are not captured by binding to a solid phase.

19. The method of claim 8, wherein the target nucleic acid species or amplicons thereof, the plurality of primer oligonucleotides, the products of (3) and the products of (4) are not captured by binding to a solid phase.

20. The method of claim 14, wherein the plurality of primer oligonucleotides, the products of (3) and the products of (4) are not captured by binding to a solid phase.

* * * * *

SEQUENCE LISTING

```
<160> NUMBER OF SEQ ID NOS: 49

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acgttggatg aaggcctgct gaaaatgact                                       30

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acgttggatg ttgttggatc atattcgtcc ac                                    32

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acgttggatg gctagagaca atgaattaag ggaaa                                 35

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
acgttggatg aagaaaaaga aacagagaat ctcca                                 35
```

```
<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acgttggatg caagccctga agctcaactc                                              30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acgttggatg gatttgtgtg ggcatgacag                                              30

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
ttgtggtagt tggagct                                                            17

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
cactcttgcc tacgccac                                                           18

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
cctgctcagt gattt                                                              15

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
gttgctgtca tctcttgtgg gc                                                      22

<210> SEQ ID NO 11
```

```
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
gttgactcgt ggtt                                                      14

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
gttgactctg tggtt                                                     15

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
gtttggggcc agactctgcc cgtttggtt                                      29

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
gtttggggtc cagactctgc ccgtttggtt                                     30

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
gaagccagac tcttcgtttg gt                                             22

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
acgttggatg agtcctcgtt gtcttgttgg                                     30

<210> SEQ ID NO 17
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acgttggatg tctgagtggc catgtacagc                                       30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acgttggatg ttggttacat ccctctctgc                                       30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
acgttggatg attgcaggct caccccaatg                                       30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acgttggatg tcttcatgaa gacctcacag                                       30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acgttggatg ccacaaaatg gatccagaca                                       30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acgttggatg tggagcctct tacacccagt                                       30

<210> SEQ ID NO 23
<211> LENGTH: 30
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 23
acgttggatg gtgccaggga ccttacctta                                          30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
acgttggatg agccaggaac gtactggtga                                          30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
acgttggatg cctggtgtca ggaaaatgct                                          30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acgttggatg ctccaggaag cctacgtgat                                          30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
acgttggatg gtctttgtgt tcccggacat                                          30

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
gcccccgttc tatatcatca                                                     20

<210> SEQ ID NO 29
<211> LENGTH: 17
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 29
ccaatgttct ggtggtt                                                    17

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
cccactccat cgagatttc                                                  19

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
cgaacacacc ggagc                                                      15

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
tcttccgcac ccagc                                                      15

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
ccgtgcagct catca                                                      15

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
cactcttgcc tacgcca                                                    17

<210> SEQ ID NO 35
<211> LENGTH: 35
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 35
acgttggatg tttcttcatg aagacctcac agtaa                              35

<210> SEQ ID NO 36
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
acgttggatg tcaattctta ccatccacaa aatg                               34

<210> SEQ ID NO 37
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
acgttggatg gccaggaacg tactggtgaa a                                  31

<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
acgttggatg cctccttact ttgcctcctt ct                                 32

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
acgttggatg tctctctgtc atagggactc tgg                                33

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
acgttggatg gtgggcctga ggttcaga                                      28

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 41
tgattttggt ctagctacag                                          20

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
tgtcaagatc acagattttg ggc                                      23

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
tttccttgtt ggctttcgga gatgt                                    25

<210> SEQ ID NO 44
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
cgtcgctatc aaggaat                                             17

<210> SEQ ID NO 45
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
gtgactcgtg gtt                                                 13

<210> SEQ ID NO 46
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
gttggggtcc agactctgcc cgtttggtt                                29

<210> SEQ ID NO 47
<211> LENGTH: 296
<212> TYPE: PRT
<213> ORGANISM: Thermus thermophilus HB8

<400> SEQUENCE: 47

Met Ala Phe Gly Val Ser His Pro Val Ala Leu Asp Leu Glu Ala Thr
1               5                   10                  15

Ser Thr Asp Pro Ser Glu Ala Glu Val Leu Glu Val Ala Ala Val Asp
            20                  25                  30

Gly Glu Gly Arg Val Phe His Arg Tyr Leu Ala Thr Gln Arg Pro Leu
                35                  40                  45

Pro Pro Asp His Glu Val Phe Gln Leu Thr Gly Ile Pro Tyr Glu Glu
        50                  55                  60

Tyr Glu Ala Lys Lys Val Ala Pro Lys Glu Ala Leu Glu Glu Leu Leu
65                  70                  75                  80

Ala Phe Leu Gly Gly Arg Pro Leu Gly His Asn Leu Leu Arg Tyr
                85                  90                  95

Asp Leu Pro Leu Leu Gln Arg His Leu Glu Glu Ala Gly Leu Pro Arg
            100                 105                 110

Trp Gln Gly Glu Ala Leu Asp Thr Leu Arg Leu Ala His Leu Leu Phe
            115                 120                 125

Pro Thr Pro Pro Gly Gly Leu Glu Gly Tyr Arg Leu Gly Asp Leu Tyr
        130                 135                 140

Ala Phe Leu Leu Gly Arg Pro Leu Glu Gly Ala His Arg Ala Leu Asn
145                 150                 155                 160

Asp Ala Gln Ala Thr Leu Ala Val Phe His Arg Leu Leu Asp Arg Gly
                165                 170                 175

Arg Arg Ala Leu Ala Gln His Pro Gly Leu Val Arg Ala Trp Arg Glu
            180                 185                 190

Leu Gly Leu Pro Glu Gly His Leu Phe Pro Glu Asp Glu Gly Leu Ile
            195                 200                 205

Lys Asp Leu Leu Ala Arg Glu Ala Asp Val Glu Ala Phe Phe Val Glu
        210                 215                 220

Lys Glu Gly Arg Pro Phe Pro Ala Pro Thr Asp Leu Gly Pro Asp Leu
225                 230                 235                 240

Leu Pro Lys Pro Arg Pro Ala Gln Arg Ile Lys Glu Phe Val Gln Val
                245                 250                 255

Ala His Gly Val Ala Gly Gln Gly Leu Val Gly Arg Glu Arg Pro Leu
            260                 265                 270

His Glu Val Leu Glu Arg Gly Leu Arg Leu Ala Val Gly Glu Ala Glu
        275                 280                 285

Glu Gly Ala Val Glu Lys Glu Gly
        290                 295

<210> SEQ ID NO 48
<211> LENGTH: 888
<212> TYPE: DNA
<213> ORGANISM: Thermus thermophilus HB8

<400> SEQUENCE: 48
atggcgtttg gcgtctccca cccggtcgca ctggatctgg aagcgaccag caccgatccg     60
tctgaagctg aagtcctgga agtggcggcc gttgacggcg aaggtcgtgt ttttcatcgc    120
tatctggcaa cccagcgtcc gctgccgccg gatcacgaag tgttccaact gacgggcatt    180
ccgtatgaag aatacgaagc gaaaaaagtt gctccgaaag aagcgctgga agaactgctg    240
gcgtttctgg gcggtcgtcc gctgctgggt cataacctgc tgcgttacga tctgccgctg    300
ctgcagcgtc acctgaaaga agccggtctg ccgcgttggc aaggtgaagc tctggacacc    360
ctgcgcctgg cacatctgct gtttccgacg ccgccgggcg gtctggaagg ttatcgtctg    420

```
ggtgatctgt acgcgttcct gctgggtcgt ccgctggaag gtgcacaccg tgctctgaat     480
gatgcacagg ctaccctggc cgtctttcat cgtctgctgg accgtggtcg tcgcgcactg     540
gcacaacacc cgggtctggt gcgtgcatgg cgtgaactgg gcctgccgga aggtcacctg     600
tttccggaag atgaaggcct gattaaagac ctgctggcgc gtgaagccga tgtcgaagcc     660 ttttcgtgg aaaaagaagg ccgtccgttt ccggcaccga cggatctggg tccggacctg     720
ctgccgaaac gcgtccggc acagcgcatc aaagaattcg tgcaagttgc ccatggcgtt     780
gccggtcagg gtctggtcgg tcgtgaacgt ccgctgcacg aagtgctgga acgtggtctg     840
cgtctggcgg tgggtgaagc ggaagaaggt gctgtggaaa agaaggt                   888
```

<210> SEQ ID NO 49
<211> LENGTH: 303
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

```
Met His His His His His His Met Ala Phe Gly Val Ser His Pro Val
1               5                   10                  15

Ala Leu Asp Leu Glu Ala Thr Ser Thr Asp Pro Ser Glu Ala Glu Val
                20                  25                  30

Leu Glu Val Ala Ala Val Asp Gly Glu Gly Arg Val Phe His Arg Tyr
            35                  40                  45

Leu Ala Thr Gln Arg Pro Leu Pro Pro Asp His Glu Val Phe Gln Leu
        50                  55                  60

Thr Gly Ile Pro Tyr Glu Glu Tyr Glu Ala Lys Lys Val Ala Pro Lys
65                  70                  75                  80

Glu Ala Leu Glu Glu Leu Leu Ala Phe Leu Gly Gly Arg Pro Leu Leu
                85                  90                  95

Gly His Asn Leu Leu Arg Tyr Asp Leu Pro Leu Leu Gln Arg His Leu
            100                 105                 110

Glu Glu Ala Gly Leu Pro Arg Trp Gln Gly Glu Ala Leu Asp Thr Leu
        115                 120                 125

Arg Leu Ala His Leu Leu Phe Pro Thr Pro Pro Gly Gly Leu Glu Gly
    130                 135                 140

Tyr Arg Leu Gly Asp Leu Tyr Ala Phe Leu Leu Gly Arg Pro Leu Glu
145                 150                 155                 160

Gly Ala His Arg Ala Leu Asn Asp Ala Gln Ala Thr Leu Ala Val Phe
                165                 170                 175

His Arg Leu Leu Asp Arg Gly Arg Arg Ala Leu Ala Gln His Pro Gly
            180                 185                 190

Leu Val Arg Ala Trp Arg Glu Leu Gly Leu Pro Glu Gly His Leu Phe
        195                 200                 205

Pro Glu Asp Glu Gly Leu Ile Lys Asp Leu Leu Ala Arg Glu Ala Asp
    210                 215                 220

Val Glu Ala Phe Phe Val Glu Lys Gly Arg Pro Phe Pro Ala Pro
225                 230                 235                 240

Thr Asp Leu Gly Pro Asp Leu Leu Pro Lys Pro Arg Pro Ala Gln Arg
                245                 250                 255

Ile Lys Glu Phe Val Gln Val Ala His Gly Val Ala Gly Gln Gly Leu
            260                 265                 270

Val Gly Arg Glu Arg Pro Leu His Glu Val Leu Glu Arg Gly Leu Arg
```

```
                  275                 280                 285
Leu Ala Val Gly Glu Ala Glu Glu Gly Ala Val Glu Lys Glu Gly
    290                 295                 300
```